US008039436B2

(12) United States Patent
Sauvageau et al.

(10) Patent No.: US 8,039,436 B2
(45) Date of Patent: Oct. 18, 2011

(54) MUTATED HOXB4 PROTEINS WITH IMPROVED STABILITY, AND METHODS OF USE THEREOF

(75) Inventors: Guy Sauvageau, Montreal (CA); Keith Humphries, Vancouver (CA); Denis-Claude Roy, Montreal (CA); Nathalie Beslu, Montreal (CA)

(73) Assignees: British Columbia Caner Agency Branch, Vancouver (CA); Adaerata, Limited Partnership, Montreal (CA); Valorisation-Recherche, Limited Partnership, Montreal (CA); RSEM, Limited Partnership, Montreal (CA)

( * ) Notice: Subject to any disclaimer, the term of this patent is extended or adjusted under 35 U.S.C. 154(b) by 531 days.

(21) Appl. No.: 12/129,919

(22) Filed: May 30, 2008

(65) Prior Publication Data

US 2008/0300187 A1 Dec. 4, 2008

Related U.S. Application Data

(60) Provisional application No. 60/941,472, filed on Jun. 1, 2007.

(30) Foreign Application Priority Data

Jun. 1, 2007 (CA) .................................... 2590593

(51) Int. Cl.
*A61K 38/16* (2006.01)
*C07K 14/00* (2006.01)
(52) U.S. Cl. ........................................ 514/12; 530/300
(58) Field of Classification Search .................. None
See application file for complete search history.

(56) References Cited

U.S. PATENT DOCUMENTS 6,812,339 B1 * 11/2004 Venter et al. ............... 536/24.31

OTHER PUBLICATIONS

Harvey et al., Embryonic expression andnuclear localization of Xenopus homeobox (Xhox) gene products. The EMBO Journal 5:1237-1244, 1986.*
Amsellem et al., "Ex Vivo expansion of human hematopoietic stem cells by direct delivery of the HOXB4 homeoprotein", Nat. Med., (2003), 1423-1427, vol. 9, No. 11.
Antonchuk et al., "HOXB4 overexpression mediates very rapid stem cell regeneration and competitive hematopoietic repopulation", Exp Hematol., (2001), 1125-1134, vol. 29.
Antonchuk et al., "HOXB4-Induced Expansion of Adult Hematopoietic Stem Cells Ex Vivo", Cell, (2002), 39-45, vol. 109.
Beslu et al., "Molecular interactions involved in HOXB4-induced activation of HSC self-renewal", Blood, (2004), 2307-2314, vol. 104, No. 8.
Bhardwaj et al., "Sonic hedgehog induces the proliferation of primitive human hematopoietic cells via BMP regulation", Nat. Med., (2001), 172-180, vol. 2, No. 2.
Buske et al., "Deregulated expression of HOXB4 enhances the primitive growth activity of human hematopoietic cells", Blood, (2002), 862-868, vol. 100.
Cellot et al., "Sustained in vitro trigger of self-renewal divisions in HOXB4hi PBX1lo hematopoietic stem cells", Exp Hematol., (2007), 802-816, vol. 35.
Chowdary et al., "Accumulation of p53 in a Mutant Cell Line Defective in the Ubiquitin Pathway", Mol. Cell. Biol., (1994), 1997-2003, vol. 14, No. 3.
Corish et al., "Attenuation of green fluorescent protein half-life in mammalian cells", Protein Engineering, (1999), 1035-1040, vol. 12, No. 12.
Coulombe et al., "Rapid Turnover of Extracellular Signal-Regulated Kinase 3 by the Ubiquitin Proteasome Pathway . . . ", Mol. Cell. Biol., (2003), 4542-4558, vol. 23, No. 13.
de Haan et al., "In Vitro Generation of Long-Term Repopulating Hematopoietic Stem Cells by Fibroblast Growth Factor-1", Dev. Cell., (2003), 241-251, vol. 4.
Gabellini et al., "Early mitotic degradation of the homeoprotein HOXC10 is potentially linked to cell cycle progression", Embo Journal, (2003), 3715-3724, vol. 22, No. 14.
Hershko et al., "The Ubiquitin System", Annu. Rev. Biochem., (1998), 425-479, vol. 67.
Karanu et al., "The Notch Ligand Jagged-1 represents a novel growth factor of Human Hematopoietic Stem Cells", J. Exp. Med.-Rockfeller Univ, (2000), 1365-1372, vol. 192-No. 9.
Kroon et al., "HOXA9 transforms primary bone marrow cells through specific collaboration with Meis1a but not Pbx1b", EMBO J., (1998), 3714-3725, vol. 17-No. 13.
Kroon et al., "NUP98-HOXA9 expression in hemopoietic stem cells induces chronic and acute myeloid leukemias in mice", EMBO J., (2001), 350-361, vol. 20, No. 3.
Krosl et al., "Human hematopoietic stem cells can be expanded ex vivo using recombinant TAT-HOXB4 protein", Biology of Blood and Marrow Transplantation. (2005a); 11:19.
Krosl et al., "In vitro expansion of hematopoietic stem cells by recombinant TAT-HOXB4 protein", Nat Med, (2003), 1428-1432, vol. 9—No. 11.
Krosl et al., "The Competitive Nature of HOXB4-Transduced HSC is limited by PBX1: The Generation of Ultra-Competitive . . . ", Immunity by Cell Press, (2003), 561-571 vol. 18.
Lawrence et al., "Mice bearing a targeted interruption of the homeobox gene HOXA9 have defects in myeloid, erythroid, and lymphoid . . . ", Blood, (1997), 1922-1930, vol. 89.
Meinnel et al., "Impact of the N-terminal amino acid on targeted protein degradation", Biol. Chem., (2006), 839-851, vol. 387.
Nagahara et al., "Transduction of full-length TAT fusion proteins into mammalian cells: TAT-p27kipl induces cell migration", Nat Med, 1998, 1449-1452, vol. 4-No. 12.
Ohh et al., "An intact NEDD8 pathway is required for Cullin-dependent ubiquitylation in mammalian cells", EMBO rep., 2002, 177-182, vol. 31-No. 21.

(Continued)

*Primary Examiner* — Ruixiang Li
(74) *Attorney, Agent, or Firm* — Goudreau Gage Dubuc; Julie Gauvreau

(57) ABSTRACT

A polypeptide, the amino acid sequence of which comprises a sequence as set forth in SEQ ID NO:2, including at least one mutation within the degron domain of the polypeptide encompassed between positions 1 and 35 of the sequence, wherein said at least one mutation reduces the susceptibility of the polypeptide to ubiquitin-proteasome degradation.

21 Claims, 28 Drawing Sheets

OTHER PUBLICATIONS

Ory et al., "A stable human-derived packaging cell line for production of high titer retrovirus/vesicular stomatitis . . . ", Proc. Nat. Acad. Sci. USA, (1996), 11400-11406.

Pickart et al., "Back to the Future with Ubiquitin", Cell, 2004, 181-190, vol. 116.

Pilat et al., "HOXB4 enforces equivalent fates of ES-cell-derived and adult hematopoietic cells", Proc. Nat. Acad. Sci. USA, (2005), 12101-12106, vol. 102, No. 34.

Schiedlmeier et al., "High-level ectopic HOXB4 expression confers a profound in vivo competitive growth advantage on human cord . . . ", Blood, 2003, 1759-1768, vol. 101, No. 5.

Schwarze et al., "In vivo protein transduction: Delivery of a Biologically Active Protein into the Mouse", Science, 1999, 1569-1572, vol. 285.

Thorsteinsdottir et al., "The oncoprotein E2A-Pbx1a collaborates with HOXA9 to acutely transform primary bone marrow cells", Mol. Cell Biol., 1999, 6355-6366.

Thorsteinsdottir et al., "Overexpression of the myeloid leukemia-associated HOXA9 gene in bone marrow cells induces stem cell expansion", Blood, 2002, 121-129, vol. 99.

Willert et al., "Wnt proteins are lipid-modified and can act as stem cell growth factors", Nature, (2003), 448-452, vol. 423.

Zhang et al., "CUL-4A stimulates ubiquitylation and degradation of the HOXA9 homeodomain protein", EMBO J., (2003), 6057-6067, vol. 22, No. 22.

\* cited by examiner

A

```
                            1         10        20        30
      Homo sapiens  HOXB4   MAMSSFLINSNYVDPKFPPCEEYSQSDYLPS
                    HOXA4   .T..........IE.....F...A.HSGSGG
                    HOXC4   .I...Y.MD...I..............NS.I.E
                    HOXD4   .V...YMV..K............L.GG..GE

CONSENSUS          MXMSSXXXXSXYXXPKFPPXEEYXQXXXXXX
```

B

```
                              1         10        20        30
                     HOXB4   MAMSSFLINS-N---------------YV---DPKFPPCEEYSQSDYLPS
       Endeis spinosa DFD    --.CP..M..GS---------------.---......S.....NS.I..
          Bombyx mori DFD    --......M.G-G---------------.QPQP......S.....A..I.P
  Tribolium castaneum DFD    .-.....M.P-GTALPTYQQPQHISGVV.---......S...N.NS.I.P
```

MAMSSFLINSNYVDPKFPPCEEYSQSDYLPSDHSPGYYAGGQRRESSFQPEAGFGRRAACTVQRYAACRDPG
PPPPPPPPPPPPPPPGLSPRAPAPPPAGALLPEPGQRCEAVSSSPPPPPCAQNPLHPSPSHSACKEPVVYPW
MRKVHVSTVNPNYAGGEPKRSRTAYTRQQVLELEKEFHYNRYLTRRRRVEIAHALCLSERQIKIWFQNRRMK
WKKDHKLPNTKIRSGGAAGSAGGPPGRPNGGPRAL

B

```
atggctat gagttctttt ttgatcaact caaactatgt cgaccccaag ttccctccat
gcgaggaata ttcacagagc gattacctac ccagcgacca ctcgcccggg tactacgccg
gcggccagag gcgagagagc agcttccagc cggaggcggg cttcgggcgg cgcgcggcgt
gcaccgtgca gcgctacgcg gcctgccggg accctgggcc cccgccgcct ccgccaccac
ccccgccgcc cccgccaccg cccggtctgt ccctcgggc tcctgcgccc cacccgccg
gggccctcct cccggagccc ggccagcgct gcgaggcggt cagcagcagc ccccgccgc
ctccctgcgc ccagaacccc ctgcacccca gcccgtccca ctccgcgtgc aaagagcccg
tcgtctaccc ctggatgcgc aaagttcacg tgagcacggt aaacccccaat tacgccggcg
gggagcccaa gcgctctcgg accgcctaca cgcgccagca ggtcttggag ctggagaagg
aatttcacta caaccgctac ctgacacggc gccggagggt ggagatcgcc cacgcgctct
gcctctccga gcgccagatc aagatctggt tccagaaccg cgcatgaag tggaaaaaag
accacaagtt gcccaacacc aagatccgct cgggtggtgc ggcaggctca gccggagggc
cccctggccg gcccaatgga ggccccgcg cgctctag
```

MGYYAGGQRRESSFQPEAGFGRRAACTVQRYAACRDPGPPPPPPPPPPPPPPGLSPRAPAPPPAGALLPEP
GQRCEAVSSSPPPPPCAQNPLHPSPSHSACKEPVVYPWMRKVHVSTVNPNYAGGEPKRSRTAYTRQQVLELE
KEFHYNRYLTRRRRVEIAHALCLSERQIKIWFQNRRMKWKKDHKLPNTKIRSGGAAGSAGGPPGRPNGGPRA
L

B

```
        atgggg tactacgccg gcggccagag gcgagagagc agcttccagc cggaggcggg
        cttcgggcgg cgcgcggcgt gcaccgtgca gcgctacgcg gcctgccggg accctgggcc
        cccgccgcct ccgccaccac cccgccgcc cccgccaccg cccggtctgt cccctcgggc
        tcctgcgccg ccacccgccg gggccctcct cccggagccc ggccagcgct gcgaggcggt
        cagcagcagc cccccgccgc ctccctgcgc ccagaacccc ctgcacccca gcccgtccca
        ctccgcgtgc aaagagcccg tcgtctaccc ctggatgcgc aaagttcacg tgagcacggt
        aaacccaat tacgccggcg gggagcccaa gcgctctcgg accgcctaca cgcgccagca
        ggtcttggag ctggagaagg aatttcacta caaccgctac ctgacacggc gccgagggt
        ggagatcgcc cacgcgctct gcctctccga gcgccagatc aagatctggt tccagaaccg
        gcgcatgaag tggaaaaaag accacaagtt gcccaacacc aagatccgct cgggtggtgc
        ggcaggctca gccggagggc cccctggccg gcccaatgga ggccccgcg cgctctag
```

C MAMSSFLINSNYVDPKFPPCEEYSQSDYLPSDHSP

MATTGALGNYYVDSFLLGADAADELGAGRYAPGTLGQPPRQAAALAEHPDFSPCSFQSKAAVFGAS
WNPVHAAGANAVPAAVYHHHHHPYVHPQAPVAAAAPDGRYMRSWLEPTPGALSFAGLPSSRPYGIK
PEPLSARRGDCPTLDTHTLSLTDYACGSPPVDREKQPSEGAFSENNAENESGGDKPPIDPNNPAAN
WLHARSTRKKRCPYTKHQTLELEKEFLFNMYLTRDRRYEVARLLNLTERQVKIWFQNRRMKMKKIN
KDRAKDE

B

```
        atgg  ccaccaccgg  ggccctgggc  aactactatg  tggactcctt  cctgctgggc
gccgacgctg  ctgatgagct  gggtgcggga  cgctacgctc  cagggaccct  gggtcaaccc
ccaaggcagg  cggcagctct  ggccgaacac  cccgacttca  gtccttgcag  cttccagtcc
aaggcggcgg  tgtttggtgc  ctcgtggaac  ccagtgcacg  cggcgggcgc  caatgcggtg
cctgctgcag  tgtatcatca  ccaccaccac  ccctacgtgc  atcccaggc   gcccgtggcg
gcggcggcgc  cggacggcag  gtatatgcgc  tcctggctgg  aacccacgcc  cggtgcgctc
tccttcgcgg  gcttaccctc  cagccggcct  tatggcatta  aacctgaacc  gctctcggcc
agaaggggtg  actgtccac   gcttgacact  cacactttgt  ccctgactga  ctatgcttgt
ggttctcctc  cagttgatag  agaaaaacaa  cccagcgaag  gcgccttctc  cgaaaacaat
gccgagaatg  agagcggcgg  agacaagccc  ccatcgatc   ccaataaccc  ggctgccaac
tggctacatg  ctcgctccac  tcggaagaag  cgatgcccct  acacaaaaca  ccagacgctg
gaactggaga  aggagtttct  gtttaacatg  tacctcacac  gggaccgcag  gtacgaggtg
gcccggctgc  tcaacctcac  cgaaaggcag  gtcaagatct  ggttccagaa  ccgcaggatg
aaaatgaaga  aaatcaacaa     ggaccgagca  aaagacgagt     ga
```

MTMSSFLINSNYIEPKFPPFEEYAQHSGSGGADGGPGGGPGYQQPPAPPTQHLPLQQPQLPHA
GGGREPPASYYAPRTAREPAYPAAALYPAHGAADTAYPYGYRGGASPGRPPQPEQPPAQAKG
PAHGLHASHVLQPQPPPPLQPRAVPPAAPRRCEAAPATPGVPAGGSAPACPLLLADKSPLGLK
GKEPVVYPWMKKIHVSAVNPSYNGGEPKRSRTAYTRQQVLELEKEFHFNRYLTRRRRIEIAHTL
CLSERQVKIWFQNRRMKWKKDHKLPNTKMRSSNSASASAGPPGKAQTQSPHLHPHPSTST
PVPSSI

B

```
  1 aaaacgacaa cgcgagaaaa attagtattt ttgcacttca caaattaatg accatgagct
 61 cgtttttgat aaactccaac tacatcgagc ccaagttccc tcccttcgag gagtacgcgc
121 agcacagcgg ctcgggcggc gcagacggcg gcccgggcgg gggccccggc taccagcagc
181 ccccagcgcc cccgacccag cacctgccgc tgcagcagcc cagctccct cacgcgggcg
241 gcggccgaga gccccctgcc tcctactacg cgccgcggac cgcccgcgag cccgcctacc
301 ctgctgccgc gctgtacccc gcgcatgggg ccgcggacac cgcctacccc tatggctacc
361 gcggcggcgc cagccccggg cggccgcccc agcccgagca gccccggcg caagccaagg
421 gcccagcgca cggcctgcat gcgagccacg tcctgcagcc cagccgccg ccgcccctgc
481 agcctcgcgc cgtgccccca gcggcccgc ggcgctgcga ggcggccccc gccaccccag
541 gcgtcccggc aggggcagc gccccgcgt gccgctgct cttggccgac aagagcccgc
601 tgggcctgaa gggcaaggag cccgtggtgt accctggat gaagaagatc catgtcagcg
661 ccgttaaccc cagttataac ggaggggagc ctaagcgctc tcgaaccgcc tacacccggc
721 agcaggtctt ggagctggag aaggagttcc acttcaatcg ctacctgacc cggcggcgcc
781 gcatcgagat cgcccacacg ctctgtttgt ctgagcgcca ggtcaagatc tggtttcaga
841 accggaggat gaagtggaag aaagaccaca actgcccaa caccaagatg cgatcctcca
901 attcggcctc ggcctctgcc ggcccaccag ggaaagcaca aactcagagc ccacacctcc
961 atccccaccc ccacccgagc acctccacac ccgttccctc ctccatataa tcttctagag
```

Figure 18

```
1021 atcttaacca gtttctatcc cttacctgct tttctcttct cttctcctgc tccgttcctc 1081 atccacccct ccccatctgg accataatag acaccaaaac aaacccaaat tggtgaaaag 1141 aataatcaaa aagaagacat tatccggtta agagtctgtg ctggttgcca cccaagagag 1201 aacagttgtc caggatgctg gctggtggaa caacctgctg gcccgaaaca aggctgccag 1261 gtgtggatac ctgagaagga ctacttggta tcaaatactt ttgagatggc tacagtcagc 1321 tagctggaca gcccatgctg agtggggaca tacacttgca tctttgttga aagcagaaga 1381 agacagaccc tttccccacc ttccttacct cctcttcccc cattaaggca gctcatccaa 1441 gcttgtattt aactgaataa atgagtagac attgtggacc tcacaagatt atttaattct 1501 taagatgtgt agaccttgat ggtaggtgtg acatgttagt ttttcttact tgcatttatt 1561 taagacactg ttacagagat actgttgtcc ccttctgggg cacggtcttt ggggagaggg 1621 gagtgcattt agacttatgt ggaactgtac aaattgtgat gtggctacat agaaagccat 1681 gtgctaagaa taaactccat ttaaaaaaca ttaaaaatct aagattcatg tgttttctaa 1741 gcttttcatt aagaaaacaa aagtcctctg gattgagata cttgaccttg catgtaaaaa 1801 ccttgtagat agcttgagct ggattcactt ggattctgac ggct
```

MIMSSYLMDSNYIDPKFPPCEEYSQNSYIPEHSPEYYGRTRESGFQHHHQELYPPPPPRPSYPE
RQYSCTSLQGPGNSRGHGPAQAGHHHPEKSQSLCEPAPLSGASASPSPAPPACSQPAPDHPS
SAASKQPIVYPWMKKIHVSTVNPSYNGGEPKRSRTAYTRQQVLELEKEFHYNRYLTRRRRIEIAH
SLCLSERQIKIWFQNRRMKWKKDHRLPNTKVRSAPPAGAAPSTLSAATPGTSEDHSQSATPPEQ
QRAEDITRL

B

```
   1 agaaaaacga caaagcgaga aaaattattt tccactccag aaattaatga tcatgagctc
  61 gtatttgatg gactctaact acatcgatcc gaaatttcct ccatgcgaag aatattcgca
 121 aaatagctac atccctgaac acagtccgga atattacggc cggaccaggg aatcgggatt
 181 ccagcatcac caccaggagc tgtacccacc accgcctccg cgccctagct accctgagcg
 241 ccagtatagc tgcaccagtc tcaggggcc cggcaattcg cgaggccacg gccggccca
 301 ggcgggccac caccaccccg agaaatcaca gtcgctctgc gagccggcgc tctctcagg
 361 cgcctccgcc tcccgtccc cagccccgcc agcctgcagc cagccagccc cgaccatcc
 421 ctccagcgcc gccagcaagc aacccatagt ctacccatgg atgaaaaaaa ttcacgttag
 481 cacggtgaac cccagttata acggagggga acccaagcgc tcgaggacag cctatacccg
 541 gcagcaagtc ctggaattag agaaagagtt tcattacaac cgctacctga cccgaaggag
 601 aaggatcgag atcgcccact cgctgtgcct ctctgagagg cagatcaaaa tctggttcca
 661 aaaccgtcgc atgaaatgga agaaggacca ccgactcccc aacaccaaag tcaggtcagc
 721 accccggcc ggcgctgcgc ccagcaccct ttcggcagct accccgggta cttctgaaga
 781 ccactcccag agcgccacgc cgccggagca gcaacgggca gaggacatta ccaggttata
 841 aaacataact cacacccctg cccccacccc atgccccac cctcccctca cacacaaatt
 901 gactcttatt tatagaattt aatatatata tatatatata tatataggtt cttttctctc
 961 ttcctctcac cttgtccctt gtcagttcca aacagacaaa acagataaac aaacaagccc
1021 cctgccctcc tctccctccc actgttaagg acccttttaa gcatgtgatg ttgtcttagc
1081 atggtacctg ctgggtgttt ttttttaaaa ggccattttg gggggttatt tatttttaa
```

Figure 19

```
1141 gaaaaaaagc tgcaaaaatt atatattgca aggtgtgatg gtctggcttg ggtgaatttc 1201 aggggaaatg aggaaaagaa aaaaggaaag aaattttaaa gccaattctc atccttctcc 1261 tcctcctcct tcccgcctct ttccttaggc cttttgcatt gaaaatgcac caggggaggt 1321 tagtgagggg gaagtcattt taaggagaac aaagctatga agttcttttg tattattgtt 1381 ggggggggtg tgggaggaga ggggcgaag acagcagaca aagctaaatg catctggaga 1441 gcctctcaga gctgttcagt ttgaggagcc aaaagaaaat caaaatgaac tttcagttca 1501 gagaggcagt ctataggtag aatctctccc caccectatc gtggttattg tgtttttgga 1561 ctgaatttac ttgattattg taaaacttgc aataaagaat tttagtgtcg atgtgaaatg 1621 ccccgtgatc aataataaac cagtggatgt gaattagttt taaaaaaaaa aaaaaaaaa 1681 aaaaa
```

MVMSSYMVNSKYVDPKFPPCEEYLQGGYLGEQGADYYGGGAQGADFQPPGLYPRPDFGEQP
FGGSGPGPGSALPARGHGQEPGGPGGHYAAPGEPCPAPPAPPPAPLPGARAYSQSDPKQPPS
GTALKQPAVVYPWMKKVHVNSVNPNYTGGEPKRSRTAYTRQQVLELEKEFHFNRYLTRRRRIEI
AHTLCLSERQIKIWFQNRRMKWKKDHKLPNTKGRSSSSSSSSSCSSSVAPSQHLQPMAKDHHT
DLTTL

B

```
   1 cattaatatc tggcaggggc tctcaaatgt gccatagcaa gctacttgat tacacgtatg
  61 ttatttagtt aaatttgtga aaattatgag atgctcacca acccggtgat aaacttgctc
 121 cctcgccatt ggctggcctg gtcacatggc tgcccaactt tattcagttg acagcaagta
 181 ggagggccct atggaaggag aaaaaaagac aacacgagaa aaattagtat tttctacctt
 241 ctgaaattaa tggtcatgag ttcgtatatg gtgaactcca agtatgtgga ccccaagttc
 301 cctccgtgcg aggagtattt gcagggcggc tacctaggcg agcagggcgc cgactactac
 361 ggcggcggcg cgcagggcgc agacttccag ccccggggc tctacccacg cccgacttc
 421 ggtgagcagc ctttcggagg cagcggcccc gggcctggct cggcgctgcc tgcgcgggt
 481 cacggacaag agccaggcgg ccccggcggt cactacgccg ctccaggaga gccttgccca
 541 gctccccgg cgcctccgcc ggcgccctg cctggcgccc gggcctacag tcagtccgac
 601 cccaagcagc cgccctccgg gacggcactc aagcagccgg ccgtggtcta ccctggatg
 661 aagaaggtgc acgtgaattc ggtgaacccc aactacaccg tggggaacc caagcggtcc
 721 cgaacggcct acacccggca gcaagtccta gaactggaaa agaatttca ttttaacagg
 781 tatctgacaa ggcgccgtcg gattgaaatc gctcacaccc tgtgtctgtc ggagcgccag
 841 atcaagatct ggttccagaa ccggaggatg aagtggaaaa agatcataa gctgcccaac
 901 actaaaggca ggtcatcgtc ctcatcttcc tcctcatctt gctcctcctc agtcgccccc
 961 agccagcatt tacagccgat ggccaaagac caccacacgg acctgacgac cttatagaag
1021 tggggaccct gggcccatct ctccctgcgc accaggctga ccgaagctg cggggcagg
1081 ccgggcctgc tgtcacctcg ctgggctcta aggtactgtg ggtggacct gggacaagca
1141 ggccgccctc ggactaggtt agcatcctgc ccgagggcag cccctccct agagcgggat
1201 ggggatggga gggggggcgg gattctctct ctaagtatat tatatggcag gagctactga
1261 gaacataaaa tcttggcgag tcattaaact tatgaaaa
```

Figure 20

```
CLUSTAL W (1.83) multiple sequence alignment

HOXA4           MTMSSFLINSNYIEPKFPPFEEYAQHSGSGGADGGPGGGPGYQQPPAPPTQHLPLQQPQL 60
HOXB4           MAMSSFLINSNYVDPKFPPCEEYSQ------------------------SDYLPSD---- 32
HOXC4           MIMSSYLMDSNYIDPKFPPCEEYSQ------------------------NSYIPEHSP-- 34
                * ***:*::***::***** ***:*                        ..::*   .

HOXA4           PHAGGGREPPASYYAPRTAREPAYPAAALYPAHGAADTAYPYGYRGGASPGRPPQPEQPP 120
HOXB4           -HSPG-------YYAGGQRRESSFQPEAGFGRRAACTVQR---YAACRDPGPPPPPPPPP 81
HOXC4           ----------EYYGRTRESGFQHHHQELYPPPPPRPSYPERQYSCTSLQGPGNSRGHGP 83
                      **.          .   :    .       *      *              *

HOXA4           AQAKGPAHGLHASHVLQPQPPPPLQPRAVPPAAPRRCEAAPATPGVPAGGSAPACPLLLA 180
HOXB4           PPPPPPG--------LSPRAPAPPPAGALLPEPGQRCEAVSSSP------PPPPCAQNPL 127
HOXC4           AQAGHHH---------------PEKSQSLCEPAPLSGASASPSP------APPACSQPAP 122
                 . .           *  .::   .      :....:*       ..*.*.

HOXA4           DKSPLGLKGKEPVVYPWMKKIHVSAVNPSYNGGEPKRSRTAYTRQQVLELEKEFHFNRYL 240
HOXB4           HPSPSHSACKEPVVYPWMRKVHVSTVNPNYAGGEPKRSRTAYTRQQVLELEKEFHYNRYL 187
HOXC4           D-HPSSAASKQPIVYPWMKKIHVSTVNPSYNGGEPKRSRTAYTRQQVLELEKEFHYNRYL 181
                 . *    *:*:*****:*:***.***.*.**************.****:****

HOXA4           TRRRRIEIAHTLCLSERQVKIWFQNRRMKWKKDHKLPNTKMRSSNSASASAGPPGKAQTQ 300
HOXB4           TRRRRVEIAHALCLSERQIKIWFQNRRMKWKKDHKLPNTKIRSGGAAGSAGGPPGRPNGG 247
HOXC4           TRRRRIEIAHSLCLSERQIKIWFQNRRMKWKKDHRLPNTKVRSAPPAGAAPSTLSAATPG 241
                *****:****:*******:***************:*****:**. .*..:: ..  .

HOXA4           SPHLHPHPHPSTSTPVPSSI--- 320
HOXB4           PRAL------------------- 251
HOXC4           TSEDHSQSATPPEQQRAEDITRL 264
                .
```

Figure 21

```
atggctgggtacggccgcaagaaacgccgccagcgccgccgcggtatggctatgagttct
 M   A   G   Y   G   R   K   K   R   R   Q   R   R   R   G   M   A   M   S   S
tttttgatcaactcaaactatgtcgaccccaagttccctccatgcgaggaatattcacag
 F   L   I   N   S   N   Y   V   D   P   K   F   P   P   C   E   E   Y   S   Q
agcgattacctacccagcgaccactcgcccgggtactacgccggcggccagaggcgagag
 S   D   Y   L   P   S   D   H   S   P   G   Y   Y   A   G   G   Q   R   R   E
agcagcttccagccggaggcgggcttcggcggcgcgcggcgtgcaccgtgcagcgctac
 S   S   F   Q   P   E   A   G   F   G   R   R   A   A   C   T   V   Q   R   Y
gcggcctgccgggaccctgggccccgccgcctccgccaccaccccgccgccccgcca
 A   A   C   R   D   P   G   P   P   P   P   P   P   P   P   P   P   P
ccgcccggtctgtcccctcgggctcctgcgccgccacccgccggggccctcctcccggag
 P   P   G   L   S   P   R   A   P   A   P   P   P   A   G   A   L   L   P   E
cccggccagcgctgcgaggcggtcagcagcagccccccgccgcctccctgcgcccagaac
 P   G   Q   R   C   E   A   V   S   S   S   P   P   P   P   C   A   Q   N
cccctgcaccccagcccgtcccactccgcgtgcaaagagcccgtcgtctaccctggatg
 P   L   H   P   S   P   S   H   S   A   C   K   E   P   V   V   Y   P   W   M
cgcaaagttcacgtgagcacggtaaaccccaattacgccggcggggagcccaagcgctct
 R   K   V   H   V   S   T   V   N   P   N   Y   A   G   G   E   P   K   R   S
cggaccgcctacacgcgccagcaggtcttggagctggagaaggaatttcactacaaccgc
 R   T   A   Y   T   R   Q   Q   V   L   E   L   E   K   E   F   H   Y   N   R
tacctgacacggcgccggagggtggagatcgcccacgcgctctgcctctccgagcgccag
 Y   L   T   R   R   R   V   E   I   A   H   A   L   C   L   S   E   R   Q
atcaagatctggttccagaaccggcgcatgaagtggaaaaagaccacaagttgcccaac
 I   K   I   W   F   Q   N   R   R   M   K   W   K   K   D   H   K   L   P   N
accaagatccgctcgggtggtgcggcaggctcagccggagggccccctggccggcccaat
 T   K   I   R   S   G   G   A   A   G   S   A   G   G   P   P   G   R   P   N
ggaggccccgcgcgctctag
 G   G   P   R   A   L
```

Figure 22

```
atggctgggtacggccgcaagaaacgccgccagcgccgccgcggtatggctatgagttct
 M   A   G   Y   G   R   K   K   R   R   Q   R   R   R   G   M   A   M   S   S
tttgcgatcaactcaaactatgtcgaccccaagttccctccatgcgaggaatattcacag
 F   A   I   N   S   N   Y   V   D   P   K   F   P   P   C   E   E   Y   S   Q
agcgattacctacccagcgaccactcgcccgggtactacgccggcggccagaggcgagag
 S   D   Y   L   P   S   D   H   S   P   G   Y   Y   A   G   G   Q   R   R   E
agcagcttccagccggaggcgggcttcggcggcgcgcggcgtgcaccgtgcagcgctac
 S   S   F   Q   P   E   A   G   F   G   R   R   A   C   T   V   Q   R   Y
gcggcctgccgggaccctgggccccgccgcctccgccaccaccccgccgcccccgcca
 A   A   C   R   D   P   G   P   P   P   P   P   P   P   P   P   P   P
ccgcccggtctgtcccctcgggctcctgcgccgccaccgccggggccctcctcccggag
 P   P   G   L   S   P   R   A   P   A   P   P   A   G   A   L   L   P   E
cccggccagcgctgcgaggcggtcagcagcagccccccgccgcctccctgcgcccagaac
 P   G   Q   R   C   E   A   V   S   S   S   P   P   P   P   C   A   Q   N
cccctgcaccccagcccgtcccactcgcgtgcaaagagcccgtcgtctaccctggatg
 P   L   H   P   S   P   S   H   S   A   C   K   E   P   V   V   Y   P   W   M
cgcaaagttcacgtgagcacggtaaaccccaattacgccggcggggagcccaagcgctct
 R   K   V   H   V   S   T   V   N   P   N   Y   A   G   G   E   P   K   R   S
cggaccgcctacacgcgccagcaggtcttggagctggagaaggaatttcactacaaccgc
 R   T   A   Y   T   R   Q   Q   V   L   E   L   E   K   E   F   H   Y   N   R
tacctgacacggcgccggagggtggagatcgcccacgcgctctgcctctccgagcgccag
 Y   L   T   R   R   R   R   V   E   I   A   H   A   L   C   L   S   E   R   Q
atcaagatctggttccagaaccggcgcatgaagtggaaaaagaccacaagttgcccaac
 I   K   I   W   F   Q   N   R   R   M   K   W   K   K   D   H   K   L   P   N
accaagatccgctcgggtggtgcggcaggctcagccggagggcccctggccggcccaat
 T   K   I   R   S   G   G   A   A   G   S   A   G   G   P   P   G   R   P   N
ggaggcccccgcgcgctctag
 G   G   P   R   A   L
```

Figure 23A

```
atggctgggtacggccgcaagaaacgccgccagcgccgccgcggtatggctatgagttct
 M   A   G   Y   G   R   K   K   R   R   Q   R   R   R   G   M   A   M   S   S
tttttgatcaactcaaactatgtcgaccccaagttccctccatgcgaggaagcttcacag
 F   L   I   N   S   N   Y   V   D   P   K   F   P   P   C   E   E   A   S   Q
agcgattacctacccagcgaccactcgcccgggtactacgccggcggccagaggcgagag
 S   D   Y   L   P   S   D   H   S   P   G   Y   Y   A   G   G   Q   R   R   E
agcagcttccagccggaggcgggcttcgggcggcgcggcgtgcaccgtgcagcgctac
 S   S   F   Q   P   E   A   G   F   G   R   R   A   A   C   T   V   Q   R   Y
gcggcctgccgggaccctgggccccgccgcctccgccaccaccccgccgccccgcca
 A   A   C   R   D   P   G   P   P   P   P   P   P   P   P   P   P   P
ccgcccggtctgtccctcgggctcctgcgccgccacccgcggggccctcctcccggag
 P   P   G   L   S   P   R   A   P   P   P   A   G   A   L   L   P   E
cccggccagcgctgcgaggcggtcagcagcagccccccgccgcctccctgcgcccagaac
 P   G   Q   R   C   E   A   V   S   S   P   P   P   P   P   C   A   Q   N
cccctgcaccccagcccgtcccactccgcgtgcaaagagcccgtcgtctaccctggatg
 P   L   H   P   S   P   S   H   S   A   C   K   E   P   V   V   Y   P   W   M
cgcaaagttcacgtgagcacggtaaaccccaattacgccggcggggagcccaagcgctct
 R   K   V   H   V   S   T   V   N   P   N   Y   A   G   G   E   P   K   R   S
cggaccgcctacacgcgccagcaggtcttggagctggagaaggaatttcactacaaccgc
 R   T   A   Y   T   R   Q   Q   V   L   E   L   E   K   E   F   H   Y   N   R
tacctgacacggcgccggagggtggagatcgcccacgcgctctgcctctccgagcgccag
 Y   L   T   R   R   R   V   E   I   A   H   A   L   C   S   E   R   Q
atcaagatctggttccagaaccggcgcatgaagtggaaaaagaccacaagttgcccaac
 I   K   I   W   F   Q   N   R   R   M   K   W   K   K   D   H   K   L   P   N
accaagatccgctcgggtggtgcggcaggctcagccggagggcccctggccggcccaat
 T   K   I   R   S   G   G   A   A   G   S   A   G   G   P   P   G   R   P   N
ggaggccccgcgcgctctag
 G   G   P   R   A   L
```

Figure 23B

```
atggctgggtacggccgcaagaaacgccgccagcgccgccgcggtatggctatgagttct
 M   A   G   Y   G   R   K   K   R   R   Q   R   R   R   G   M   A   M   S   S
tttttgatcaactcaaactatgtcgaccccaagttccctccatgcgaggaatattcacag
 F   L   I   N   S   N   Y   V   D   P   K   F   P   P   C   E   E   Y   S   Q
agcgatgccctacccagcgaccactcgcccgggtactacgccggcggccagaggcgagag
 S   D   A   L   P   S   D   H   S   P   G   Y   Y   A   G   G   Q   R   R   E
agcagcttccagccggaggcgggcttcggcggcgcgcggcgtgcaccgtgcagcgctac
 S   S   F   Q   P   E   A   G   F   G   R   R   A   A   C   T   V   Q   R   Y
gcggcctgccgggaccctgggccccgccgcctccgccaccaccccgccgccccgcca
 A   A   C   R   D   P   G   P   P   P   P   P   P   P   P   P   P   P
ccgcccggtctgtccctcgggctcctgcgccgccacccgccggggcccctcctcccggag
 P   P   G   L   S   P   R   A   P   P   P   A   G   A   L   L   P   E
cccggccagcgctgcgaggcggtcagcagcagccccccgccgcctccctgcgcccagaac
 P   G   Q   R   C   E   A   V   S   S   S   P   P   P   P   C   A   Q   N
cccctgcaccccagcccgtcccactccgcgtgcaaagagcccgtcgtctacccctggatg
 P   L   H   P   S   P   S   H   S   A   C   K   E   P   V   V   Y   P   W   M
cgcaaagttcacgtgagcacggtaaaccccaattacgccggcggggagcccaagcgctct
 R   K   V   H   V   S   T   V   N   P   N   Y   A   G   G   E   P   K   R   S
cggaccgcctacacgcgccagcaggtcttggagctggagaaggaatttcactacaaccgc
 R   T   A   Y   T   R   Q   Q   V   L   E   L   E   K   E   F   H   Y   N   R
tacctgacacggcgccggagggtggagatcgcccacgcgctctgcctctccgagcgccag
 Y   L   T   R   R   R   R   V   E   I   A   H   A   L   C   S   E   R   Q
atcaagatctggttccagaaccggcgcatgaagtggaaaaagaccacaagttgcccaac
 I   K   I   W   F   Q   N   R   R   M   K   W   K   K   D   H   K   L   P   N
accaagatccgctcgggtggtgcggcaggctcagccggagggccccctggccggcccaat
 T   K   I   R   S   G   G   A   A   G   S   A   G   G   P   P   G   R   P   N
ggaggccccgcgcgctctag
 G   G   P   R   A   L
```

Figure 23C

```
atggctgggtacggccgcaagaaacgccgccagcgccgccgcggtatggctatgagttct
 M   A  G  Y  G  R  K  K  R  R  Q  R  R  R  G  M  A  M  S  S
gctttgatcaactcaaactatgtcgaccccaagttccctccatgcgaggaatattcacag
 A   L  I  N  S  N  Y  V  D  P  K  F  P  P  C  E  E  Y  S  Q
agcgattacctacccagcgaccactcgcccggtactacgccggcggccagaggcgagag
 S   D  Y  L  P  S  D  H  S  P  G  Y  Y  A  G  G  Q  R  R  E
agcagcttccagccggaggcgggcttcgggcggcgcgcggcgtgcaccgtgcagcgctac
 S   S  F  Q  P  E  A  G  F  G  R  R  A  A  C  T  V  Q  R  Y
gcggcctgccgggaccctgggccccgccgcctccgccaccaccccgccgccccgcca
 A   A  C  R  D  P  G  P  P  P  P  P  P  P  P  P  P  P  P
ccgcccggtctgtcccctcgggctcctgcgccgccacccgccggggccctcctcccggag
 P   P  G  L  S  P  R  A  P  P  P  A  G  A  L  L  P  E
cccggccagcgctgcgaggcggtcagcagcagccccccgccgcctccctgcgcccagaac
 P   G  Q  R  C  E  A  V  S  S  S  P  P  P  P  C  A  Q  N
cccctgcaccccagcccgtcccactccgcgtgcaaagagcccgtcgtctaccctggatg
 P   L  H  P  S  P  S  H  S  A  C  K  E  P  V  V  Y  P  W  M
cgcaaagttcacgtgagcacggtaaaccccaattacgccggcggggagcccaagcgctct
 R   K  V  H  V  S  T  V  N  P  N  Y  A  G  G  E  P  K  R  S
cggaccgcctacacgcgccagcaggtcttggagctggagaaggaatttcactacaaccgc
 R   T  A  Y  T  R  Q  Q  V  L  E  L  E  K  E  F  H  Y  N  R
tacctgacacggcgccggagggtggagatcgcccacgcgctctgcctctccgagcgccag
 Y   L  T  R  R  R  V  E  I  A  H  A  L  C  L  S  E  R  Q
atcaagatctggttccagaaccggcgcatgaagtggaaaaagaccacaagttgcccaac
 I   K  I  W  F  Q  N  R  R  M  K  W  K  K  D  H  K  L  P  N
accaagatccgctcgggtggtgcggcaggctcagccggagggccccctggccggcccaat
 T   K  I  R  S  G  G  A  A  G  S  A  G  G  P  P  G  R  P  N
ggaggccccgcgcgctctag
 G   G  P  R  A  L
```

Figure 23D

SEQUENCE LISTING

<160> NUMBER OF SEQ ID NOS: 66

<210> SEQ ID NO 1
<211> LENGTH: 756
<212> TYPE: DNA
<213> ORGANISM: homo sapiens

<400> SEQUENCE: 1
atggctatga gttctttttt gatcaactca aactatgtcg accccaagtt ccctccatgc    60
gaggaatatt cacagagcga ttacctaccc agcgaccact cgcccgggta ctacgccggc   120
ggccagaggc gagagagcag cttccagccg gaggcgggct cgggcggcg cgcggcgtgc    180

```
accgtgcagc gctacgcggc ctgccgggac cctgggcccc cgccgcctcc gccaccaccc    240
ccgccgcccc cgccaccgcc cggtctgtcc cctcgggctc ctgcgccgcc accgccgggg    300
gccctcctcc cggagcccgg ccagcgctgc gaggcggtca gcagcagccc ccgccgcct     360 ccctgcgccc agaaccccct gcaccccagc ccgtcccact ccgcgtgcaa agagcccgtc    420
gtctacccct ggatgcgcaa agttcacgtg agcacggtaa accccaatta cgccggcggg    480
gagcccaagc gctctcggac cgcctacacg cgccagcagg tcttggagct ggagaaggaa    540
tttcactaca accgctacct gacacggcgc cggagggtgg agatcgccca cgcgctctgc    600
ctctccgagc gccagatcaa gatctggttc cagaaccggc gcatgaagtg gaaaaagac    660 cacaagttgc caacaccaa gatcgctcg ggtggtgcgg caggctcagc cggagggccc    720
cctggccggc caatggagg cccccgcgcg ctctag                              756

<210> SEQ ID NO 2
<211> LENGTH: 251
<212> TYPE: PRT
<213> ORGANISM: homo sapiens

<400> SEQUENCE: 2

Met Ala Met Ser Ser Phe Leu Ile Asn Ser Asn Tyr Val Asp Pro Lys
1               5                   10                  15

Phe Pro Pro Cys Glu Glu Tyr Ser Gln Ser Asp Tyr Leu Pro Ser Asp
            20                  25                  30

His Ser Pro Gly Tyr Tyr Ala Gly Gly Gln Arg Arg Glu Ser Ser Phe
        35                  40                  45

Gln Pro Glu Ala Gly Phe Gly Arg Arg Ala Ala Cys Thr Val Gln Arg
    50                  55                  60

Tyr Ala Ala Cys Arg Asp Pro Gly Pro Pro Pro Pro Pro Pro Pro Pro
65                  70                  75                  80

Pro Pro Pro Pro Pro Pro Gly Leu Ser Pro Arg Ala Pro Ala Pro
                85                  90                  95

Pro Pro Ala Gly Ala Leu Leu Pro Glu Pro Gly Gln Arg Cys Glu Ala
            100                 105                 110

Val Ser Ser Ser Pro Pro Pro Cys Ala Gln Asn Pro Leu His
            115                 120                 125

Pro Ser Pro Ser His Ser Ala Cys Lys Glu Pro Val Val Tyr Pro Trp
    130                 135                 140

Met Arg Lys Val His Val Ser Thr Val Asn Pro Asn Tyr Ala Gly Gly
145                 150                 155                 160

Glu Pro Lys Arg Ser Arg Thr Ala Tyr Thr Arg Gln Gln Val Leu Glu
            165                 170                 175

Leu Glu Lys Glu Phe His Tyr Asn Arg Tyr Leu Thr Arg Arg Arg Arg
        180                 185                 190

Val Glu Ile Ala His Ala Leu Cys Leu Ser Glu Arg Gln Ile Lys Ile
    195                 200                 205

Trp Phe Gln Asn Arg Arg Met Lys Trp Lys Lys Asp His Lys Leu Pro
    210                 215                 220

Asn Thr Lys Ile Arg Ser Gly Gly Ala Ala Gly Ser Ala Gly Gly Pro
225                 230                 235                 240

Pro Gly Arg Pro Asn Gly Gly Pro Arg Ala Leu
            245                 250

<210> SEQ ID NO 3
<211> LENGTH: 654
```

-continued

```
<212> TYPE: DNA
<213> ORGANISM: homo sapiens

<400> SEQUENCE: 3
atggggtact acgccggcgg ccagaggcga gagagcagct tccagccgga ggcgggcttc      60
gggcggcgcg cggcgtgcac cgtgcagcgc tacgcggcct gccgggaccc tgggcccccg     120
ccgcctccgc caccacccc cgccgccccg ccaccgcccg gtctgtcccc tcgggctcct     180
gcgccgccac ccgccggggc cctcctcccg gagcccggcc agcgctgcga ggcggtcagc     240
agcagccccc cgccgcctcc ctgcgcccag aacccctgc acccagccc gtcccactcc       300
gcgtgcaaag agcccgtcgt ctaccctgg atgcgcaaag ttcacgtgag cacggtaaac      360
cccaattacg ccggcgggga gcccaagcgc tctcggaccg cctacacgcg ccagcaggtc     420
ttggagctgg agaaggaatt tcactacaac cgctacctga cggcgccg gagggtggag       480
atcgcccacg cgctctgcct ctccgagcgc cagatcaaga tctggttcca gaaccggcgc     540
atgaagtgga aaaagacca caagttgccc aacaccaaga tccgctcggg tggtgcggca     600
ggctcagccg agggcccccc tggccggccc aatggaggcc cccgcgcgct ctag           654

<210> SEQ ID NO 4
<211> LENGTH: 217
<212> TYPE: PRT
<213> ORGANISM: homo sapiens

<400> SEQUENCE: 4

Met Gly Tyr Tyr Ala Gly Gly Gln Arg Arg Glu Ser Ser Phe Gln Pro
1               5                   10                  15

Glu Ala Gly Phe Gly Arg Arg Ala Ala Cys Thr Val Gln Arg Tyr Ala
            20                  25                  30

Ala Cys Arg Asp Pro Gly Pro Pro Pro Pro Pro Pro Pro Pro Pro Pro
        35                  40                  45

Pro Pro Pro Pro Pro Gly Leu Ser Pro Arg Ala Pro Ala Pro Pro Pro
    50                  55                  60

Ala Gly Ala Leu Leu Pro Glu Pro Gly Gln Arg Cys Glu Ala Val Ser
65                  70                  75                  80

Ser Ser Pro Pro Pro Pro Cys Ala Gln Asn Pro Leu His Pro Ser
                85                  90                  95

Pro Ser His Ser Ala Cys Lys Glu Pro Val Val Tyr Pro Trp Met Arg
            100                 105                 110

Lys Val His Val Ser Thr Val Asn Pro Asn Tyr Ala Gly Gly Glu Pro
        115                 120                 125

Lys Arg Ser Arg Thr Ala Tyr Thr Arg Gln Gln Val Leu Glu Leu Glu
    130                 135                 140

Lys Glu Phe His Tyr Asn Arg Tyr Leu Thr Arg Arg Arg Val Glu
145                 150                 155                 160

Ile Ala His Ala Leu Cys Leu Ser Glu Arg Gln Ile Lys Ile Trp Phe
                165                 170                 175

Gln Asn Arg Arg Met Lys Trp Lys Lys Asp His Lys Leu Pro Asn Thr
            180                 185                 190

Lys Ile Arg Ser Gly Gly Ala Ala Gly Ser Ala Gly Gly Pro Pro Gly
        195                 200                 205

Arg Pro Asn Gly Gly Pro Arg Ala Leu
    210                 215

<210> SEQ ID NO 5
<211> LENGTH: 35
```

```
<212> TYPE: PRT
<213> ORGANISM: artificial
<220> FEATURE:
<223> OTHER INFORMATION: hHoxb4 protein N-terminal domain

<400> SEQUENCE: 5

Met Ala Met Ser Ser Phe Leu Ile Asn Ser Asn Tyr Val Asp Pro Lys
1               5                   10                  15

Phe Pro Pro Cys Glu Glu Tyr Ser Gln Ser Asp Tyr Leu Pro Ser Asp
            20                  25                  30

His Ser Pro
        35

<210> SEQ ID NO 6
<211> LENGTH: 13
<212> TYPE: PRT
<213> ORGANISM: artificial
<220> FEATURE:
<223> OTHER INFORMATION: TAT fragment
<220> FEATURE:
<221> NAME/KEY: MISC_FEATURE
<222> LOCATION: (1)..(1)
<223> OTHER INFORMATION: Xaa = Gly or absent
<220> FEATURE:
<221> NAME/KEY: MISC_FEATURE
<222> LOCATION: (13)..(13)
<223> OTHER INFORMATION: Xaa = Gly or absent

<400> SEQUENCE: 6

Xaa Tyr Gly Arg Lys Lys Arg Arg Gln Arg Arg Arg Xaa
1               5                   10

<210> SEQ ID NO 7
<211> LENGTH: 801
<212> TYPE: DNA
<213> ORGANISM: artificial
<220> FEATURE:
<223> OTHER INFORMATION: wt TAT-h Hoxb4

<400> SEQUENCE: 7
atggctgggt acggccgcaa gaaacgccgc cagcgccgcc gcggtatggc tatgagttct        60
tttttgatca actcaaacta tgtcgacccc aagttccctc catgcgagga atattcacag       120
agcgattacc tacccagcga ccactcgccc gggtactacg ccggcggcca gaggcgagag       180
agcagcttcc agccggaggc gggcttcggg cggcgcgcgg cgtgcaccgt gcagcgctac       240
gcggcctgcc gggaccctgg gccccgcgcc cctccgccac cacccccgcc gccccgcca       300 ccgcccggtc tgtccctcg gctcctgcg ccgccaccg ccggggccct cctcccggag         360
cccggccagc gctgcgaggc ggtcagcagc agccccccgc cgcctccctg cgcccagaac       420
cccctgcacc ccagcccgtc ccactccgcg tgcaaagagc ccgtcgtcta cccctggatg       480
cgcaaagttc acgtgagcac ggtaaacccc aattacgccg gcgggagcc caagcgctct       540 cggaccgcct acacgcgcca gcaggtcttg gagctggaga aggaatttca ctacaaccgc       600
tacctgacac ggcgccggag ggtggagatc gcccacgcgc tctgcctctc cgagcgccag       660
atcaagatct ggttccagaa ccggcgcatg aagtggaaaa agaccacaa gttgcccaac        720 accaagatcc gctcgggtgg tgcggcaggc tcagccggag gccccctgg ccggcccaat        780 ggaggccccc gcgcgctcta g                                                 801

<210> SEQ ID NO 8
<211> LENGTH: 266
<212> TYPE: PRT
<213> ORGANISM: artificial
```

<220> FEATURE:
<223> OTHER INFORMATION: wt TAT-hHoxb4

<400> SEQUENCE: 8

```
Met Ala Gly Tyr Gly Arg Lys Lys Arg Arg Gln Arg Arg Gly Met
1               5                   10                  15

Ala Met Ser Ser Phe Leu Ile Asn Ser Asn Tyr Val Asp Pro Lys Phe
            20                  25                  30

Pro Pro Cys Glu Glu Tyr Ser Gln Ser Asp Tyr Leu Pro Ser Asp His
            35                  40                  45

Ser Pro Gly Tyr Tyr Ala Gly Gly Gln Arg Arg Glu Ser Ser Phe Gln
    50                  55                  60

Pro Glu Ala Gly Phe Gly Arg Arg Ala Ala Cys Thr Val Gln Arg Tyr
65                  70                  75                  80

Ala Ala Cys Arg Asp Pro Gly Pro Pro Pro Pro Pro Pro Pro
                85                  90                  95

Pro Pro Pro Pro Pro Gly Leu Ser Pro Arg Ala Pro Ala Pro Pro
            100                 105                 110

Pro Ala Gly Ala Leu Leu Pro Glu Pro Gly Gln Arg Cys Glu Ala Val
        115                 120                 125

Ser Ser Ser Pro Pro Pro Pro Cys Ala Gln Asn Pro Leu His Pro
    130                 135                 140

Ser Pro Ser His Ser Ala Cys Lys Glu Pro Val Val Tyr Pro Trp Met
145                 150                 155                 160

Arg Lys Val His Val Ser Thr Val Asn Pro Asn Tyr Ala Gly Gly Glu
                165                 170                 175

Pro Lys Arg Ser Arg Thr Ala Tyr Thr Arg Gln Gln Val Leu Glu Leu
            180                 185                 190

Glu Lys Glu Phe His Tyr Asn Arg Tyr Leu Thr Arg Arg Arg Val
        195                 200                 205

Glu Ile Ala His Ala Leu Cys Leu Ser Glu Arg Gln Ile Lys Ile Trp
    210                 215                 220

Phe Gln Asn Arg Arg Met Lys Trp Lys Lys Asp His Lys Leu Pro Asn
225                 230                 235                 240

Thr Lys Ile Arg Ser Gly Gly Ala Ala Gly Ser Ala Gly Gly Pro Pro
                245                 250                 255

Gly Arg Pro Asn Gly Gly Pro Arg Ala Leu
            260                 265
```

<210> SEQ ID NO 9
<211> LENGTH: 801
<212> TYPE: DNA
<213> ORGANISM: artificial
<220> FEATURE:
<223> OTHER INFORMATION: mutant L7A TAT-Hoxb4

<400> SEQUENCE: 9

```
atggctgggt acggccgcaa gaaacgccgc cagcgccgcc gcggtatggc tatgagttct      60
tttgcgatca actcaaacta tgtcgacccc aagttccctc catgcgagga atattcacag     120
agcgattacc tacccagcga ccactcgccc gggtactacg ccggcggcca gaggcgagag     180
agcagcttcc agccggaggc gggcttcggg cggcgcgcgg cgtgcaccgt gcagcgctac     240
gcggcctgcc gggaccctgg gcccccgccg cctccgccac cccccgcc gccccgcca        300 ccgcccggtc tgtcccctcg ggctcctgcg ccgccaccg ccggggccct cctcccggag      360
cccggccagc gctgcgaggc ggtcagcagc agccccccgc cgcctccctg cgcccagaac     420
```

-continued

```
cccctgcacc ccagcccgtc ccactccgcg tgcaaagagc ccgtcgtcta cccctggatg    480
cgcaaagttc acgtgagcac ggtaaacccc aattacgccg gcggggagcc caagcgctct    540
cggaccgcct acacgcgcca gcaggtcttg gagctggaga aggaatttca ctacaaccgc    600
tacctgacac ggcgcggag ggtggagatc gcccacgcgc tctgcctctc cgagcgccag    660
atcaagatct ggttccagaa ccggcgcatg aagtggaaaa agaccacaa gttgcccaac    720 accaagatcc gctcgggtgg tgcggcaggc tcagccggag ggccccctgg ccggcccaat    780
ggaggccccc gcgcgctcta g                                              801
```

<210> SEQ ID NO 10
<211> LENGTH: 266
<212> TYPE: PRT
<213> ORGANISM: artificial
<220> FEATURE:
<223> OTHER INFORMATION: mutant L7A TAT-Hoxb4

<400> SEQUENCE: 10

```
Met Ala Gly Tyr Gly Arg Lys Lys Arg Arg Gln Arg Arg Gly Met
1               5                   10                  15

Ala Met Ser Ser Phe Ala Ile Asn Ser Asn Tyr Val Asp Pro Lys Phe
            20                  25                  30

Pro Pro Cys Glu Glu Tyr Ser Gln Ser Asp Tyr Leu Pro Ser Asp His
        35                  40                  45

Ser Pro Gly Tyr Tyr Ala Gly Gly Gln Arg Arg Glu Ser Ser Phe Gln
    50                  55                  60

Pro Glu Ala Gly Phe Gly Arg Arg Ala Ala Cys Thr Val Gln Arg Tyr
65                  70                  75                  80

Ala Ala Cys Arg Asp Pro Gly Pro Pro Pro Pro Pro Pro Pro Pro Pro
                85                  90                  95

Pro Pro Pro Pro Pro Pro Gly Leu Ser Pro Arg Ala Pro Ala Pro Pro
            100                 105                 110

Pro Ala Gly Ala Leu Leu Pro Glu Pro Gly Gln Arg Cys Glu Ala Val
        115                 120                 125

Ser Ser Ser Pro Pro Pro Pro Cys Ala Gln Asn Pro Leu His Pro
    130                 135                 140

Ser Pro Ser His Ser Ala Cys Lys Glu Pro Val Val Tyr Pro Trp Met
145                 150                 155                 160

Arg Lys Val His Val Ser Thr Val Asn Pro Asn Tyr Ala Gly Gly Glu
                165                 170                 175

Pro Lys Arg Ser Arg Thr Ala Tyr Thr Arg Gln Val Leu Glu Leu
            180                 185                 190

Glu Lys Glu Phe His Tyr Asn Arg Tyr Leu Thr Arg Arg Arg Arg Val
        195                 200                 205

Glu Ile Ala His Ala Leu Cys Leu Ser Glu Arg Gln Ile Lys Ile Trp
    210                 215                 220

Phe Gln Asn Arg Arg Met Lys Trp Lys Lys Asp His Lys Leu Pro Asn
225                 230                 235                 240

Thr Lys Ile Arg Ser Gly Gly Ala Ala Gly Ser Ala Gly Gly Pro Pro
                245                 250                 255

Gly Arg Pro Asn Gly Gly Pro Arg Ala Leu
            260                 265
```

<210> SEQ ID NO 11
<211> LENGTH: 801
<212> TYPE: DNA
<213> ORGANISM: artificial

<220> FEATURE:
<223> OTHER INFORMATION: mutant Y23A TAT-Hoxb4

<400> SEQUENCE: 11

```
atggctgggt acggccgcaa gaaacgccgc cagcgccgcc gcggtatggc tatgagttct      60
tttttgatca actcaaacta tgtcgacccc aagttccctc catgcgagga agcttcacag     120
agcgattacc tacccagcga ccactcgccc gggtactacg ccggcggcca gaggcgagag     180
agcagcttcc agccggaggc gggcttcggg cggcgcgcgg cgtgcaccgt gcagcgctac     240
gcggcctgcc gggaccctgg gcccccgccg cctccgccac caccccgcc gccccgcca      300
ccgcccggtc tgtcccctcg ggctcctgcg ccgccacccg ccggggccct cctcccggag     360
cccggccagc gctgcgaggc ggtcagcagc agccccccgc cgcctccctg cgcccagaac     420
cccctgcacc ccagcccgtc ccactccgcg tgcaaagagc ccgtcgtcta cccctggatg     480
cgcaaagttc acgtgagcac ggtaaacccc aattacgccg gcggggagcc caagcgctct     540
cggaccgcct acacgcgcca gcaggtcttg gagctggaga aggaatttca ctacaaccgc     600
tacctgacac ggcgccggag ggtggagatc gcccacgcgc tctgcctctc gagcgccag     660
atcaagatct ggttccagaa ccggcgcatg aagtggaaaa aagaccacaa gttgcccaac     720
accaagatcc gctcgggtgg tgcggcaggc tcagccggag ggcccctgg ccggcccaat     780
ggaggccccc gcgcgctcta g                                               801
```

<210> SEQ ID NO 12
<211> LENGTH: 266
<212> TYPE: PRT
<213> ORGANISM: artificial
<220> FEATURE:
<223> OTHER INFORMATION: mutant Y23A TAT-Hoxb4

<400> SEQUENCE: 12

```
Met Ala Gly Tyr Gly Arg Lys Lys Arg Arg Gln Arg Arg Gly Met
1               5                   10                  15

Ala Met Ser Ser Phe Leu Ile Asn Ser Asn Tyr Val Asp Pro Lys Phe
            20                  25                  30

Pro Pro Cys Glu Glu Ala Ser Gln Ser Asp Tyr Leu Pro Ser Asp His
        35                  40                  45

Ser Pro Gly Tyr Tyr Ala Gly Gly Gln Arg Arg Glu Ser Ser Phe Gln
    50                  55                  60

Pro Glu Ala Gly Phe Gly Arg Arg Ala Ala Cys Thr Val Gln Arg Tyr
65                  70                  75                  80

Ala Ala Cys Arg Asp Pro Gly Pro Pro Pro Pro Pro Pro Pro
                85                  90                  95

Pro Pro Pro Pro Pro Pro Gly Leu Ser Pro Arg Ala Pro Ala Pro Pro
            100                 105                 110

Pro Ala Gly Ala Leu Leu Pro Glu Pro Gly Gln Arg Cys Glu Ala Val
        115                 120                 125

Ser Ser Ser Pro Pro Pro Pro Cys Ala Gln Asn Pro Leu His Pro
    130                 135                 140

Ser Pro Ser His Ser Ala Cys Lys Glu Pro Val Val Tyr Pro Trp Met
145                 150                 155                 160

Arg Lys Val His Val Ser Thr Val Asn Pro Asn Tyr Ala Gly Gly Glu
                165                 170                 175

Pro Lys Arg Ser Arg Thr Ala Tyr Thr Arg Gln Gln Val Leu Glu Leu
            180                 185                 190

Glu Lys Glu Phe His Tyr Asn Arg Tyr Leu Thr Arg Arg Arg Arg Val
```

```
                195                 200                 205
Glu Ile Ala His Ala Leu Cys Leu Ser Glu Arg Gln Ile Lys Ile Trp
        210                 215                 220

Phe Gln Asn Arg Arg Met Lys Trp Lys Lys Asp His Lys Leu Pro Asn
225                 230                 235                 240

Thr Lys Ile Arg Ser Gly Gly Ala Ala Gly Ser Ala Gly Gly Pro
                245                 250                 255

Gly Arg Pro Asn Gly Gly Pro Arg Ala Leu
            260                 265

<210> SEQ ID NO 13
<211> LENGTH: 801
<212> TYPE: DNA
<213> ORGANISM: artificial
<220> FEATURE:
<223> OTHER INFORMATION: mutant Y28A TAT-Hoxb4

<400> SEQUENCE: 13
atggctgggt acggccgcaa gaaacgccgc cagcgccgcc gcggtatggc tatgagttct      60
tttttgatca actcaaacta tgtcgacccc aagttccctc catgcgagga atattcacag     120
agcgatgccc tacccagcga ccactcgccc gggtactacg ccggcggcca gaggcgagag     180
agcagcttcc agccggaggc gggcttcggg cggcgcgcgg cgtgcaccgt gcagcgctac     240
gcggcctgcc gggaccctgg gcccccgccg cctccgccac caccccgccg ccccccgcca     300
ccgcccggtc tgtcccctcg gctcctgcgc cgccacccg ccggggccct cctcccggag      360
cccggccagc gctgcgaggc ggtcagcagc agccccccgc cgcctccctg cgcccagaac     420
cccctgcacc ccagcccgtc ccactccgcg tgcaaagagc ccgtcgtcta cccctggatg     480
cgcaaagttc acgtgagcac ggtaaacccc aattacgccg gcggggagcc caagcgctct     540
cggaccgcct acacgcgcca gcaggtcttg gagctggaga aggaatttca ctacaaccgc     600
tacctgacac ggcgccggag ggtggagatc gcccacgcgc tctgcctctc cgagcgccag     660
atcaagatct ggttccagaa ccggcgcatg aagtggaaaa agaccacaa gttgcccaac      720 accaagatcc gctcgggtgg tgcggcaggc tcagccggag ggcccctgg ccggcccaat      780 ggaggccccc gcgcgctcta g                                               801

<210> SEQ ID NO 14
<211> LENGTH: 266
<212> TYPE: PRT
<213> ORGANISM: artificial
<220> FEATURE:
<223> OTHER INFORMATION: mutant Y28A TAT-Hoxb4

<400> SEQUENCE: 14

Met Ala Gly Tyr Gly Arg Lys Lys Arg Arg Gln Arg Arg Arg Gly Met
1               5                   10                  15

Ala Met Ser Ser Phe Leu Ile Asn Ser Asn Tyr Val Asp Pro Lys Phe
            20                  25                  30

Pro Pro Cys Glu Glu Tyr Ser Gln Ser Asp Ala Leu Pro Ser Asp His
        35                  40                  45

Ser Pro Gly Tyr Tyr Ala Gly Gly Gln Arg Arg Glu Ser Ser Phe Gln
    50                  55                  60

Pro Glu Ala Gly Phe Gly Arg Arg Ala Ala Cys Thr Val Gln Arg Tyr
65                  70                  75                  80

Ala Ala Cys Arg Asp Pro Gly Pro Pro Pro Pro Pro Pro Pro
            85                  90                  95
```

```
Pro Pro Pro Pro Pro Gly Leu Ser Pro Arg Ala Pro Ala Pro Pro
            100                 105                 110

Pro Ala Gly Ala Leu Leu Pro Glu Pro Gly Gln Arg Cys Glu Ala Val
            115                 120                 125

Ser Ser Ser Pro Pro Pro Pro Cys Ala Gln Asn Pro Leu His Pro
130                 135                 140

Ser Pro Ser His Ser Ala Cys Lys Glu Pro Val Val Tyr Pro Trp Met
145                 150                 155                 160

Arg Lys Val His Val Ser Thr Val Asn Pro Asn Tyr Ala Gly Gly Glu
                165                 170                 175

Pro Lys Arg Ser Arg Thr Ala Tyr Thr Arg Gln Gln Val Leu Glu Leu
            180                 185                 190

Glu Lys Glu Phe His Tyr Asn Arg Tyr Leu Thr Arg Arg Arg Val
            195                 200                 205

Glu Ile Ala His Ala Leu Cys Leu Ser Glu Arg Gln Ile Lys Ile Trp
        210                 215                 220

Phe Gln Asn Arg Arg Met Lys Trp Lys Lys Asp His Lys Leu Pro Asn
225                 230                 235                 240

Thr Lys Ile Arg Ser Gly Gly Ala Ala Gly Ser Ala Gly Gly Pro Pro
                245                 250                 255

Gly Arg Pro Asn Gly Gly Pro Arg Ala Leu
            260                 265

<210> SEQ ID NO 15
<211> LENGTH: 801
<212> TYPE: DNA
<213> ORGANISM: artificial
<220> FEATURE:
<223> OTHER INFORMATION: mutant F6A TAT-Hoxb4

<400> SEQUENCE: 15
atggctgggt acggccgcaa gaaacgccgc cagcgccgcc gcggtatggc tatgagttct      60
gctttgatca actcaaacta tgtcgacccc aagttccctc catgcgagga atattcacag     120
agcgattacc tacccagcga ccactcgccc gggtactacg ccggcggcca gaggcgagag     180
agcagcttcc agccggaggc gggcttcggg cggcgcgcgg cgtgcaccgt gcagcgctac     240
gcggcctgcc gggaccctgg gccccgcgc cctccgccac cccccgcc gccccgcca        300 ccgcccggtc tgtcccctcg ggctcctgcg ccgccacccg cggggccct cctcccggag     360 cccggccagc gctgcgaggc ggtcagcagc agccccccgc cgcctccctg cgcccagaac     420
cccctgcacc ccagcccgtc ccactccgcg tgcaaagagc ccgtcgtcta cccctggatg     480
cgcaaagttc acgtgagcac ggtaaacccc aattacgccg gcggggagcc caagcgctct     540
cggaccgcct acacgcgcca gcaggtcttg gagctggaga aggaatttca ctacaaccgc     600
tacctgacac ggcgccggag ggtggagatc gcccacgcgc tctgcctctc gagcgccag     660 atcaagatct ggttccagaa ccggcgcatg aagtggaaaa agaccacaa gttgcccaac     720 accaagatcc gctcgggtgg tgcggcaggc tcagccggag ggccccctgg ccggcccaat     780
ggaggccccc gcgcgctcta g                                                801

<210> SEQ ID NO 16
<211> LENGTH: 266
<212> TYPE: PRT
<213> ORGANISM: artificial
<220> FEATURE:
<223> OTHER INFORMATION: mutant F6A TAT-Hoxb4

<400> SEQUENCE: 16
```

```
Met Ala Gly Tyr Gly Arg Lys Lys Arg Arg Gln Arg Arg Gly Met
1               5                  10                  15

Ala Met Ser Ser Ala Leu Ile Asn Ser Asn Tyr Val Asp Pro Lys Phe
            20                  25                  30

Pro Pro Cys Glu Glu Tyr Ser Gln Ser Asp Tyr Leu Pro Ser Asp His
            35                  40                  45

Ser Pro Gly Tyr Tyr Ala Gly Gly Gln Arg Arg Glu Ser Ser Phe Gln
    50                  55                  60

Pro Glu Ala Gly Phe Gly Arg Arg Ala Ala Cys Thr Val Gln Arg Tyr
65                  70                  75                  80

Ala Ala Cys Arg Asp Pro Gly Pro Pro Pro Pro Pro Pro Pro
                85                  90                  95

Pro Pro Pro Pro Pro Gly Leu Ser Pro Arg Ala Pro Ala Pro Pro
                100                 105                 110

Pro Ala Gly Ala Leu Leu Pro Glu Pro Gly Gln Arg Cys Glu Ala Val
            115                 120                 125

Ser Ser Ser Pro Pro Pro Pro Cys Ala Gln Asn Pro Leu His Pro
    130                 135                 140

Ser Pro Ser His Ser Ala Cys Lys Glu Pro Val Val Tyr Pro Trp Met
145                 150                 155                 160

Arg Lys Val His Val Ser Thr Val Asn Pro Asn Tyr Ala Gly Gly Glu
                165                 170                 175

Pro Lys Arg Ser Arg Thr Ala Tyr Thr Arg Gln Gln Val Leu Glu Leu
            180                 185                 190

Glu Lys Glu Phe His Tyr Asn Arg Tyr Leu Thr Arg Arg Arg Arg Val
        195                 200                 205

Glu Ile Ala His Ala Leu Cys Leu Ser Glu Arg Gln Ile Lys Ile Trp
    210                 215                 220

Phe Gln Asn Arg Arg Met Lys Trp Lys Lys Asp His Lys Leu Pro Asn
225                 230                 235                 240

Thr Lys Ile Arg Ser Gly Gly Ala Ala Gly Ser Ala Gly Gly Pro Pro
                245                 250                 255

Gly Arg Pro Asn Gly Gly Pro Arg Ala Leu
                260                 265

<210> SEQ ID NO 17
<211> LENGTH: 816
<212> TYPE: DNA
<213> ORGANISM: homo sapiens

<400> SEQUENCE: 17
atggccacca ccgggccct gggcaactac tatgtggact ccttcctgct gggcgccgac     60
gctgctgatg agctgggtgc gggacgctac gctccaggga ccctgggtca accccaagg   120 caggcggcag ctctggccga acaccccgac ttcagtcctt gcagcttcca gtccaaggcg   180
gcggtgtttg gtgcctcgtg aacccagtg cacgcggcgg cgccaatgc ggtgcctgct   240 gcagtgtatc atcaccacca ccaccccta cgtgcatccc aggcgcccgt ggcggcggcg   300
gcgccggacg gcaggtatat cgctcctgg ctggaaccca cgccggtgc gctctccttc   360 gcgggcttac cctccagccg gccttatggc attaaacctg aaccgctctc ggccagaagg   420
ggtgactgtc ccacgcttga cactcacact ttgtccctga ctgactatgc ttgtggttct   480
cctccagttg atagagaaaa acaacccagc gaaggcgcct tctccgaaaa caatgccgag   540
aatgagagcg gcggagacaa gccccccatc gatcccaata accggctgc caactggcta   600
```

```
catgctcgct ccactcggaa gaagcgatgc ccctacacaa acaccagac gctggaactg      660 gagaaggagt ttctgtttaa catgtacctc acacgggacc gcaggtacga ggtggcccgg    720
ctgctcaacc tcaccgaaag gcaggtcaag atctggttcc agaaccgcag gatgaaaatg    780
aagaaaatca acaaggaccg agcaaaagac gagtga                              816
```

<210> SEQ ID NO 18
<211> LENGTH: 271
<212> TYPE: PRT
<213> ORGANISM: homo sapiens

<400> SEQUENCE: 18

```
Met Ala Thr Thr Gly Ala Leu Gly Asn Tyr Tyr Val Asp Ser Phe Leu
 1               5                  10                  15

Leu Gly Ala Asp Ala Ala Asp Glu Leu Gly Ala Gly Arg Tyr Ala Pro
            20                  25                  30

Gly Thr Leu Gly Gln Pro Pro Arg Gln Ala Ala Leu Ala Glu His
        35                  40                  45

Pro Asp Phe Ser Pro Cys Ser Phe Gln Ser Lys Ala Ala Val Phe Gly
50                  55                  60

Ala Ser Trp Asn Pro Val His Ala Ala Gly Ala Asn Ala Val Pro Ala
65                  70                  75                  80

Ala Val Tyr His His His His His Pro Tyr Val His Pro Gln Ala Pro
                85                  90                  95

Val Ala Ala Ala Ala Pro Asp Gly Arg Tyr Met Arg Ser Trp Leu Glu
            100                 105                 110

Pro Thr Pro Gly Ala Leu Ser Phe Ala Gly Leu Pro Ser Ser Arg Pro
        115                 120                 125

Tyr Gly Ile Lys Pro Glu Pro Leu Ser Ala Arg Arg Gly Asp Cys Pro
    130                 135                 140

Thr Leu Asp Thr His Thr Leu Ser Leu Thr Asp Tyr Ala Cys Gly Ser
145                 150                 155                 160

Pro Pro Val Asp Arg Glu Lys Gln Pro Ser Glu Gly Ala Phe Ser Glu
                165                 170                 175

Asn Asn Ala Glu Asn Glu Ser Gly Gly Asp Lys Pro Pro Ile Asp Pro
            180                 185                 190

Asn Asn Pro Ala Ala Asn Trp Leu His Ala Arg Ser Thr Arg Lys Lys
        195                 200                 205

Arg Cys Pro Tyr Thr Lys His Gln Thr Leu Glu Leu Glu Lys Glu Phe
    210                 215                 220

Leu Phe Asn Met Tyr Leu Thr Arg Asp Arg Arg Tyr Glu Val Ala Arg
225                 230                 235                 240

Leu Leu Asn Leu Thr Glu Arg Gln Val Lys Ile Trp Phe Gln Asn Arg
                245                 250                 255

Arg Met Lys Met Lys Lys Ile Asn Lys Asp Arg Ala Lys Asp Glu
            260                 265                 270
```

<210> SEQ ID NO 19
<211> LENGTH: 1844
<212> TYPE: DNA
<213> ORGANISM: homo sapiens

<400> SEQUENCE: 19

```
aaaacgacaa cgcgagaaaa attagtattt ttgcacttca caattaatg accatgagct      60 cgttttgat aaactccaac tacatcgagc ccaagttccc tcccttcgag gagtacgcgc    120
agcacagcgg ctcgggcggc gcagacggcg gcccgggcgg gggccccggc taccagcagc    180
```

-continued

```
cccagcgcc cccgaccag cacctgccgc tgcagcagcc ccagctccct cacgcgggcg      240
gcggccgaga gcccctgcc tcctactacg cgccgcggac cgcccgcgag cccgcctacc      300
ctgctgccgc gctgtacccc cgcatggggc ccgcggacac cgcctacccc tatggctacc      360
gcggcggcgc cagccccggg cggccgcccc agcccgagca gccccggcg caagccaagg      420 gcccagcgca cggcctgcat gcgagccacg tcctgcagcc ccagccgccg ccgcccctgc      480
agcctcgcgc cgtgccccca gcggcccgc ggcgctgcga ggcggcccc gccacccag       540 gcgtcccggc aggggcagc gccccgcgt gccgctgct cttggccgac aagagcccgc       600
tgggcctgaa gggcaaggag cccgtggtgt acccctggat gaagaagatc catgtcagcg      660
ccgttaaccc cagttataac ggaggggagc ctaagcgctc tcgaaccgcc tacacccggc      720
agcaggtctt ggagctggag aaggagttcc acttcaatcg ctacctgacc cggcggcgcc      780
gcatcgagat cgcccacacg ctctgtttgt ctgagcgcca ggtcaagatc tggtttcaga      840
accggaggat gaagtggaag aaagaccaca aactgcccaa caccaagatg cgatcctcca      900
attcggcctc ggcctctgcc ggcccaccag ggaaagcaca aactcagagc ccacacctcc      960
atccccaccc ccaccgagc acctccacac ccgttccctc ctccatataa tcttctagag     1020
cttacctgct tttctcttct atcttaacca gtttctatcc cttctcctgc tccgttcctc     1080 atccaccct cccatctgg accataatag acaccaaaac aaacccaaat tggtgaaaag      1140
aataatcaaa aagaagacat tatccggtta agagtctgtg ctggttgcca cccaagagag      1200
aacagttgtc caggatgctg gctggtggaa caacctgctg gcccgaaaca aggctgccag      1260
gtgtggatac ctgagaagga ctacttggta tcaaatactt ttgagatggc tacagtcagc      1320
tagctggaca gccatgctg agtggggaca tacacttgca tctttgttga aagcagaaga      1380
agacagaccc tttcccccacc ttccttacct cctcttcccc cattaaggca gctcatccaa      1440
gcttgtattt aactgaataa atgagtagac attgtggacc tcacaagatt atttaattct      1500
taagatgtgt agaccttgat ggtaggtgtg acatgttagt ttttcttact tgcattttatt     1560 taagacactg ttacagagat actgttgtcc ccttctgggg cacggtcttt ggggagaggg     1620
gagtgcattt agacttatgt ggaactgtac aaattgtgat gtggctacat agaaagccat      1680
gtgctaagaa taaactccat ttaaaaaaca ttaaaaatct aagattcatg tgttttctaa      1740
gcttttcatt aagaaaacaa aagtcctctg gattgagata cttgaccttg catgtaaaaa      1800
ccttgtagat agcttgagct ggattcactt ggattctgac ggct                     1844
```

<210> SEQ ID NO 20
<211> LENGTH: 320
<212> TYPE: PRT
<213> ORGANISM: homo sapiens

<400> SEQUENCE: 20

| Met | Thr | Met | Ser | Ser | Phe | Leu | Ile | Asn | Ser | Asn | Tyr | Ile | Glu | Pro | Lys |
|---|---|---|---|---|---|---|---|---|---|---|---|---|---|---|---|
| 1 | | | | 5 | | | | | 10 | | | | | 15 | |

| Phe | Pro | Pro | Phe | Glu | Glu | Tyr | Ala | Gln | His | Ser | Gly | Ser | Gly | Gly | Ala |
|---|---|---|---|---|---|---|---|---|---|---|---|---|---|---|---|
| | | | 20 | | | | | 25 | | | | | 30 | | |

| Asp | Gly | Gly | Pro | Gly | Gly | Gly | Pro | Gly | Tyr | Gln | Gln | Pro | Pro | Ala | Pro |
|---|---|---|---|---|---|---|---|---|---|---|---|---|---|---|---|
| | | 35 | | | | | 40 | | | | | 45 | | | |

| Pro | Thr | Gln | His | Leu | Pro | Leu | Gln | Gln | Pro | Gln | Leu | Pro | His | Ala | Gly |
|---|---|---|---|---|---|---|---|---|---|---|---|---|---|---|---|
| | 50 | | | | | 55 | | | | | 60 | | | | |

| Gly | Gly | Arg | Glu | Pro | Pro | Ala | Ser | Tyr | Tyr | Ala | Pro | Arg | Thr | Ala | Arg |
|---|---|---|---|---|---|---|---|---|---|---|---|---|---|---|---|
| 65 | | | | | 70 | | | | | 75 | | | | | 80 |

-continued

```
Glu Pro Ala Tyr Pro Ala Ala Leu Tyr Pro Ala His Gly Ala Ala
            85                  90                  95

Asp Thr Ala Tyr Pro Tyr Gly Tyr Arg Gly Ala Ser Pro Gly Arg
           100                 105                 110

Pro Pro Gln Pro Glu Gln Pro Ala Gln Ala Lys Gly Pro Ala His
           115                 120                 125

Gly Leu His Ala Ser His Val Leu Gln Pro Gln Pro Pro Pro Leu
           130                 135                 140

Gln Pro Arg Ala Val Pro Ala Ala Pro Arg Arg Cys Glu Ala Ala
145                 150                 155                 160

Pro Ala Thr Pro Gly Val Pro Ala Gly Ser Ala Pro Ala Cys Pro
           165                 170                 175

Leu Leu Leu Ala Asp Lys Ser Pro Leu Gly Leu Lys Gly Lys Glu Pro
           180                 185                 190

Val Val Tyr Pro Trp Met Lys Lys Ile His Val Ser Ala Val Asn Pro
           195                 200                 205

Ser Tyr Asn Gly Gly Glu Pro Lys Arg Ser Arg Thr Ala Tyr Thr Arg
           210                 215                 220

Gln Gln Val Leu Glu Leu Glu Lys Glu Phe His Phe Asn Arg Tyr Leu
225                 230                 235                 240

Thr Arg Arg Arg Arg Ile Glu Ile Ala His Thr Leu Cys Leu Ser Glu
                    245                 250                 255

Arg Gln Val Lys Ile Trp Phe Gln Asn Arg Arg Met Lys Trp Lys Lys
                    260                 265                 270

Asp His Lys Leu Pro Asn Thr Lys Met Arg Ser Ser Asn Ser Ala Ser
                275                 280                 285

Ala Ser Ala Gly Pro Pro Gly Lys Ala Gln Thr Gln Ser Pro His Leu
           290                 295                 300

His Pro His Pro His Pro Ser Thr Ser Thr Pro Val Pro Ser Ser Ile
305                 310                 315                 320

<210> SEQ ID NO 21
<211> LENGTH: 1685
<212> TYPE: DNA
<213> ORGANISM: homo sapiens

<400> SEQUENCE: 21
agaaaaacga caaagcgaga aaaattattt tccactccag aaattaatga tcatgagctc      60
gtatttgatg gactctaact acatcgatcc gaaatttcct ccatgcgaag aatattcgca     120
aaatagctac atccctgaac acagtccgga atattacggc cggaccaggg aatcgggatt     180
ccagcatcac caccaggagc tgtacccacc accgcctccg cgccctagct accctgagcg     240
ccagtatagc tgcaccagtc tccaggggcc cggcaattcg cgaggccacg ggccggccca     300
ggcgggccac caccccccg agaaatcaca gtcgctctgc gagccggcgc ctctctcagg      360
cgcctccgcc tccccgtccc cagccccgcc agcctgcagc cagccagccc ccgaccatcc     420
ctccagcgcc gccagcaagc aacccatagt ctacccatgg atgaaaaaaa ttcacgttag     480
cacggtgaac cccagttata acggagggga acccaagcgc tcgaggacag cctatacccg     540
gcagcaagtc ctggaattag agaaagagtt tcattacaac cgctacctga cccgaaggag     600
aaggatcgag atcgcccact cgctgtgcct ctctgagagg cagatcaaaa tctggttcca     660
aaaccgtcgc atgaaatgga agaaggacca ccgactcccc aacaccaaag tcaggtcagc     720 accccccggcc ggcgctgcgc ccagcaccct ttcggcagct accccgggta cttctgaaga     780
ccactcccag agcgccacgc cgccggagca gcaacgggca gaggacatta ccaggttata     840
```

```
aaacataact cacacccctg cccccacccc atgccccac cctccctca cacacaaatt      900
gactcttatt tatagaattt aatatatata tatatatata tataggtt cttttctctc      960
ttcctctcac cttgtccctt gtcagttcca aacagacaaa acagataaac aaacaagccc    1020
cctgccctcc tctccctccc actgttaagg acccttttaa gcatgtgatg ttgtcttagc   1080
atggtacctg ctgggtgttt ttttttaaaa ggccattttg gggggttatt tatttttaa    1140
gaaaaaaagc tgcaaaaatt atatattgca aggtgtgatg gtctggcttg ggtgaatttc   1200
agggaaatg aggaaaagaa aaaggaaag aaattttaaa gccaattctc atccttctcc     1260
tcctcctcct tcccgcctct ttccttaggc cttttgcatt gaaatgcac caggggaggt    1320
tagtgagggg gaagtcattt taaggagaac aaagctatga agttcttttg tattattgtt   1380
ggggggggtg tgggaggaga gggggcgaag acagcagaca aagctaaatg catctggaga   1440
gcctctcaga gctgttcagt ttgaggagcc aaaagaaaat caaatgaac tttcagttca   1500
gagaggcagt ctataggtag aatctctccc caccccatc gtggttattg tgttttttgga   1560
ctgaatttac ttgattattg taaaacttgc aataaagaat tttagtgtcg atgtgaaatg   1620
ccccgtgatc aataataaac cagtggatgt gaattagttt taaaaaaaaa aaaaaaaaa   1680
aaaaa                                                                1685
```

<210> SEQ ID NO 22
<211> LENGTH: 264
<212> TYPE: PRT
<213> ORGANISM: homo sapiens

<400> SEQUENCE: 22

```
Met Ile Met Ser Ser Tyr Leu Met Asp Ser Asn Tyr Ile Asp Pro Lys
1               5                   10                  15

Phe Pro Pro Cys Glu Glu Tyr Ser Gln Asn Ser Tyr Ile Pro Glu His
            20                  25                  30

Ser Pro Glu Tyr Tyr Gly Arg Thr Arg Glu Ser Gly Phe Gln His His
        35                  40                  45

His Gln Glu Leu Tyr Pro Pro Pro Pro Arg Pro Ser Tyr Pro Glu
    50                  55                  60

Arg Gln Tyr Ser Cys Thr Ser Leu Gln Gly Pro Gly Asn Ser Arg Gly
65                  70                  75                  80

His Gly Pro Ala Gln Ala Gly His His Pro Glu Lys Ser Gln Ser
                85                  90                  95

Leu Cys Glu Pro Ala Pro Leu Ser Gly Ala Ser Ala Ser Pro Ser Pro
            100                 105                 110

Ala Pro Pro Ala Cys Ser Gln Pro Ala Pro Asp His Pro Ser Ser Ala
        115                 120                 125

Ala Ser Lys Gln Pro Ile Val Tyr Pro Trp Met Lys Lys Ile His Val
    130                 135                 140

Ser Thr Val Asn Pro Ser Tyr Asn Gly Gly Glu Pro Lys Arg Ser Arg
145                 150                 155                 160

Thr Ala Tyr Thr Arg Gln Gln Val Leu Glu Leu Glu Lys Glu Phe His
                165                 170                 175

Tyr Asn Arg Tyr Leu Thr Arg Arg Arg Ile Glu Ile Ala His Ser
            180                 185                 190

Leu Cys Leu Ser Glu Arg Gln Ile Lys Ile Trp Phe Gln Asn Arg Arg
        195                 200                 205

Met Lys Trp Lys Lys Asp His Arg Leu Pro Asn Thr Lys Val Arg Ser
    210                 215                 220
```

Ala Pro Pro Ala Gly Ala Ala Pro Ser Thr Leu Ser Ala Ala Thr Pro
225                 230                 235                 240

Gly Thr Ser Glu Asp His Ser Gln Ser Ala Thr Pro Pro Glu Gln Gln
            245                 250                 255

Arg Ala Glu Asp Ile Thr Arg Leu
        260

<210> SEQ ID NO 23
<211> LENGTH: 1298
<212> TYPE: DNA
<213> ORGANISM: homo sapiens

<400> SEQUENCE: 23

```
cattaatatc tggcaggggc tctcaaatgt gccatagcaa gctacttgat tacacgtatg      60
ttatttagtt aaatttgtga aaattatgag atgctcacca acccggtgat aaacttgctc     120
cctcgccatt ggctggcctg gtcacatggc tgcccaactt tattcagttg acagcaagta    180
ggagggccct atggaaggag aaaaaaagac aacacgagaa aaattagtat tttctacctt    240
ctgaaattaa tggtcatgag ttcgtatatg gtgaactcca agtatgtgga ccccaagttc    300
cctccgtgcg aggagtattt gcagggcggc tacctaggcg agcagggcgc cgactactac    360
ggcggcggcg cgcagggcgc agacttccag cccccgggc tctacccacg cccgacttc     420
ggtgagcagc ctttcggagg cagcggcccc gggcctggct cggcgctgcc tgcgcgggt    480
cacggacaag agccaggcgg ccccggcggt cactacgccg ctccaggaga gccttgccca    540
gctcccccgg cgcctccgcc ggcgcccctg cctggcgccc gggcctacag tcagtccgac    600
cccaagcagc cgccctccgg gacggcactc aagcagccgg ccgtggtcta cccctggatg    660
aagaaggtgc acgtgaattc ggtgaacccc aactacaccg gtggggaacc caagcggtcc    720
cgaacggcct acacccggca gcaagtccta gaactggaaa agaatttca ttttaacagg     780
tatctgacaa ggcgccgtcg gattgaaatc gctcacaccc tgtgtctgtc ggagcgccag    840
atcaagatct ggttccagaa ccggaggatg aagtggaaaa agatcataa gctgcccaac      900
actaaaggca ggtcatcgtc ctcatcttcc tcctcatctt gctcctcctc agtcgccccc    960
agccagcatt tacagccgat ggccaaagac caccacacgg acctgacgac cttatagaag   1020
tggggaccct gggcccatct ccctgcgc accaggctga ccgaagctg cggggggcagg     1080
ccgggcctgc tgtcacctcg ctgggctcta aggtactgtg gggtggacct gggacaagca   1140
ggccgccctc ggactaggtt agcatcctgc ccgagggcag ccccctccct agagcgggat   1200
ggggatggga gggggggcgg gattctctct ctaagtatat tatatggcag gagctactga   1260
gaacataaaa tcttggcgag tcattaaact tatgaaaa                           1298
```

<210> SEQ ID NO 24
<211> LENGTH: 255
<212> TYPE: PRT
<213> ORGANISM: homo sapiens

<400> SEQUENCE: 24

Met Val Met Ser Ser Tyr Met Val Asn Ser Lys Tyr Val Asp Pro Lys
1               5                   10                  15

Phe Pro Pro Cys Glu Glu Tyr Leu Gln Gly Gly Tyr Leu Gly Glu Gln
            20                  25                  30

Gly Ala Asp Tyr Tyr Gly Gly Gly Ala Gln Gly Ala Asp Phe Gln Pro
        35                  40                  45

Pro Gly Leu Tyr Pro Arg Pro Asp Phe Gly Glu Gln Pro Phe Gly Gly

```
                50                  55                  60
Ser Gly Pro Gly Pro Gly Ser Ala Leu Pro Ala Arg Gly His Gly Gln
 65                  70                  75                  80

Glu Pro Gly Gly Pro Gly Gly His Tyr Ala Ala Pro Gly Glu Pro Cys
                 85                  90                  95

Pro Ala Pro Pro Ala Pro Pro Ala Pro Leu Pro Gly Ala Arg Ala
            100                 105                 110

Tyr Ser Gln Ser Asp Pro Lys Gln Pro Ser Gly Thr Ala Leu Lys
            115                 120                 125

Gln Pro Ala Val Val Tyr Pro Trp Met Lys Lys Val His Val Asn Ser
130                 135                 140

Val Asn Pro Asn Tyr Thr Gly Gly Glu Pro Lys Arg Ser Arg Thr Ala
145                 150                 155                 160

Tyr Thr Arg Gln Gln Val Leu Glu Leu Glu Lys Glu Phe His Phe Asn
                165                 170                 175

Arg Tyr Leu Thr Arg Arg Arg Ile Glu Ile Ala His Thr Leu Cys
            180                 185                 190

Leu Ser Glu Arg Gln Ile Lys Ile Trp Phe Gln Asn Arg Arg Met Lys
            195                 200                 205

Trp Lys Lys Asp His Lys Leu Pro Asn Thr Lys Gly Arg Ser Ser Ser
210                 215                 220

Ser Ser Ser Ser Ser Cys Ser Ser Val Ala Pro Ser Gln His
225                 230                 235                 240

Leu Gln Pro Met Ala Lys Asp His His Thr Asp Leu Thr Thr Leu
            245                 250                 255

<210> SEQ ID NO 25
<211> LENGTH: 31
<212> TYPE: PRT
<213> ORGANISM: homo sapiens

<400> SEQUENCE: 25

Met Thr Met Ser Ser Phe Leu Ile Asn Ser Asn Tyr Ile Glu Pro Lys
 1               5                  10                  15

Phe Pro Pro Phe Glu Glu Tyr Ala Gln His Ser Gly Ser Gly Gly
             20                  25                  30

<210> SEQ ID NO 26
<211> LENGTH: 31
<212> TYPE: PRT
<213> ORGANISM: homo sapiens

<400> SEQUENCE: 26

Met Ala Met Ser Ser Phe Leu Ile Asn Ser Asn Tyr Val Asp Pro Lys
 1               5                  10                  15

Phe Pro Pro Cys Glu Glu Tyr Ser Gln Ser Asp Tyr Leu Pro Ser
             20                  25                  30

<210> SEQ ID NO 27
<211> LENGTH: 31
<212> TYPE: PRT
<213> ORGANISM: homo sapiens

<400> SEQUENCE: 27

Met Ile Met Ser Ser Tyr Leu Met Asp Ser Asn Tyr Ile Asp Pro Lys
 1               5                  10                  15

Phe Pro Pro Cys Glu Glu Tyr Ser Gln Asn Ser Tyr Ile Pro Glu
             20                  25                  30
```

<210> SEQ ID NO 28
<211> LENGTH: 31
<212> TYPE: PRT
<213> ORGANISM: homo sapiens

<400> SEQUENCE: 28

Met Val Met Ser Ser Tyr Met Val Asn Ser Lys Tyr Val Asp Pro Lys
1               5                   10                  15

Phe Pro Pro Cys Glu Glu Tyr Leu Gln Gly Gly Tyr Leu Gly Glu
            20                  25                  30

<210> SEQ ID NO 29
<211> LENGTH: 31
<212> TYPE: PRT
<213> ORGANISM: artificial
<220> FEATURE:
<223> OTHER INFORMATION: N-terminal 1-31 of hHox consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(31)
<223> OTHER INFORMATION: Xaa can be any naturally occurring amino acid

<400> SEQUENCE: 29

Met Xaa Met Ser Ser Xaa Xaa Xaa Xaa Ser Xaa Tyr Xaa Xaa Pro Lys
1               5                   10                  15

Phe Pro Pro Xaa Glu Glu Tyr Xaa Gln Xaa Xaa Xaa Xaa Xaa Xaa
            20                  25                  30

<210> SEQ ID NO 30
<211> LENGTH: 30
<212> TYPE: PRT
<213> ORGANISM: endeis spinosa

<400> SEQUENCE: 30

Met Cys Pro Phe Leu Met Asn Ser Gly Ser Tyr Val Asp Pro Lys Phe
1               5                   10                  15

Pro Pro Ser Glu Glu Tyr Ser Gln Asn Ser Tyr Ile Pro Ser
            20                  25                  30

<210> SEQ ID NO 31
<211> LENGTH: 32
<212> TYPE: PRT
<213> ORGANISM: Bombyx mori

<400> SEQUENCE: 31

```
Met Ser Ser Phe Leu Met Asn Gly Gly Tyr Gln Pro Gln Pro Asp Pro
1               5                   10                  15

Lys Phe Pro Pro Ser Glu Glu Tyr Ser Gln Ala Asp Tyr Ile Pro Pro
            20                  25                  30
```

```
<210> SEQ ID NO 32
<211> LENGTH: 45
<212> TYPE: PRT
<213> ORGANISM: Tribolium castaneum

<400> SEQUENCE: 32
```

```
Met Met Ser Ser Phe Leu Met Asn Pro Gly Thr Ala Leu Pro Thr Tyr
1               5                   10                  15

Gln Gln Pro Gln His Ile Ser Gly Val Val Asp Pro Lys Phe Pro
            20                  25                  30

Pro Ser Glu Glu Tyr Asn Gln Asn Ser Tyr Ile Pro Pro
            35                  40                  45
```

```
<210> SEQ ID NO 33
<211> LENGTH: 115
<212> TYPE: DNA
<213> ORGANISM: artificial
<220> FEATURE:
<223> OTHER INFORMATION: synthetic oligonucleotide

<400> SEQUENCE: 33
aattcccacc atggctatga gttctgcttt gatcaactca aactatgtcg accccaagtt      60
ccctccatgc gaggaatatt cacagagcga ttacctaccc agcgaccact cgccc         115
```

```
<210> SEQ ID NO 34
<211> LENGTH: 111
<212> TYPE: DNA
<213> ORGANISM: artificial
<220> FEATURE:
<223> OTHER INFORMATION: synthetic oligonucleotide

<400> SEQUENCE: 34
gggcgagtgg tcgctgggta ggtaatcgct ctgtgaatat tcctcgcatg gagggaactt      60
ggggtcgaca tagtttgagt tgatcaaagc agaactcata gccatggtgg g             111
```

```
<210> SEQ ID NO 35
<211> LENGTH: 115
<212> TYPE: DNA
<213> ORGANISM: artificial
<220> FEATURE:
<223> OTHER INFORMATION: synthetic oligonucleotide

<400> SEQUENCE: 35
aattcccacc atggctatga gttcttttgc tatcaactca aactatgtcg accccaagtt      60
ccctccatgc gaggaatatt cacagagcga ttacctaccc agcgaccact cgccc         115
```

```
<210> SEQ ID NO 36
<211> LENGTH: 111
<212> TYPE: DNA
<213> ORGANISM: artificial
<220> FEATURE:
<223> OTHER INFORMATION: synthetic oligonucleotide

<400> SEQUENCE: 36
gggcgagtgg tcgctgggta ggtaatcgct ctgtgaatat tcctcgcatg gagggaactt      60
ggggtcgaca tagtttgagt tgatagcaaa agaactcata gccatggtgg g             111
```

```
<210> SEQ ID NO 37
<211> LENGTH: 115
<212> TYPE: DNA
<213> ORGANISM: artificial
<220> FEATURE:
<223> OTHER INFORMATION: synthetic oligonucleotide

<400> SEQUENCE: 37
aattcccacc atggctatga gttcttttt gatcaactca aacgctgtcg accccaagtt      60
ccctccatgc gaggaatatt cacagagcga ttacctaccc agcgaccact cgccc         115

<210> SEQ ID NO 38
<211> LENGTH: 111
<212> TYPE: DNA
<213> ORGANISM: artificial
<220> FEATURE:
<223> OTHER INFORMATION: synthetic oligonucleotide

<400> SEQUENCE: 38
gggcgagtgg tcgctgggta ggtaatcgct ctgtgaatat tcctcgcatg gagggaactt      60
ggggtcgaca gcgtttgagt tgatcaaaaa agaactcata gccatggtgg g              111

<210> SEQ ID NO 39
<211> LENGTH: 115
<212> TYPE: DNA
<213> ORGANISM: artificial
<220> FEATURE:
<223> OTHER INFORMATION: synthetic oligonucleotide

<400> SEQUENCE: 39
aattcccacc atggctatga gttcttttt gatcaactca aactatgctg accccaagtt      60
ccctccatgc gaggaatatt cacagagcga ttacctaccc agcgaccact cgccc         115

<210> SEQ ID NO 40
<211> LENGTH: 111
<212> TYPE: DNA
<213> ORGANISM: artificial
<220> FEATURE:
<223> OTHER INFORMATION: synthetic oligonucleotide

<400> SEQUENCE: 40
gggcgagtgg tcgctgggta ggtaatcgct ctgtgaatat tcctcgcatg gagggaactt      60
ggggtcagca tagtttgagt tgatcaaaaa agaactcata gccatggtgg g              111

<210> SEQ ID NO 41
<211> LENGTH: 115
<212> TYPE: DNA
<213> ORGANISM: artificial
<220> FEATURE:
<223> OTHER INFORMATION: synthetic oligonucleotide

<400> SEQUENCE: 41
aattcccacc atggctatga gttcttttt gatcaactca aactatgtcg ctcccaagtt      60
ccctccatgc gaggaatatt cacagagcga ttacctaccc agcgaccact cgccc         115

<210> SEQ ID NO 42
<211> LENGTH: 111
<212> TYPE: DNA
<213> ORGANISM: artificial
<220> FEATURE:
<223> OTHER INFORMATION: synthetic oligonucleotide

<400> SEQUENCE: 42
gggcgagtgg tcgctgggta ggtaatcgct ctgtgaatat tcctcgcatg gagggaactt      60
```

```
gggagcgaca tagtttgagt tgatcaaaaa agaactcata gccatggtgg g          111
```

<210> SEQ ID NO 43
<211> LENGTH: 115
<212> TYPE: DNA
<213> ORGANISM: artificial
<220> FEATURE:
<223> OTHER INFORMATION: synthetic oligonucleotide

<400> SEQUENCE: 43

```
aattcccacc atggctatga gttcttttt gatcaactca aactatgtcg accccgcttt   60
ccctccatgc gaggaatatt cacagagcga ttacctaccc agcgaccact cgccc       115
```

<210> SEQ ID NO 44
<211> LENGTH: 111
<212> TYPE: DNA
<213> ORGANISM: artificial
<220> FEATURE:
<223> OTHER INFORMATION: synthetic oligonucleotide

<400> SEQUENCE: 44

```
gggcgagtgg tcgctgggta ggtaatcgct ctgtgaatat tcctcgcatg gagggaaagc   60
ggggtcgaca tagtttgagt tgatcaaaaa agaactcata gccatggtgg g           111
```

<210> SEQ ID NO 45
<211> LENGTH: 115
<212> TYPE: DNA
<213> ORGANISM: artificial
<220> FEATURE:
<223> OTHER INFORMATION: synthetic oligonucleotide

<400> SEQUENCE: 45

```
aattcccacc atggctatga gttcttttt gatcaactca aactatgtcg accccaaggc   60
tcctccatgc gaggaatatt cacagagcga ttacctaccc agcgaccact cgccc       115
```

<210> SEQ ID NO 46
<211> LENGTH: 111
<212> TYPE: DNA
<213> ORGANISM: artificial
<220> FEATURE:
<223> OTHER INFORMATION: synthetic oligonucleotide

<400> SEQUENCE: 46

```
gggcgagtgg tcgctgggta ggtaatcgct ctgtgaatat tcctcgcatg gaggagcctt   60
ggggtcgaca tagtttgagt tgatcaaaaa agaactcata gccatggtgg g           111
```

<210> SEQ ID NO 47
<211> LENGTH: 115
<212> TYPE: DNA
<213> ORGANISM: artificial
<220> FEATURE:
<223> OTHER INFORMATION: synthetic oligonucleotide

<400> SEQUENCE: 47

```
aattcccacc atggctatga gttcttttt gatcaactca aactatgtcg accccaagtt   60
ccctccatgc gaggaagctt cacagagcga ttacctaccc agcgaccact cgccc       115
```

<210> SEQ ID NO 48
<211> LENGTH: 111
<212> TYPE: DNA
<213> ORGANISM: artificial
<220> FEATURE:
<223> OTHER INFORMATION: synthetic oligonucleotide

<400> SEQUENCE: 48
gggcgagtgg tcgctgggta ggtaatcgct ctgtgaagct tcctcgcatg gagggaactt    60
ggggtcgaca tagtttgagt tgatcaaaaa agaactcata gccatggtgg g             111

<210> SEQ ID NO 49
<211> LENGTH: 115
<212> TYPE: DNA
<213> ORGANISM: artificial
<220> FEATURE:
<223> OTHER INFORMATION: synthetic oligonucleotide

<400> SEQUENCE: 49
aattcccacc atggctatga gttctttttt gatcaactca aactatgtcg accccaagtt    60
ccctccatgc gaggaatatt cacagagcga tgctctaccc agcgaccact cgccc         115

<210> SEQ ID NO 50
<211> LENGTH: 111
<212> TYPE: DNA
<213> ORGANISM: artificial
<220> FEATURE:
<223> OTHER INFORMATION: synthetic oligonucleotide

<400> SEQUENCE: 50
gggcgagtgg tcgctgggta gagcatcgct ctgtgaatat tcctcgcatg gagggaactt    60
ggggtcgaca tagtttgagt tgatcaaaaa agaactcata gccatggtgg g             111

<210> SEQ ID NO 51
<211> LENGTH: 115
<212> TYPE: DNA
<213> ORGANISM: artificial
<220> FEATURE:
<223> OTHER INFORMATION: synthetic oligonucleotide

<400> SEQUENCE: 51
aattcccacc atggctatga gttctttttt gatcaactca aactatgtcg accccaagtt    60
ccctccatgc gaggaatatt cacagagcga ttacgctccc agcgaccact cgccc         115

<210> SEQ ID NO 52
<211> LENGTH: 111
<212> TYPE: DNA
<213> ORGANISM: artificial
<220> FEATURE:
<223> OTHER INFORMATION: synthetic oligonucleotide

<400> SEQUENCE: 52
gggcgagtgg tcgctgggag cgtaatcgct ctgtgaatat tcctcgcatg gagggaactt    60
ggggtcgaca tagtttgagt tgatcaaaaa agaactcata gccatggtgg g             111

<210> SEQ ID NO 53
<211> LENGTH: 115
<212> TYPE: DNA
<213> ORGANISM: artificial
<220> FEATURE:
<223> OTHER INFORMATION: synthetic oligonucleotide

<400> SEQUENCE: 53
aattcccacc atggctatga gttctttttt gatcaactca aacttcgtcg accccaagtt    60
ccctccatgc gaggaatatt cacagagcga ttacctaccc agcgaccact cgccc         115

<210> SEQ ID NO 54
<211> LENGTH: 111

```
<212> TYPE: DNA
<213> ORGANISM: artificial
<220> FEATURE:
<223> OTHER INFORMATION: synthetic oligonucleotide

<400> SEQUENCE: 54
gggcgagtgg tcgctgggta ggtaatcgct ctgtgaatat tcctcgcatg gagggaactt      60
ggggtcgacg aagtttgagt tgatcaaaaa agaactcata gccatggtgg g              111

<210> SEQ ID NO 55
<211> LENGTH: 115
<212> TYPE: DNA
<213> ORGANISM: artificial
<220> FEATURE:
<223> OTHER INFORMATION: synthetic oligonucleotide

<400> SEQUENCE: 55
aattcccacc atggctatga gttcttttttt gatcaactca aactatgtcg accccaagtt    60
ccctccatgc gaggaattct cacagagcga ttacctaccc agcgaccact cgccc          115

<210> SEQ ID NO 56
<211> LENGTH: 111
<212> TYPE: DNA
<213> ORGANISM: artificial
<220> FEATURE:
<223> OTHER INFORMATION: synthetic oligonucleotide

<400> SEQUENCE: 56
gggcgagtgg tcgctgggta ggtaatcgct ctgtgagaat tcctcgcatg gagggaactt     60
ggggtcgaca tagtttgagt tgatcaaaaa agaactcata gccatggtgg g              111

<210> SEQ ID NO 57
<211> LENGTH: 115
<212> TYPE: DNA
<213> ORGANISM: artificial
<220> FEATURE:
<223> OTHER INFORMATION: synthetic oligonucleotide

<400> SEQUENCE: 57
aattcccacc atggctatga gttcttttttt gatcaactca aactatgtcg accccaagtt    60
ccctccatgc gaggaatatt cacagagcga tttcctaccc agcgaccact cgccc          115

<210> SEQ ID NO 58
<211> LENGTH: 111
<212> TYPE: DNA
<213> ORGANISM: artificial
<220> FEATURE:
<223> OTHER INFORMATION: synthetic oligonucleotide

<400> SEQUENCE: 58
gggcgagtgg tcgctgggta ggaaatcgct ctgtgaatat tcctcgcatg gagggaactt     60
ggggtcgaca tagtttgagt tgatcaaaaa agaactcata gccatggtgg g              111

<210> SEQ ID NO 59
<211> LENGTH: 115
<212> TYPE: DNA
<213> ORGANISM: artificial
<220> FEATURE:
<223> OTHER INFORMATION: synthetic oligonucleotide

<400> SEQUENCE: 59
aattcccacc atggctatga gttcttttttt gatcaactca aacttcgtcg accccaagtt    60
ccctccatgc gaggaattct cacagagcga ttacctaccc agcgaccact cgccc          115
```

<210> SEQ ID NO 60
<211> LENGTH: 111
<212> TYPE: DNA
<213> ORGANISM: artificial
<220> FEATURE:
<223> OTHER INFORMATION: synthetic oligonucleotide

<400> SEQUENCE: 60
gggcgagtgg tcgctgggta ggtaatcgct ctgtgagaat tcctcgcatg gagggaactt    60
ggggtcgacg aagtttgagt tgatcaaaaa agaactcata gccatggtgg g    111

<210> SEQ ID NO 61
<211> LENGTH: 115
<212> TYPE: DNA
<213> ORGANISM: artificial
<220> FEATURE:
<223> OTHER INFORMATION: synthetic oligonucleotide

<400> SEQUENCE: 61
aattcccacc atggctatga gttcttttt gatcaactca aacttcgtcg accccaagtt    60
ccctccatgc gaggaatatt cacagagcga tttcctaccc agcgaccact cgccc    115

<210> SEQ ID NO 62
<211> LENGTH: 111
<212> TYPE: DNA
<213> ORGANISM: artificial
<220> FEATURE:
<223> OTHER INFORMATION: synthetic oligonucleotide

<400> SEQUENCE: 62
gggcgagtgg tcgctgggta ggaaatcgct ctgtgaatat tcctcgcatg gagggaactt    60
ggggtcgacg aagtttgagt tgatcaaaaa agaactcata gccatggtgg g    111

<210> SEQ ID NO 63
<211> LENGTH: 115
<212> TYPE: DNA
<213> ORGANISM: artificial
<220> FEATURE:
<223> OTHER INFORMATION: synthetic oligonucleotide

<400> SEQUENCE: 63
aattcccacc atggctatga gttcttttt gatcaactca aactatgtcg accccaagtt    60
ccctccatgc gaggaattct cacagagcga tttcctaccc agcgaccact cgccc    115

<210> SEQ ID NO 64
<211> LENGTH: 111
<212> TYPE: DNA
<213> ORGANISM: artificial
<220> FEATURE:
<223> OTHER INFORMATION: synthetic oligonucleotide

<400> SEQUENCE: 64
gggcgagtgg tcgctgggta ggaaatcgct ctgtgagaat tcctcgcatg gagggaactt    60
ggggtcgaca tagtttgagt tgatcaaaaa agaactcata gccatggtgg g    111

<210> SEQ ID NO 65
<211> LENGTH: 115
<212> TYPE: DNA
<213> ORGANISM: artificial
<220> FEATURE:
<223> OTHER INFORMATION: synthetic oligonucleotide

<400> SEQUENCE: 65

```
aattcccacc atggctatga gttcttttt gatcaactca aacttcgtcg accccaagtt      60
ccctccatgc gaggaattct cacagagcga tttcctaccc agcgaccact cgccc         115

<210> SEQ ID NO 66
<211> LENGTH: 111
<212> TYPE: DNA
<213> ORGANISM: artificial
<220> FEATURE:
<223> OTHER INFORMATION: synthetic oligonucleotide

<400> SEQUENCE: 66
gggcgagtgg tcgctgggta ggaaatcgct ctgtgagaat tcctcgcatg gagggaactt     60
ggggtcgacg aagtttgagt tgatcaaaaa agaactcata gccatggtgg g             111
```

MUTATED HOXB4 PROTEINS WITH IMPROVED STABILITY, AND METHODS OF USE THEREOF

CROSS REFERENCE TO RELATED APPLICATIONS

This application claims priority, under 35 U.S.C. §119(e), of U.S. provisional application Ser. No. 60/941,472, filed on Jun. 1, 2007. This document above is incorporated herein in its entirety by reference.

FIELD OF THE INVENTION

The present invention relates to mutated HOXB4 proteins with improved stability, and methods of use thereof.

BACKGROUND OF THE INVENTION

Hematopoietic stem cells (HSCs) are rare cells that have been identified in fetal bone marrow, umbilical cord blood, adult bone marrow, and peripheral blood, which are capable of differentiating into each of the myeloerythroid (red blood cells, granulocytes, monocytes), megakaryocyte (platelets) and lymphoid (T-cells, B-cells, and natural killer) cells lineages. In addition these cells are long-lived, and are capable of producing additional stem cells, a process termed self-renewal. Stem cells initially undergo commitment to lineage restricted progenitor cells, which can be assayed by their ability to form colonies in semisolid media. Progenitor cells are restricted in their ability to undergo multi-lineage differentiation and have lost their ability to self-renew. Progenitor cells eventually differentiate and mature into each of the functional elements of the blood.

HSC are used in clinical transplantation protocols to treat a variety of diseases including malignant and non-malignant disorders.

HSCs obtained directly from the patient (autologous HSCs) are used for rescuing the patient from the effects of high doses of chemotherapy or used as a target for gene-therapy vectors. HSCs obtained from another person (allogeneic HSCs) are used to treat haematological malignancies by replacing the malignant haematopoietic system with normal cells. Allogeneic HSCs can be obtained from siblings (matched sibling transplants), parents or unrelated donors (mismatched unrelated donor transplants). About 45,000 patients each year are treated by HSC transplantation. Although most of these cases have involved patients with haematological malignancies, such as lymphoma, myeloma and leukaemia, there is growing interest in using HSC transplantation to treat solid tumours and non-malignant diseases. For example, erythrocyte disorders such as β-thalassaemia and sickle-cell anemia have been successfully treated by transplantation of allogeneic HSCs.

The search for factors that can stimulate HSC self-renewal has proven difficult, but recent reports indicate that selected molecules (sonic hedgehog (Bhardwaj), jagged1 (Karanu, 2000), fibroblast growth factor 1 (de Haan, 2003) and Wnt-3a (Willert, 2003)) can both, support maintenance or induce modest expansion of HSC. However, to date the HOXB4 transcription factor has proven to be the most potent stimulator of HSC self renewal (Antonchuk, 2001; Antonchuk, 2002). Similar effect of retrovirally driven ectopic expression of HOXB4 has also been reported for human cells (Buske, 2002; Schiedlmeier, 2003). In addition, it has been shown that recombinant TAT-HOXB4 protein, when added to the HSC culture, could penetrate the cell membrane and provides significant HSC expansion stimuli (Krosl, 2003; US 2004/0082003) and similar effect of stroma cell derived HOXB4 on human HSC has also been reported (Ansellem, 2003). Human HSC, assessed with NOD/SCID SRC assay, can be efficiently and significantly expanded ex vivo using TAT-HOXB4 protein (Krosl, 2005a; Krosl, 2005b). One of the major advantages of TAT-HOXB4 expansion is the fact that it can be performed using recombinant protein, that is without possible drawbacks of gene transfer protocols (Baum, 2004; Modlich, 2005; Woods, 2006).

The major impediment for the use of HOXB4 in clinical setting with or without a PTD (protein transduction domain) such as that of the N-terminal of TAT is its short intracellular and extracellular half-life (40-60 minutes and 3-4 hours, respectively) (Krosl, 2003). With expansion times lasting 4-8 days, that translates into extensive culture manipulation increasing the risk of culture contamination. More stable HOXB4 molecules with similar HSC expansion capabilities would significantly increase its usability in clinical settings.

DNA binding activity of HOXB4 is required to induce HSCs expansion but not its collaboration with PBX1 (Beslu, 2004), even more PBX1 might be a negative regulator of HOXB4 (Krosl, 2003). More recently, the over expression of associated with the down regulation of PBX1 were shown to be able to sustained in vitro symmetrical (i.e. symmetrical division: production of two identical cells by opposition to asymmetrical division: division into one identical cell and one differentiated cell) self-renewal divisions of HSCs. Modulation of transcription of cell cycle regulators induced by HOXB4 over expression in primitive hematopoietic cells, was more pronounced with inhibition of PBX1 expression in these cells (Cellot, 2007) (see also co-pending US 2006/0121566).

The present description refers to a number of documents, the content of which is herein incorporated by reference in their entirety.

SUMMARY OF THE INVENTION

The present invention is concerned with the identification of processes involved in HOXB4 protein degradation, in order to generate more stable and more active proteins useful for therapeutic purpose. The present invention shows that HOXB4 protein is degraded by the ubiquitin-proteasome pathway.

The inventors sought to determine whether HOXB4 was regulated in part by its degradation and if so whether its half-life could be increased by reducing its susceptibility to degradation.

The ubiquitin-proteasome system is a major pathway for intracellular protein degradation. Schematically, this biological process involved the E1 ubiquitin-activating enzyme, which activates ubiquitin. Then the E2 ubiquitin-conjugating enzyme transfers ubiquitin to a targeted substrate with the help of the E3 ubiquitin ligase. This enzymatic cascade gives rise to the poly ubiquitination of the substrate inducing its recognition and degradation by the 26S proteasome (Hershko and Ciechanover, 1998). There are numerous E3 ubiquitin ligases, and this variety confers substrate specificity to the system. These enzymes recognize a sequence on substrates named degron that are both necessary and sufficient for protein degradation (Pickart, 2004).

Few laboratories have analyzed the regulation of HOX protein degradation to date. Gabellini et al. have shown that HOXC10 protein degradation occurred during mitosis and involved the anaphase-promoting complex (APC) as the E3 ubiquitin-ligase. This targeted degradation required two D-box motifs of HOXC10, which are known to be specific recognition sequence of APC. They also suggested a role in mitotic progression for HOXC10 protein degradation (Gabellini, 2003). More relevant for HOXB4, HOXA9 involved in HSC expansion (contrarily to HOXB4 however, it is also known to induce leukemia) (Kroon, 1997; Thorsteinsdottir, 1999), is degraded by Cullin 4A (Cul-4A) complex. Moreover, the helix 1 of its homeodomain acts as a recognition signal for Cul-4A ubiquitination machinery. They also show in this study that HOXA9 protein degradation induced by the Cul-4A complex is required to remove the inhibition of cell differentiation induced by HOXA9 over expression in 32-D cell line (Zhang Embo 2003).

The present invention showed that the 31 N-terminal amino-acids (aa), highly conserved between paralogs and among evolution, encompass a new degron: deletion of these aa allowed generating an HOXB4 protein 3 times more stable than the wild type protein. Moreover, this domain is not required for HOXB4 effect on hematopoietic reconstitution of mice transplanted with bone marrow cells. The present invention also relates to identification of point mutants in this region which induce rapid expansion of HSCs and that are capable of rapid and sustained hematopoietic reconstitution of transplanted mice. Active highly stable forms of this HSC expanding factor were thus generated by reducing susceptibility of HOXB4 to ubiquitin-proteasome degradation.

Expansion methods. Expansion of HSCs in accordance with methods of the present invention can be performed by infecting or transfecting a HSC population with an effective amount of vectors expressing recombinant HOXB4s or by contacting the population with recombinant HOXB4 proteins of the present invention. Expansion of bone marrow cells can be performed in a bioreactor such as the AastromReplicell™ system from Aastrom Biosciences (USA) or the Cytomatrix™ Bioreactor from Cytomatrix. It can also be performed using low molecular chelate for copper binding such as the StemEx™ from Gamida (Israel) or using culture systems such as MainGen (Germany) or culture medium such as ViaCell (USA).

Gene therapy Gene therapy involves collecting HSCs from the patient and genetically modifying them with a therapeutic transgene. This genetic modification is typically carried out using vectors such as a retrovirus (including lentivirus), adenovirus, AAV Virus (adeno-associated viruses), poxvirus, Herpes simplex virus, vesicular stomatitis virus, murine leukemia virus, polyoma virus and cytomegalovirus. Although in Examples presented herein, the retroviral murine stem cell virus (MSCV) vector was used to infect bone marrow cells, the present invention is thus not so limited.

Kits. The present invention also relates to a kit for expanding HScs and/or hematopoietic progenitor cells comprising a nucleic acid, a protein or a ligand in accordance with the present invention. For instance it may comprise a recombinant HOXB4 of the present invention or a vector encoding same, and instructions to use said composition or vector to expand HSCs and/or hematopoietic progenitor cells ex vivo or in vivo. Such kits may further comprise at least one other active agent able to favor HSCs and/or hematopoietic progenitor cells expansion. When the kit is used to expand HSCs and/or hematopoietic progenitor cells ex vivo or in vivo in a subject in need of such expansion (ex. subject needing a bone marrow transplantation, etc.), the kit may also further comprise at least one other active agent capable of directly or indirectly expanding HSCs and/or hematopoietic progenitor cells. Such active agents include agents such as those described in co-pending US 2006/0121566. In addition, a compartmentalized kit in accordance with the present invention includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample (DNA protein or cells), a container which contains the primers used in the assay, containers which contain enzymes, containers which contain wash reagents, and containers which contain the reagents used to detect the extension products.

Polypeptides and vectors of the present invention can be used in association with other agents known to directly or indirectly induce HSCs expansion such as PBX1 inhibitors.

In another aspect, the present invention is concerned with the addition of the HOXB4 degron in N-terminal of proteins in order to provoke their eventual destabilization. Such destabilization would be useful for marker proteins such as fluorescent proteins and oncogenic proteins for use in animal models for instance.

As used herein the terminology "at least one mutation that reduces the susceptibility of the polypeptide to 26S ubiquitin-proteasome" refers to any mutation including one or more deletions, one or more insertions and one or more substitutions in the degron domain of HOXB4, HOXC4 or HOXD4 that reduces the susceptibility of HOXB4 to ubiquitin-proteasome degradation. Without being so limited, deletions encompassed by this definition include a deletion of the whole degron domain or of a fragment thereof that that reduces the susceptibility of HOXB4 to ubiquitin-proteasome degradation. In particular, it refers to a deletion of the 1-26, 1-27, 1-28, 1-29, 1-30, 1-31, 1-32, 1-33, 1-34, 1-35, 1-36 or 1-37 N-terminal fragment of HOXB4. Without being so limited, substitutions encompassed by this definition include substitutions at positions 6, 7, 23 or 28 of the HOXB4 domain for an aliphatic nonpolar neutral amino acid residue.

As used herein the term "aliphatic nonpolar neutral" used in reference to an amino acid residue is meant to refer to a glycine, isoleucine, leucine (except in position 7), and valine.

As used herein the term "subject" is meant to refer to any mammal including human, mice, rat, dog, cat, pig, monkey, horse, etc. In a particular embodiment, it refers to a human.

As used herein the term "purified" in the expression "purified polypeptide" means altered "by the hand of man" from its natural state (i.e. if it occurs in nature, it has been changed or removed from its original environment) or it has been synthesized in a non-natural environment (e.g., artificially synthesized). These terms do not require absolute purity (such as a homogeneous preparation) but instead represents an indication that it is relatively more pure than in the natural environment. For example, a protein/peptide naturally present in a living organism is not "purified", but the same protein separated (about 90-95% pure at least) from the coexisting materials of its natural state is "purified" as this term is employed herein.

Similarly, as used herein, the term "purified" in the expression "purified antibody" is simply meant to distinguish man-made antibody from an antibody that may naturally be produced by an animal against its own antigens. Hence, raw serum and hybridoma culture medium containing anti-mutated HOXB4 antibody are "purified antibodies" within the meaning of the present invention.

As used herein the terminology "hematopoietic stem cells (HSC)" refers to cells which are capable of differentiating into each of the myeloerythroid (red blood cells, granulocytes, monocytes), megakaryocyte (platelets) and lymphoid (T-cells, B-cells, and natural killer cells lineages). In addition these cells are capable of producing additional stem cells, a process termed self-renewal. The most used marker to this to enrich HSCs is $CD34^+$. It is not sufficient to obtain completely purified HSCs.

As used herein the terminology "hematopoietic stem cell-containing population" is meant to refer to a cell population from any autologous and/or allogeneic source, and/or a mixture thereof that comprises HSCs but may include other cell types such as hematopoietic progenitor cells and mature blood cells and that is able upon application of the polypeptide or isolated nucleic acid of the present invention to proliferate.

Source of HSCs. Bone marrow and peripheral blood have been traditionally used as sources of HSCs. When using bone marrow cells as a source of HSCs, donors must traditionally undergo several aspirations to collect several thousand milliliters of bone marrow, a procedure that is carried out in the operating room under general anaesthesia. An alternative source is HSCs from the peripheral blood, collected after treating the donor with granulocyte colony-stimulating factor to increase the number of circulating HSCs. Both of these procedures entail some risk and are relatively costly.

One important new source of HSCs is umbilical cord blood that is collected during newborn deliveries. In addition to their widespread availability, these HSCs have several useful properties, including their decreased ability to induce immunological reactivity against the patient because of increased levels of immune tolerance in the fetus. Interest in this approach has increased since the first successful transplantation of cord-blood HSCs in 1988, and there are now an estimated 70,000 units of cord blood that are stored and available for transplantation. However, their use is limited by the number of HSCs that can be collected, and it is clear that engraftment is closely correlated with the number of cells that are infused. Furthermore, cord blood transplantation is difficult to use for treating adult patients because of the limited number of cells that are available, so it has generally been limited to paediatric patients.

As used herein, the term "ligand" broadly refers to natural, synthetic or semi-synthetic molecules. The term "molecule" therefore denotes for example chemicals, macromolecules, cell or tissue extracts (from plants or animals) and the like. Non limiting examples of molecules include nucleic acid molecules, peptides, antibodies, carbohydrates and pharmaceutical agents. The ligand appropriate for the present invention can be selected and screened by a variety of means including random screening, rational selection and by rational design using for example protein or ligand modeling methods such as computer modeling. The terms "rationally selected" or "rationally designed" are meant to define compounds which have been chosen based on the configuration of interacting domains of the present invention. As will be understood by the person of ordinary skill, macromolecules having non-naturally occurring modifications are also within the scope of the term "ligand". For example, peptidomimetics, well known in the pharmaceutical industry and generally referred to as peptide analogs can be generated by modeling as mentioned above.

Antibodies. As used herein, the term "anti-mutated HOXB4 (or HOXA4, HOXC4 or HOXD4) antibody" or "immunologically specific anti-HOXB4 (or HOXA4, HOXC4 or HOXD4) antibody" refers to an antibody that specifically binds to (interacts with) a HOXB4 protein and displays no substantial binding to other naturally occurring proteins other than the ones sharing the same antigenic determinants as the mutated HOXB4 protein. The term antibody or immunoglobulin is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', $F(ab')_2$, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$-$V_H$), anticalins, PepBodies™, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g. Fab and Fab' fragments) which inhibit or neutralize their respective interaction domains in Hyphen and/or are specific thereto.

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals may be immunized against the antigen, immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to 1/10 of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293 (see also, e.g., Lindenbaum et al., 2004).

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell (see, e.g., Goding 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

As used herein the term "therapeutically effective amount" is meant to refer to an amount effective to achieve the desired effect while avoiding adverse side effects. Typically, mutated HOXB4 in accordance with the present invention can be administered ex vivo or in vivo in doses ranging from 0.001 to 500 mg/kg/day and, in a more specific embodiment, about 0.1 to about 100 mg/kg/day, and, in a more specific embodiment, about 0.2 to about 20 mg/kg/day. The allometric scaling method of Mahmood et al. (J. Clin. Pharmacol. 2003, 43 (7), 692-7) can be used to extrapolate the dose from mice to human. The dosage will be adapted by the clinician in accordance with conventional factors such as the extent of the disease and different parameters from the patient. In particular embodiments where TAT-mutated HOXB4 are used, a dosage of about 20 nM to about 80 nM can optimally be used. For instance treatment of murine bone marrow cells with 10 nM of TAT-HOXB4 over 4 days provide a HSCs expansion of 5 times that on Day 0 and of 13 times that on Day 4 of cells treated with TATGFP. The specific concentration obviously depends on the concentration of cells. Also, in embodiments where mutated HOXB4 are used, a higher dosage is used.

As used herein, the term "a" or "the" means "at least one".

The methods of the present invention encompass advantageously expanding HSCs from any of these sources.

More specifically, in accordance with the present invention, there is provided a polypeptide, the amino acid sequence of which comprises a sequence as set forth in FIG. 15A (SEQ ID NO:2), including at least one mutation within the degron domain of the polypeptide encompassed between positions 1 and 35 of the sequence, wherein said at least one mutation reduces the susceptibility of the polypeptide to ubiquitin-proteasome degradation.

In a specific embodiment of the polypeptide, said at least one mutation is selected from the group consisting of a mutation replacing the amino acid residue at position 6, 7, 23 or 28 with an aliphatic nonpolar neutral amino acid residue; and a deletion of the first 31 to 35 amino acid residues of the a sequence as set forth in FIG. 15A (SEQ ID NO:2). In another specific embodiment of the polypeptide, said at least one mutation replaces the amino acid residue at position 6 with an aliphatic nonpolar neutral amino acid residue. In another specific embodiment of the polypeptide, said at least one mutation replaces the amino acid residue at position 7 with an aliphatic nonpolar neutral amino acid residue. In another specific embodiment of the polypeptide, said at least one mutation replaces the amino acid residue at position 23 with an aliphatic nonpolar neutral amino acid residue. In another specific embodiment of the polypeptide, said at least one mutation replaces the amino acid residue at position 28 with an aliphatic nonpolar neutral amino acid residue. In another specific embodiment of the polypeptide, the aliphatic nonpolar neutral amino acid residue is selected from the group consisting of glycine, alanine and valine. In another specific embodiment of the polypeptide, the aliphatic nonpolar neutral amino acid residue is alanine. In another specific embodiment of the polypeptide, said at least one mutation is a deletion of the first N-terminal 31 to 35 amino acid residues. In another specific embodiment, the amino acid sequence of the polypeptide comprises the sequence as set forth in FIG. 16 A (SEQ ID NO:4).

In accordance with another aspect the present invention, there is provided a polypeptide, the amino acid sequence of which comprises a sequence as set forth in FIG. 18A (SEQ ID NO:20), including at least one mutation within the degron domain of the polypeptide encompassed between positions 1 and 35 of the sequence, wherein said at least one mutation reduces the susceptibility of the polypeptide to ubiquitin-proteasome degradation.

In accordance with another aspect the present invention, there is provided a polypeptide, the amino acid sequence of which comprises a sequence as set forth in FIG. 19A (SEQ ID NO:22), including at least one mutation within the degron domain of the polypeptide encompassed between positions 1 and 35 of the sequence, wherein said at least one mutation reduces the susceptibility of the polypeptide to ubiquitin-proteasome degradation.

In accordance with another aspect the present invention, there is provided a polypeptide, the amino acid sequence of which comprises a sequence as set forth in FIG. 20A (SEQ ID NO:24), including at least one mutation within the degron domain of the polypeptide encompassed between positions 1 and 35 of the sequence, wherein said at least one mutation reduces the susceptibility of the polypeptide to ubiquitin-proteasome degradation. In a specific embodiment, the polypeptide further comprises a protein transduction domain (PTD). In another specific embodiment, the PTD is a HIV-derived peptide. In another specific embodiment, the HIV-derived peptide is a $NH_2$-terminal PTD from a transactivating protein (TAT). In another specific embodiment, the $NH_2$-terminal PTD from a TAT comprises the sequence Tyr-Gly-Arg-Lys-Lys-Arg-Arg-Gln-Arg-Arg-Arg (SEQ ID NO:6).

In accordance with another aspect the present invention, there is provided a purified antibody that binds specifically to the polypeptide of the present invention.

In accordance with another aspect the present invention, there is provided an isolated nucleic acid, comprising a sequence that encodes the polypeptide of the present invention.

In accordance with another aspect the present invention, there is provided an isolated nucleic acid, the nucleotide sequence of which comprises a sequence as set forth in SEQ ID NO:1 including nucleotides at positions 16-18, 19-21, 67-69 or 82-84 replaced by a codon selected from the group consisting of guanine-cytosine-thymine (GCT), guanine-cytosine-alanine (GCA), guanine-cytosine-cytosine (GCC) or guanine-cytosine-guanine (GCG). In a specific embodiment, the nucleotide sequence of the isolated nucleic acid comprises a sequence as set forth in FIG. 15B (SEQ ID NO:1) including nucleotides at position 16-18 replaced by GCT. In another specific embodiment, the nucleotide sequence of the isolated nucleic acid comprises a sequence as set forth in FIG. 15B (SEQ ID NO:1) including nucleotides at position 19-21 replaced by GCG. In another specific embodiment, the nucleotide sequence of the isolated nucleic acid comprises a sequence as set forth in FIG. 15B (SEQ ID NO:1) including nucleotides at position 67-69 replaced by GCT. In another specific embodiment, the nucleotide sequence of the isolated nucleic acid comprises a sequence as set forth in FIG. 15B (SEQ ID NO:1) including nucleotides at position 82-84 replaced by GCC.

In accordance with another aspect the present invention, there is provided a recombinant expression vector comprising the nucleic acid of the present invention operably linked to an expression control sequence. In a specific embodiment, the vector is a retroviral vector. In another specific embodiment, the retroviral vector is a murine stem cell virus (MSVC). In another specific embodiment, the vector is an adenoviral vector.

In accordance with another aspect the present invention, there is provided a recombinant host cell comprising the vector of the present invention, or a progeny of said cell, wherein said cell expresses the product of the nucleic acid. In a specific embodiment, the cell is a bone marrow cell. In another specific embodiment, the cell is a hematopoietic stem cell. In another specific embodiment, the cell is a hematopoietic progenitor cell.

In accordance with another aspect the present invention, there is provided a cell population comprising the cell of the present invention.

In accordance with another aspect the present invention, there is provided a kit comprising the polypeptide of the present invention, and instructions to use the polypeptide to expand a hematopoietic stem cell-containing population.

In accordance with another aspect the present invention, there is provided a kit comprising the nucleic acid of the present invention, and instructions to use the polypeptide to expand a hematopoietic stem cell-containing population.

In accordance with another aspect the present invention, there is provided a kit comprising the antibody of the present invention, and instructions to use the antibody to detect the polypeptide. In a specific embodiment, the kit further comprises another agent known to stimulate HSC expansion.

In accordance with another aspect the present invention, there is provided a method for enhancing expansion of a hematopoietic stem cell (HSC)-containing population comprising contacting the HSC population with a therapeutically effective amount of the polypeptide of the present invention, whereby the HSC-containing population is expanded.

In accordance with another aspect the present invention, there is provided a method for enhancing expansion of a hematopoietic stem cell (HSC)-containing population comprising contacting the HSC population with a therapeutically effective amount of the nucleic acid of the present invention, whereby the HSC-containing population is expanded.

In accordance with another aspect the present invention, there is provided a method for enhancing expansion of a hematopoietic stem cell (HSC)-containing population comprising contacting the HSC population with a therapeutically effective amount of the cell population of the present invention, whereby the HSC-containing population is expanded.

In specific embodiments of the method of the present invention, the contacting is performed ex vivo. In other specific embodiments of the method of the present invention, the contacting is performed in vivo. In other specific embodiments of the method of the present invention, the HSC-containing population is umbilical cord blood. In other specific embodiments of the method of the present invention, the HSC-containing population is peripheral blood. In other specific embodiments of the method of the present invention, the HSC-containing population is bone marrow. In other specific embodiments of the method of the present invention, the HSC-containing population is that of a human.

In accordance with another aspect the present invention, there is provided a method of producing the polypeptide of the present invention, the method comprising culturing the cell of the present invention under conditions permitting expression of the polypeptide, and purifying the polypeptide from the cell or the medium of the cell.

In accordance with another aspect the present invention, there is provided a method of identifying mutated HOXB4 proteins with a half-life longer than that of wild type HOXB4 comprising testing the susceptibility of a mutated HOXB4 candidate to ubiquitin-proteasome degradation, whereby the susceptibility of ubiquitin-proteasome degradation of the candidate lower than that of the wild type HOXB4 is an indication that its half-life is longer than that of the wild type HOXB4.

In a specific embodiment of the method of the present invention, the mutated HOXB4 candidates used for the susceptibility testing comprise at least one mutation in their first 35 N-terminal amino acid residues.

In accordance with another aspect the present invention, there is provided a use of the polypeptide of the present invention, for expanding a hematopoietic stem cell (HSC)-containing population.

In accordance with another aspect the present invention, there is provided a HOXB4 purified polypeptide, the amino acid sequence of which comprises the consensus amino acid sequence in FIG. 3A (SEQ ID NO:29). In a specific embodiment, the amino acid sequence of the polypeptide comprises amino acid residues 1 to 25 of the sequence in FIG. 16C (SEQ ID NO:5). In another specific embodiment, the amino acid sequence of the polypeptide comprises amino acid residues 1 to 26 of the sequence in FIG. 16C (SEQ ID NO:5). In another specific embodiment, the amino acid sequence of the polypeptide comprises amino acid residues 1 to 27 of the sequence in FIG. 16C (SEQ ID NO:5). In another specific embodiment, the amino acid sequence of the polypeptide comprises amino acid residues 1 to 28 of the sequence in FIG. 16C (SEQ ID NO:5). In another specific embodiment, the amino acid sequence of the polypeptide comprises amino acid residues 1 to 29 of the sequence in FIG. 16C (SEQ ID NO:5). In another specific embodiment, the amino acid sequence of the polypeptide comprises amino acid residues 1 to 30 of the sequence in FIG. 16C (SEQ ID NO:5). In another specific embodiment, the amino acid sequence of the polypeptide comprises amino acid residues 1 to 31 of the sequence in FIG. 16C (SEQ ID NO:5). In another specific embodiment, the amino acid sequence of the polypeptide comprises amino acid residues 1 to 32 of the sequence in FIG. 16C (SEQ ID NO:5). In another specific embodiment, the amino acid sequence of the polypeptide comprises amino acid residues 1 to 33 of the sequence in FIG. 16C (SEQ ID NO:5). In another specific embodiment, the amino acid sequence of the polypeptide comprises amino acid residues 1 to 34 of the sequence in FIG. 16C (SEQ ID NO:5). In another specific embodiment, the amino acid sequence of the polypeptide comprises amino acid residues 1 to 35 of the sequence in FIG. 16C (SEQ ID NO:5). In another specific embodiment, the polypeptide further comprises a marker protein. In another specific embodiment, the marker protein is a fluorescent marker protein. In another specific embodiment, the fluorescent marker protein is selected from the group consisting of Green fluorescent protein (GFP), Cyanin fluorescent protein (CyaninFP), Yellow fluorescent protein (YellowFP), Blue fluorescent protein (BlueFP) and Red fluorescent protein (RedFP).

In accordance with another aspect the present invention, there is provided a purified antibody that binds specifically to the polypeptide of the present invention.

In accordance with another aspect the present invention, there is provided an isolated nucleic acid, comprising a sequence that encodes the polypeptide of the present invention.

In accordance with another aspect the present invention, there is provided an isolated nucleic acid, the nucleotide sequence of which comprises a sequence as set forth in FIG. 16C (SEQ ID NO:5).

In accordance with another aspect the present invention, there is provided a recombinant expression vector comprising the nucleic acid of the present invention, operably linked to an expression control sequence.

In accordance with another aspect the present invention, there is provided a recombinant host cell comprising the vector of the present invention, or a progeny of said cell, wherein said cell expresses the nucleic acid.

In accordance with another aspect the present invention, there is provided a recombinant host cell comprising the vector of the present invention.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 3 presents the sequence alignment of the N-terminal region of the human 4 paralogs (HOXA4 (SEQ ID NO:25), HOXB4 (SEQ ID NO:26), HOXC4 (SEQ ID NO:27), HOXD4 (SEQ ID NO:28)) and a consensus sequence of this region (SEQ ID NO:29) (Panel A) wherein X in a first embodiment can be any amino acid residue and in a further embodiment, can be any amino acid residue found at that position in any of the paralogs; and a sequence alignment of N-terminal region of HOXB4 and 3 different DFDs HOXB4, *Endeis spinosa* (SEQ ID NO:30), *Bombyx mori* (SEQ ID NO:31) and *Tribolium castaneum* (SEQ ID NO:32) (Panel B). These sequences alignments were performed by NCBI Blast. Dots represent residues identical to those in the HOXB4 human protein, and dashes represent gaps;

FIG. 15 shows the amino acid sequence (SEQ ID NO:2) (Panel A) and nucleotide sequence (SEQ ID NO:1) (Panel B) of human wt HOXB4;

FIG. 16 shows the amino acid sequence (SEQ ID NO:4) (Panel A) and nucleotide sequence (SEQ ID NO:3) (Panel B) of human wt HOXB4 (delta 1-31) (deletion of 35 N-terminal amino acids). Panel C shows the N-terminal degron domain (SEQ ID NO:5) (Panel C);

FIG. 17 shows the amino acid sequence (SEQ ID NO:18) (Panel A) and nucleotide sequence (SEQ ID NO:17) (Panel B) of human wt HOXA9;

FIG. 18 shows the amino acid sequence (SEQ ID NO:20) (Panel A) and nucleotide sequence (SEQ ID NO:19) (Panel B) of human wt HOXA4;

FIG. 19 shows the amino acid sequence (SEQ ID NO:22) (Panel A) and nucleotide sequence (SEQ ID NO:21) (Panel B) of human wt HOXC4;

FIG. 20 shows the amino acid sequence (SEQ ID NO:24) (Panel A) and nucleotide sequence (SEQ ID NO:23) (Panel B) of human wt HOXD4;

FIG. 21 shows an alignment of HOXA4 (SEQ ID NO:20), HOXB4 (SEQ ID NO:2) and HOXC4 (SEQ ID NO:22);

FIG. 22 shows the wild type TAT-HOXB4 (SEQ ID NOS:7 and 8) cDNA and protein sequences. The TAT sequence is shown in bold; and FIG. 23 shows the mutant TAT-HOXB4 cDNA and protein sequences: a) L7A TAT-HOXB4 mutant (SEQ ID NOS:9 and 10); B) Y23A TAT-HOXB4 mutant (SEQ ID NOS:11 and 12); C) Y28A TAT-HOXB4 mutant (SEQ ID NOS:13 and 14); and D) F6A TAT-HOXB4 mutant (SEQ ID NOS:15 and 16). The TAT sequence is shown in bold and the mutations are shown in bold and are underlined.

DESCRIPTION OF ILLUSTRATIVE EMBODIMENTS

Figure 1:
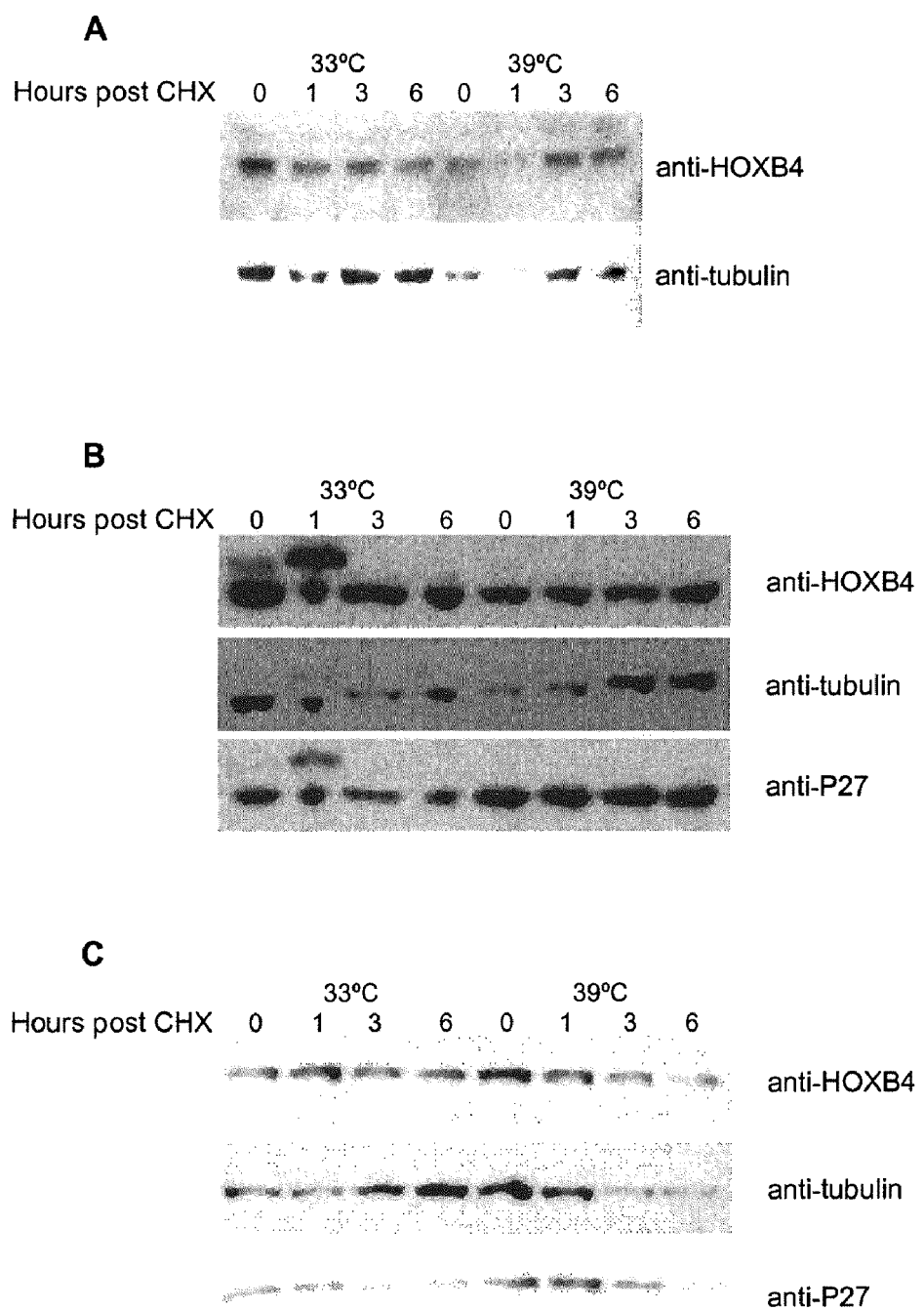
FIG. 1 presents results showing that HOXB4 is degraded by the ubiquitin-proteasome pathway. (A) Baf3 cells were infected with retrovirus containing HOXB4-FLAG. Cells were treated with the proteasome inhibitor MG132 or Dimethyl sulfoxide (DMSO) 30 mn prior the addition of cycloheximide (CHX) to the medium for indicated times. The amount of Tubulin and HOXB4-FLAG-tagged proteins in each lane were measured using the STORM™ 860 and the ImageQuant™ 5.0 program (Molecular Dynamics, Sunnyvale, Calif.). (B) E1-mutant ts20 cells engineered to express HOXB4 protein were grown at permissive and non-permissive temperature, 33 and 39° C. for 18 hours, before starting CHX chase experiments. The amount of Tubulin and HOXB4-FLAG-tagged proteins in each lane were measured using the Luminescent image analyzer LAS3000™ and the Multi Gauge™ V2.3 program (Fujifilm)

Amino acid deletions and substitutions HOXB4 (Δ1-31), Phe6→Ala, Leu7→Ala, Tyr23→Ala and Tyr28→Ala were performed in the HOXB4 protein in order to decrease its degradation. These modifications increased the intracellular stability of HOXB4 protein compared to wild type HOXB4 (wt HOXB4). The ability of mutated HOXB4 protein to favour expansion of hematopoietic progenitors and HSCs was first examined in cultures initiated with 10% wt HOXB4-GFP, 10% mutated HOXB4-YFP expressing cells and 80% non-transduced cells. After an 18-day culture, the proportion of HOXB4 (Leu7→Ala) and Hoxb4 (Tyr23→Ala) cells increased to 50-60% in comparison to 30% for wt HOXB4 ($p<0.05$), and no difference between the proliferation of Hoxb4 (Tyr28→Ala) and wt HOXB4 cells could be identified. Western blot analyses showed that HOXB4 (Leu7→Ala) and HOXB4 (Tyr23→Ala) cells expressed ~4-fold higher and HOXB4(Tyr28→Ala) cells ~8-fold lower levels of Hoxb4 protein than wt HOXB4 cells. The long-term reconstituting ability of these constructs was then evaluated in vivo using competitive repopulation assays. At 8 weeks after transplantation, HOXB4(Leu7→Ala) and HOXB4 (Tyr23→Ala) contributed to 11.5±2 and 13.1±1.8% of peripheral blood leukocytes (PBL) compared to 26.2±4.3% determined for wt HOXB4, while after 16 weeks the progeny of wt HOXB4 cells generated the majority ($\geq 65\%$) of the transplant-derived PBL in all recipients. Likewise, 16 weeks post transplantation HOXB4 positive cells represented $\geq 80\%$ of bone marrow, while cells expressing mutated HOXB4 were present at ~10-12% level. Flow cytometry analysis of bone marrow, spleen and thymus revealed that mutated HOXB4, like wt HOXB4 was expressed by all hematopoietic lineages, and that repopulation differences observed between mutated and wt HOXB4 expressing cells were almost entirely attributable to myeloid lineage cells. However, short-term, non-competitive repopulation experiments showed that in the first 4 weeks post transplantation, mutated HOXB4 expressing progenitors had a significantly greater contribution to the PBL recovery in comparison to wt HOXB4 (range 50-70% vs. 16-30%, respectively; $p<0.05$) for all three tested mutant proteins. Interestingly, this difference became less pronounced and non-significant after week 8 post transplantation. Together, these studies strongly suggest that different intracellular levels of HOXB4 protein are affecting different types of hematopoietic progenitors. Early ex vivo expansion of clonogenic progenitors was achieved with mutated HOXB4 proteins without impairing HSC long-term reconstituting ability. Thus, mutated HOXB4 represents a useful tool to accelerate engraftment after HSC transplantation.

The present invention is illustrated in further details by the following non-limiting examples.

Example 1

Material and Methods for Examples 2-6 Below

Animals

Bone marrow donor mice (C57Bl/6Ly-pep3B×C3H/HeJ) F1 and congenic recipients (C57Bl/6J×C3H/HeJ)F1 were housed and handled in accordance with the guidelines of the Clinical Research Institute of Montreal.

Retroviral Vectors

Generation of the MSCV-IRES-GFP (No 728), MSCV-HOXB4-IRES-GFP (No 812) were described previously (Beslu, 2004). To generate MSCV-HOXB4-FLAG-IRES-GFP cDNA HOXB4-FLAG was subcloned from MSCV-HOXB4-FLAG-PGK-neo (830) in MSCV-IRES-GFP upstream of the IRES (No 1171).

Deletion of the 31 N-terminal amino acids was generated by replacing the 5' 105 bp EcoRI-SmaI fragment of HOXB4 cDNA with an oligonucleotide containing a Kozac sequence and ATG, and the sequences were verified by sequencing. In practice, 35 amino acids in the N-terminal region were thus deleted.

HOXA9 cDNA was subcloned upstream and in frame of FLAG epitope in pCMV-Tag expression vector (Stratagene, La Jolla, Calif.). Fusion protein comprising the N-terminal 31 amino acids of HOXB4 in N-terminal extremity HOXA9 were generated by introducing the 105 bp EcoRV-SmaI fragment of HOXB4 cDNA in frame of HOXA9-FLAG tagged ATG.

Retroviral vectors encoding wild type and fusion HOXA9-FLAG were generated by subcloning the corresponding cDNA in MSCV-PGK-GFP upstream of the PGK-GFP cassette (MSCV-HOXA9-FLAG-PGK-GFP No. 1696 and MSCV-B4HOXA9-FLAG-PGK-GFP No. 2111).

The 660 nt SmaI-NotI fragment of HOXB4 were removed and replaced with the full GFP cDNA SmaI-NotI of GFP to generate the fusion protein HOXB4(1-31)-GFP. Retrovirus vectors encoding wild type and fusion GFP were generated by subcloning the corresponding cDNA in MSCV-PGK-neo$^r$ upstream to the PGK-neo$^r$ cassette (MSCV-HOXA9-GFP-PGK-neo$^r$ No 1696 and MSCV-B4GFP-PGK-neo$^r$).

Retroviral Infection of Cell Lines and Primary Bone Marrow Cells

Baf/3, CHO, TS20, BalbC 3T3 were cultured as described previously (Beslu, 2004, Coulombe, 2003). Retroviral infection of these cell lines was performed by culturing them with a retroviral soup obtained from VSV cell lines (Ory, 1996). Infected cells were sorted for their GFP expression.

Generation of retrovirus producing GP+E86 cells and infection of bone marrow cells were performed as previously described (Kroon, 2001). High-titer, helper-free GP+E-86 producer cells were generated by infection with viral supernatant obtained from transfected VSV-G cells. Bone marrow cells were harvested, pre-stimulated and infected through co-cultivation with these GP+E-86 cells.

Protein Biochemistry Methods

Protein lysates, western blots and pulse chase assays were performed as previously described (Beslu Blood 2004).

MG132 was provided by Biomol and was used at a concentration of 50 µM. Cycloheximide was obtained from SIGMA, and was used at 100 mg/ml and 50 mg/ml for 6-8 hours and 30 hours kinetic, respectively.

Commercial antibodies were supplied by Stratagen for anti-FLAG, by Developmental Studies Hybridoma Bank, University of Iowa for anti-HOXB4, by Sigma for anti-β-tubulin, by BD Biosciences for anti-GFP, and by Santa Cruz Biotechnology for horseradish peroxydase-conjugated anti-mouse, anti-rat and anti-rabbit antibody.

In Vitro Proliferation of Primary Bone Marrow Cells

Transduced bone marrow cells (GFP$^+$) were sorted as described (Beslu Blood 2004). Following a 1-day recovery period, liquid culture was initiated by resuspending with $10^5$ cells/mL in IMDM with 15% of FCS and 10 ng/mL IL-3. After indicated periods of growth, the viable (trypan blue negative) cells were counted and diluted with fresh media so that cell density was maintained between $5 \times 10^4$ and $5 \times 10^5$ cells/mL. At the same points in time, suitable aliquots of cultures were plated in methylcellulose containing 10 ng/mL of IL-3, 10 ng/mL of IL-6, 50 ng/mL of SCF and 5 U/mL of Epo. Colonies were scored on day 10. To determine the in vitro competitive proliferation potential of the transduced cells, cultures comprising 10% GFP$^+$ plus 90% non-transduced competitors, generated as described (Krosl, 2003), were initiated at density $5 \times 10^4$ cells/mL, and the relative contents of GFP$^+$ cells after 6 and 11 day incubations were determined by flow cytometry. Methylcellulose and COS cell supernatant-derived cytokines used for these experiments were prepared and quantitated at IRCM. All other media components were purchased from GIBCO/Invitrogen Corp. (Burlington, ON, Canada).

Generation of Bone Marrow Transplantation Chimeras

Recipient mice were irradiated with 850 cGy (160 cGy/min, $^{137}$Cs γ-source. J.L., Shepherd, Calif.). To generate groups of control GFP$^+$, or HOXB4(Δ1-31)GFP$^+$ or wt HOXB4GFP$^+$ recipients, 10% of transduced bone marrow cells (GFP$^+$) recovered from co-cultures with retroviral producers were transplanted with non-transduced competitors ($4 \times 10^5$ cells/recipient). Proportions of transduced cells (GFP$^+$) that contribute to hematopoietic repopulation of transplanted mice were determined by flow cytometry.

Southern Blot Analysis

Southern blot analyses were performed as described previously (Beslu, 2004). The probes used were 0.73 kb GFP cDNA, and 1.4 kb erythropoietin receptor cDNAs, labelled with $^{32}$P by random primer extension.

Example 2

The Ubiquitin-Proteasome Pathway Degrades HOXB4 Protein

It has been previously shown that HOXB4 has a high turnover rate (Krosl, 2003, Beslu, 2004). In order to identify mechanisms implicated in HOXB4 degradation, Flag tagged HOXB4 was expressed by retroviral infection in Baf/3 hematopoietic cell line. The effect of a proteasome inhibitor, MG132, on the half-life of ectopic HOXB4 was first evaluated after shutting off protein synthesis with cycloheximide. As shown in FIG. 1A, in absence of MG132, the half-life of HOXB4 protein is around 1 hour, in sharp contrast, addition of MG132 to the media prolonged HOXB4 protein levels in Baf/3 cells for greater than 6 hours. This result suggests that HOXB4 protein is degraded by the proteasome.

Although most proteasomal substrates must be ubiquitinated before being degraded, there are some exceptions to this general rule, especially when the proteasome plays a normal role in the post-translational processing of the protein. The proteasomal activation of NF-κB by processing p105 into p50 via internal proteolysis is one major example. Some proteins that are hypothesized to be unstable due to intrinsically unstructured regions, are degraded in a ubiquitin-independent manner. The most well-known example of a ubiquitin-independent proteasome substrate is the enzyme ornithine decarboxylase. Ubiquitin-independent mechanisms targeting key cell cycle regulators such as p53 have also been reported, although p53 is also subject to ubiquitin-dependent degradation. Finally, structurally-abnormal, misfolded, or highly oxidized proteins are also subject to ubiquitin-independent and 19S-independent degradation under conditions of cellular stress.

Figure 2:
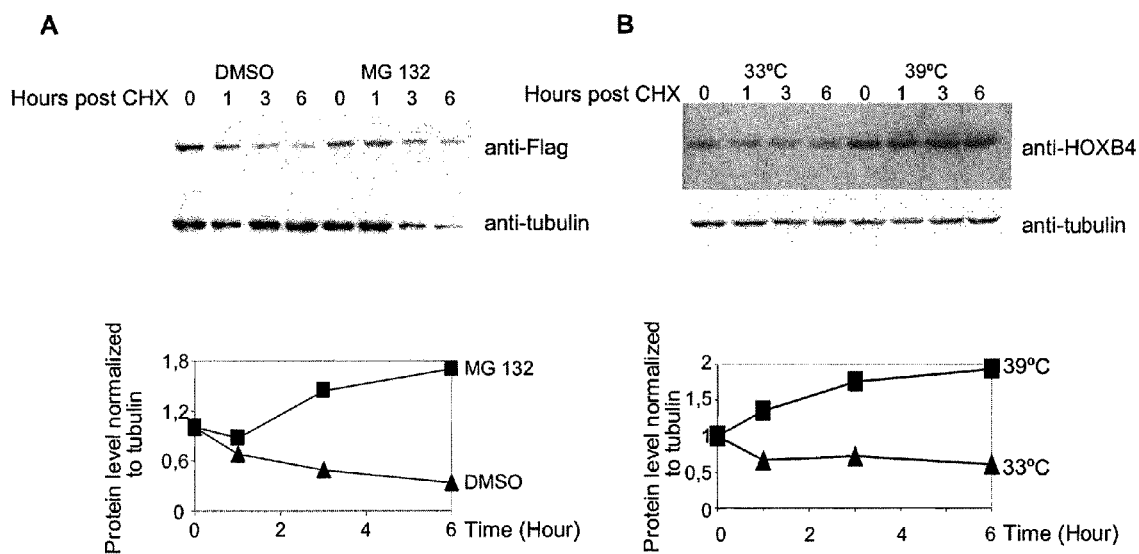
FIG. 2 presents in Panel A) BalbC3T3 (parental cells for E1-mutant ts20 cells) engineered to express HOXB4 protein were grown at permissive and non-permissive temperatures, 33 and 39° C. for 18 hours, before starting CHX chase experiments. The amount of Tubulin and HOXB4-FLAG-tagged proteins were determined by western blot analysis. Panel B) Nedd8-mutant ts41 cells engineered to express HOXB4 protein were grown at permissive and non-permissive temperatures, 33 and 39° C. for 18 hours, before starting CHX chase experiments. The amount of Tubulin, HOXB4-FLAG-tagged and p27 proteins was determined by western blot analysis. P27 was used as positive control of this experiment. Panel C) Same experiment as in B) with CHO cells (parental cells for ts41 cells)

In order to confirm that proteasome degradation of HOXB4 was ubiquitin-dependent, ts20 cell line that harbors a temperature sensitive allele of the ubiquitin-activating enzyme E1 (Chowdary MCB 1994) was used to test if HOXB4 protein is ubiquitinated before degradation. For this purpose, HOXB4 was over expressed in ts20 cell line and a cycloheximide chase experiment was performed over 6 hours at permissive (33° C.) and non-permissive (39° C.) temperature. At the permissive temperature, when the E1 enzyme is active, HOXB4 is rapidly degraded, but upon rising the temperature to the non-permissive condition, an accumulation of the HOXB4 protein and an increase of its stability were observed (FIG. 1B). Moreover, it was shown that there is no temperature-dependent upregulation of ectopic HOXB4 in parental cells (FIG. 2A). Thus, HOXB4 protein degradation requires a functional ubiquitin conjugation pathway. The HOXA9 protein, which also promotes HSC expansion (Lawrence, 1997, Thorsteinsdottir, 2002), has been shown to be regulated by cullin 4A (Zhang, 2003). Cullins belong to the superfamily of E3 ubiquitin ligase named Cullin-RING-ligases (CRLs), and their activity is dependent on neddylation by Nedd8 (reviewed in Petroski, Nature review 2005).

To further study HOXB4 protein degradation process, HOXB4 was over expressed in ts41 cell line, in which neddylation of cullin by nedd8 is blocked at non-permissive temperature (39° C.) (Ohh, 2002), and in CHO as parental cell line. These aforementioned cell lines where subjected to cycloheximide at both 33° C. and 39° C., no differences were observed between the two temperatures regarding HOXB4 protein levels (FIG. 2B-C). In contrast to HOXA9, HOXB4 degradation is a cullin independent mechanism.

Example 3

Generation of a More Stable HOXB4 Protein

In order to get more insight into the HOXB4 protein regulation sequence, alignment analyses were performed, which revealed that in addition to the homeodomain per se, the 31 N-terminal amino acid region is also highly conserved among members of the $4^{th}$ paralog (FIG. 3A). Moreover, this segment is conserved through evolution, as shown by protein sequence similarities between HOXB4 and Deformed (Dfd), its fly homologue (FIG. 3B).

Figure 4:
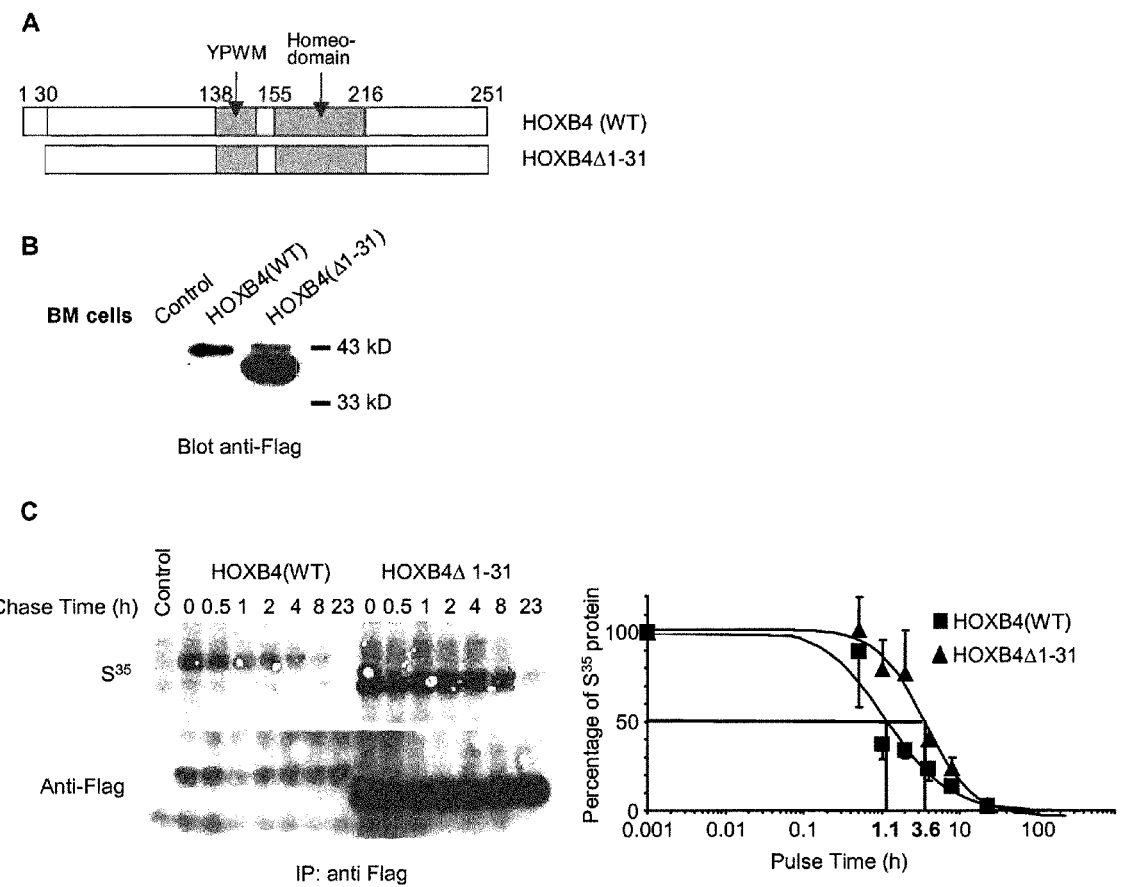
FIG. 4 presents a schematic representation of wt HOXB4 and HOXB4(Δ1-31) (Panel A). Panel B presents a western blot analysis performed on bone marrow cells engineered to over express WT and mutant HOXB4 protein Flag tagged after 7 days of culture. Panel C presents pulse chase analysis of wt HOXB4 and HOXB4(Δ1-31) proteins performed on transduced BaF3 cells. Each protein level was determined as described in FIG. 1. The half-life was calculated from the proportions of radioactive proteins at the indicated time points using AllFit™ (© Charles and Andre Lean, University of Montreal, QC)

To further study the role of the HOXB4 N-terminal region, these 31 amino acids were deleted (FIG. 4A) and wild type HOXB4 (WT) and flag tagged mutant (Δ1-31) were expressed by retroviral infection in primary bone marrow cells. Western blot performed with Flag antibody revealed that the deleted form of HOXB4 protein is expressed at higher level than wild type protein (FIG. 4B), this phenomenon was observed also in different cell lines like Baf/3, Cos, HEK293T. The half-life of both proteins was then evaluated by pulse chase experiments. In comparison to the previously reported HOXB4 half-life (~1 hour) (Krosl, 2003, Beslu, 2004), deletion of the N-terminal amino acids increased the half-life of the protein to between 3 and 4 hours (FIG. 4C). Thus, the short intra-cellular HOXB4 protein half-life is linked to the 31 N-terminal amino acids region.

Example 4

The 31 N-Terminal Amino Acids of HOXB4 Encompass a Degron

Figure 5:
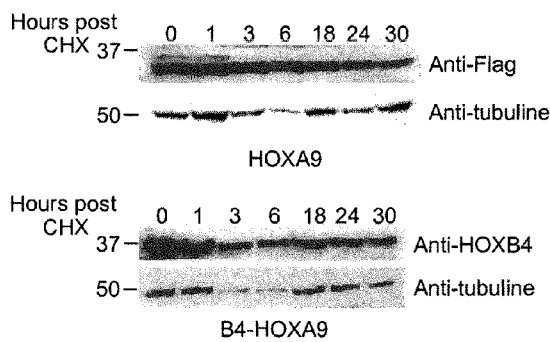
FIG. 5 presents a comparison of protein stability of HOXA9 versus B4-HOXA9 and GFP versus B4-GFP (in Panels A and B, respectively), measured by CHX chase experiments. Each protein level was determined as described in FIG. 1. ●, indicates wild type protein HOXA9 in (A) and GFP in (B) and ■ indicates fusion protein B4-HOXA9 in (A) and B4-GFP in (B)
Figure 5:
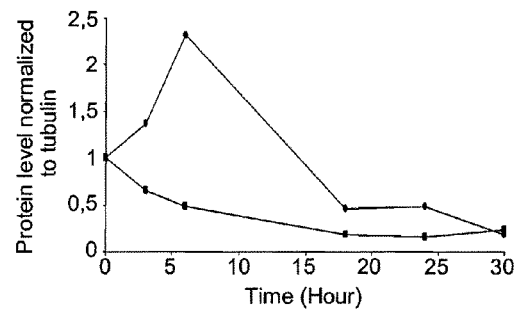
Figure 5:
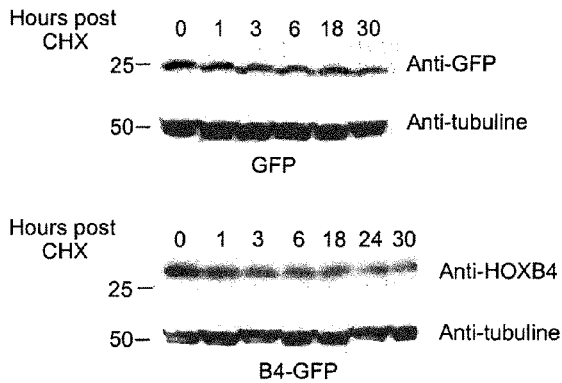
Figure 5:
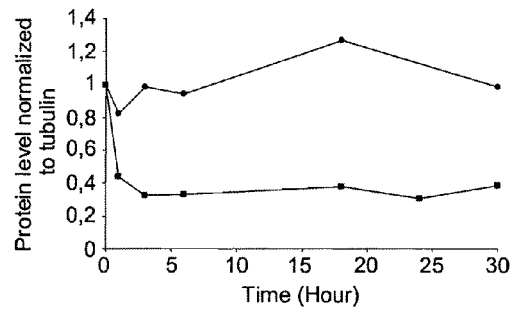

Since the N-terminal domain of HOXB4 is necessary for the rapid degradation of the protein, it was assessed whether it is sufficient to induce destabilization. For this purpose, a protein consisting of a fusion of the 35 N-terminal amino acid region of HOXB4 to the Flag-tagged HOXA9 protein (B4-HOXA9) was first generated. Flag-tagged HOXA9 and the fusion protein B4-HOXA9 were expressed by retroviral infection in CHO cell lines, and the cells subjected to cycloheximide chase experiments in order to determine the impact of the added amino acids stretch on a homeodomain protein stability. B4-HOXA9 displayed a much reduced half-life as compared to HOXA9 (>20 vs. <10 hours) (FIG. 5A). In order to determine if the instability conferred by the 35 N-terminal amino acids required a homeodomain context, these amino acids were then fused at the N-terminal extremity of the GFP protein (B4-GFP). As for HOXA9, cycloheximide assays were performed on CHO cells infected with retroviruses containing either GFP or B4-GFP fusion protein. These experiments revealed that the highly stable protein GFP (Corish protein engineering 99) is rapidly degraded upon addition of the N-terminal amino acids of HOXB4 (FIG. 5B).

Example 5

Effect of the Truncated Form of HOXB4 In Vitro on Primary Bone Marrow Cells

The functionality of the N-terminal truncated HOXB4 was then assessed. The effect of the truncated HOXB4 protein on primary bone marrow cells (i.e. obtained from the animal as opposed to cell lines bone marrow cells) was thus evaluated.

Retroviruses containing either wt HOXB4-GFP, HOXB4 (Δ1-31)-GFP, or GFP alone as control were used to infect primary bone marrow cells as described in Example 1.

Figure 6:
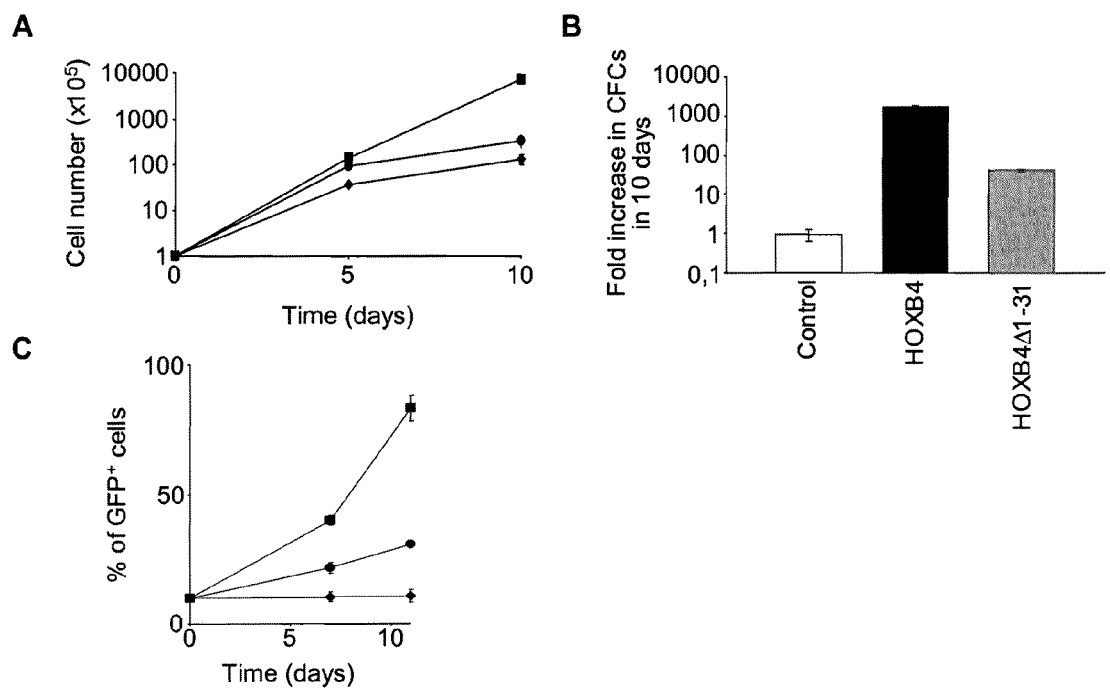
FIG. 6 presents results of the expansion of total nucleated cells over a 10 day period in cultures initiated with sorted GFP⁺ cells. ■, wt HOXB4; ●, HOXB4(Δ 1-31); ♦, control GFP. Results represent mean value±SD of a representative experiment (n=3) performed in duplicate (Panel A). Panel B presents in vitro expansion over a 10 day period of myeloid CFCs derived from the indicated populations of transduced BM cells. Results represent mean values±SD of a representative experiment (n=2) performed in quadruplicate cultures. Black bar, HOXB4 cells; Grey bar, HOXB4(Δ 1-31) cells; white bar, GFP cells. Panel C presents results of expansion of GFP⁺ cells in liquid cultures initiated with 10% GFP⁺ (wt HOXB4⁺, ■; or HOXB4(Δ1-31)⁺, ●; or control GFP⁺, ♦) cells, and 90% non-transduced competitors. Results represent mean values±SD of a representative experiment (n=3) performed in duplicate.

Proliferation assays performed with GFP$^+$ sorted bone marrow cells, revealed that the total number of HOXB4(Δ1-31) cells increased 3-fold over GFP control cells, while wt HOXB4 cell number increased more than 50-fold compared to control over a 10 day period (FIG. 6A). During this 10 day expansion period, the myeloid clonogenic progenitor (CFC) frequency increased more than 1000-fold, and 45-fold over initial numbers for wt HOXB4 CFCs and HOXB4(Δ1-31) CFCs, respectively. No increase was obtained for control GFP CFCs (FIG. 6B). Also, both wt HOXB4 and HOXB4 (Δ1-31) enabled the expansion of multipotent clonogenic progenitor (CFU-GEMM), but not in GFP control culture (data not shown). Applicant also assessed whether the truncated HOXB4 conferred a competitive growth advantage to bone marrow cells. In cultures initiated with 10% GFP+ cells (GFP control, wt HOXB4+ and HOXB4(Δ1-31)+) and 90% untransduced cells, the proportion of wt HOXB4 and HOXB4 (Δ1-31) increased within 11 days to 83.5%±4.9 and 30.8±0, respectively while no increase could be detected for GFP+ control cells (FIG. 6C). Together these results suggested that the truncated HOXB4 protein is able to sustain expansion of total bone marrow cells and myeloid progenitors in vitro, but this protein appears to be less efficient than the wild type protein.

Example 6

HOXB4(Δ1-31) Confers a Highly Competitive Hematopoietic Reconstitution Advantage to Transduced HSC It was then assessed whether the truncated form of HOXB4 is able to increase the in vivo repopulation capacity of transduced cells compare to untransduced cells, with the same efficiency as wild type HOXB4.

Figure 7:
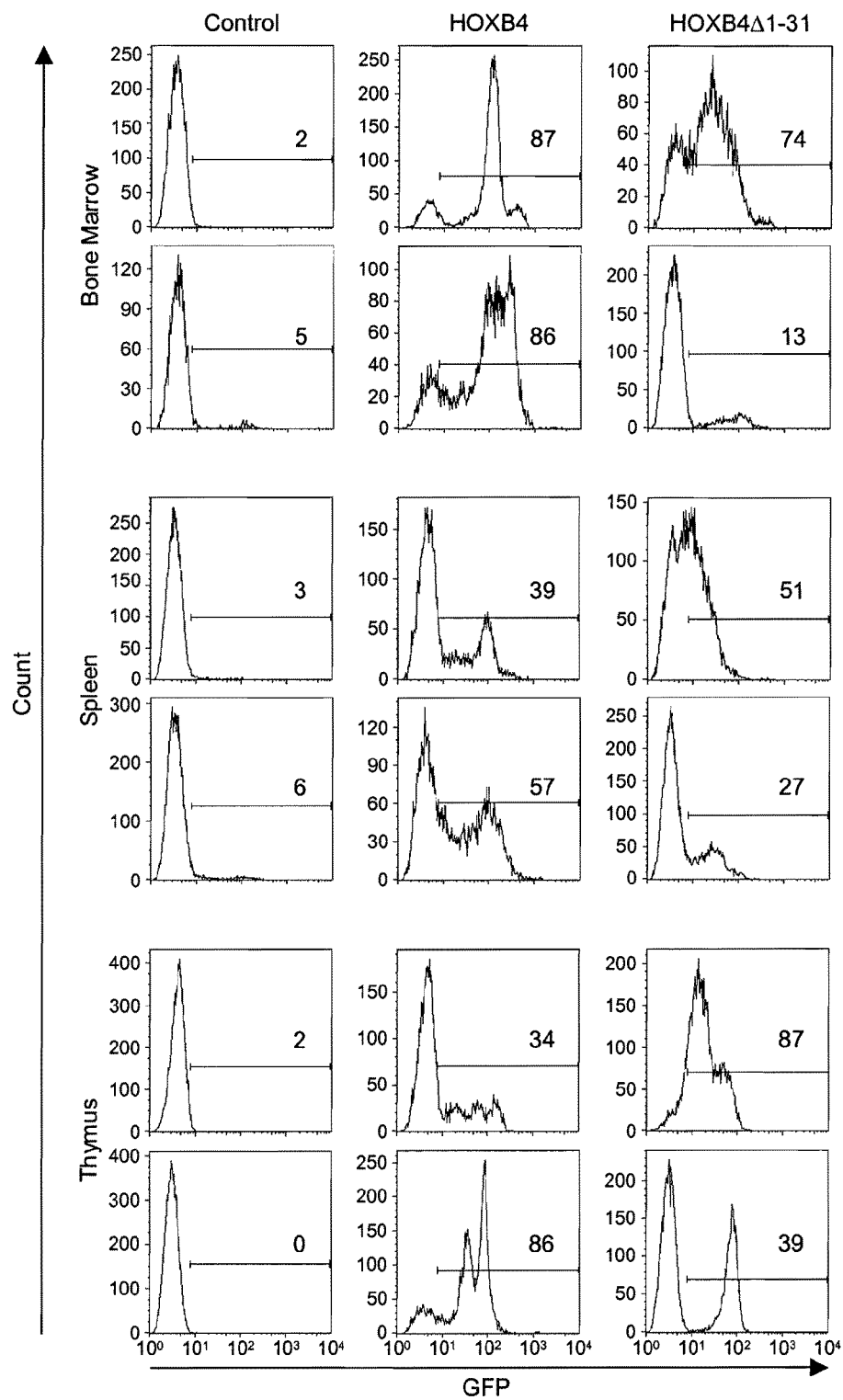
FIG. 7 presents the hematopoietic reconstitution induced by HOXB4(Δ1-31). Flow cytometric analysis of BM (upper panels), splenic (middle panels) and thymic (lower panels) cell populations of mice transplanted with comparable numbers of GFP⁺ control (left panels), or wt HOXB4 (middle panels), or HOXB4(Δ1-31)-transduced BM cells (right panels). Proportions of GFP⁺ cells populations were determined for recipients sacrificed at 12 weeks post transplantation. Results for 2 representative mice out of 4 per group were shown.

Three groups of BM transplantation chimeras were thus generated by injecting a mixture of 10% GFP+ cells (wt HOXB4+, HOXB4(Δ1-31)+, or control GFP+) together with 90% untransduced competitors in sublethally irradiated recipients. Contribution of the bone marrow graft-derived GFP+ cells to hematopoietic reconstitution was determined 12 weeks post-transplantation by flow cytometry analysis. As expected, for each hematopoietic tissue, GFP+ control cells showed no proliferation advantage (FIG. 7 left column). In contrast, both wt HOXB4+ and HOXB4(Δ1-31)+ cells out competed the 90% untransduced cells in their reconstitution ability of bone marrow, spleen and thymus (FIG. 7 middle and right columns), as well as for peripheral blood. Importantly, no significant difference was observed between wt HOXB4+ and HOXB4(Δ1-31)+ cells in their hematopoietic repopulation capacity, indicating that the truncated form of HOXB4 retains its full biological activity in vivo.

Figure 8:
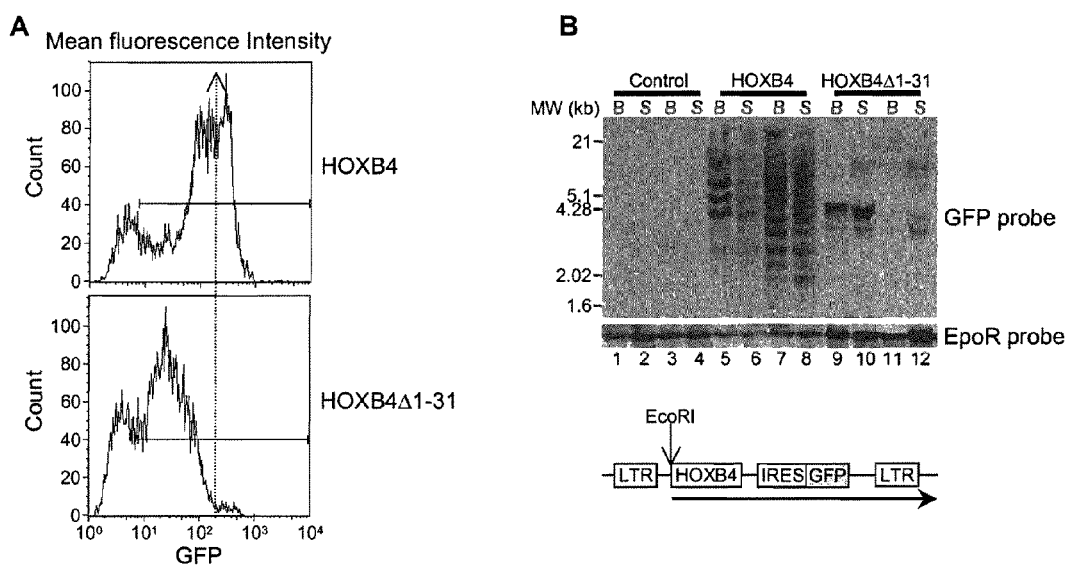
FIG. 8 presents examples of bone marrow facs profiles from mice transplanted with wt HOXB4 (upper panel) or HOXB4(Δ1-31) (lower panel). These examples revealed a log difference of the mean fluorescence intensity between both (panel A). Panel B presents a representative Southern blot analysis of proviral integration patterns in bone marrow (B) and spleen (S), isolated from recipients of control GFP, wt HOXB4, or HOXB4(Δ1-31)-transduced BM cells presented in FIG. 7. DNA was digested with EcoRI, which cuts once within the integrated provirus, such that each band represents a unique integration event on blots probed with GFP. Erythropoietin receptor (EpoR)-derived signal is representative of DNA loading.

The flow cytometry profiles revealed however an important difference between wt HOXB4+ and HOXB4(Δ1-31)+ cells: the mean fluorescence intensity was systematically one log lower for HOXB4(Δ1-31)+ cells compare to wt HOXB4+ cells (see FIG. 8A for one example). Since the GFP gene in the retrovirus used is under the control of an internal ribosomal entry site for its expression, the mean fluorescence intensity of GFP reflects the expression level of wt HOXB4, or HOXB4(Δ1-31). This observation suggests that in recipients reconstituted by HOXB4(Δ1-31)+ cells, there was a selection for hematopoietic transduced cells that expressed low level of the HOXB4 truncated protein. This hypothesis was confirmed by determining the number of cellular clones that contributed to hematopoietic repopulation. For this purpose, proviral integrations of genomic DNA isolated from bone marrow and spleen of transplanted recipients were assessed by southern blot analyses. As expected, in wt HOXB4 recipients multiple proviral integrations with different signal intensities revealed the activity of several independent clones in these mice (FIG. 8B, lanes 5-8). In contrast, for HOXB4(Δ1-31) recipients, only two or three independent clones contributed to the hematopoietic reconstitution (FIG. 8B, lanes 9-12). The fact that the same band (same retroviral integration and thus same clone) can be seen in different hematopoietic tissues shows that the clone is a HSC. This is in agreement with in vivo selection of cells with low expression levels of the HOXB4 (Δ1-31) protein.

Together, the results presented above show that HOXB4 protein is degraded by the ubiquitin-proteasome pathway. The N-terminal amino acids region of the HOXB4 protein is identified as a destabilizing domain, which is both necessary and sufficient for protein destabilization. Moreover, this domain is dispensable for HOXB4 induced hematopoietic repopulation. It is also expected that since the 31 N-terminal amino acid region is also highly conserved among members of the 4$^{th}$ paralog (Figure A), that the other paralogs HOXA4, HOXC4, HOXD4 are also degraded by the ubiquitin-proteasome pathway and that they could thus be modified to include mutations that would reduce their susceptibility to the ubiquitin-proteasome. It is also expected that specific mutations disclosed herein would stabilize these paralogs. These stabilized proteins could then be advantageously used. In particular, HOXA4 and HOXC4 which are also known to be involved in hematopoiesis could also be used in expansion procedures.

Example 7

Material and Methods for Examples 8 to 12 Below

Animals

Bone marrow donors were 20-40 week old male and female B6/SJL mice (The Jackson Laboratory, Bar Harbor, Me., USA) and C57Bl/6 mice, 12 weeks of age (Jackson) were used as bone marrow recipients. All the mice were housed in our research center animal facility according to Maisonneuve-Rosemont Hospital research center animal safety committee guidelines.

Retroviral Vectors and Point Mutations

All gene transfer experiments were performed using MSCV vector containing an internal ribosomal entry sequence (IRES) followed by enhanced green fluorescent protein (eGFP) or enhanced yellow fluorescent protein (eYFP). The wt HOXB4 vector carried a cDNA encoding a full length HOXB4 protein. Point mutations including F6→A, L7→A (#1423), Y23→A (#1426) and Y28→A (#1427) in the N-terminal domain of Hoxb4 were generated by replacing the nucleotides encoding amino acids 1-35 of the wild type Hoxb4 cDNA with annealed double stranded oligonucleotides carrying the desired mutations. The oligonucleotide sequences are presented in Table 1 below.

TABLE 1

| | | |
|---|---|---|
| Phe-Ala#6sens | 5'AATTCCCACC *ATG* GCT ATG AGT TCT GCT TTG ATC AAC TCA AAC TAT GTC GAC CCC AAG TTC CCT CCA TGC GAG GAA TAT TCA CAG AGC GAT TAC CTA CCC AGC GAC CAC TCG CCC 3' | (SEQ ID NO: 33) |
| Phe-Ala#6a/s | 5'GGG CGA GTG GTC GCT GGG TAG GTA ATC GCT CTG TGA ATA TTC CTC GCA TGG AGG GAA CTT GGG GTC GAC ATA GTT TGA GTT GAT CAA AGC AGA ACT CAT AGC CAT GGT GGG3' | (SEQ ID NO: 34) |
| Leu-Ala#7sens | 5'AATTCCCACC *ATG* GCT ATG AGT TCT TTT GCT ATC AAC TCA AAC TAT GTC GAC CCC AAG TTC CCT CCA TGC GAG GAA TAT TCA CAG AGC GAT TAC CTA CCC AGC GAC CAC TCG CCC 3' | (SEQ ID NO: 35) |
| Leu-Ala#7a/s | 5'GGG CGA GTG GTC GCT GGG TAG GTA ATC GCT CTG TGA ATA TTC CTC GCA TGG AGG GAA CTT GGG GTC GAC ATA GTT TGA GTT GAT AGC AAA AGA ACT CAT AGC CAT GGT GGG3' | (SEQ ID NO: 36) |

TABLE 1-continued

```
Tyr-Ala#12sens  5' AATTCCCACC ATG GCT ATG AGT TCT TTT    (SEQ ID NO: 37)
                TTG ATC AAC TCA AAC GCT GTC GAC CCC
                AAG TTC CCT CCA TGC GAG GAA TAT TCA
                CAG AGC GAT TAC CTA CCC AGC GAC CAC
                TCG CCC3'

Tyr-Ala#12a/s   5'GGG CGA GTG GTC GCT GGG TAG GTA       (SEQ ID NO: 38)
                ATC GCT CTG TGA ATA TTC CTC GCA TGG
                AGG GAA CTT GGG GTC GAC AGC GTT TGA
                GTT GAT CAA AAA AGA ACT CAT AGC CAT
                GGT GGG3'

Val-Ala#13sens  5'AATTCCCACC ATG GCT ATG AGT TCT TTT     (SEQ ID NO: 39)
                TTG ATC AAC TCA AAC TAT GCT GAC CCC
                AAG TTC CCT CCA TGC GAG GAA TAT TCA
                CAG AGC GAT TAC CTA CCC AGC GAC CAC
                TCG CCC3'

Val-Ala#13a/s   5'GGG CGA GTG GTC GCT GGG TAG GTA        (SEQ ID NO: 40)
                ATC GCT CTG TGA ATA TTC CTC GCA TGG
                AGG GAA CTT GGG GTC AGC ATA GTT TGA
                GTT GAT CAA AAA AGA ACT CAT AGC CAT
                GGT GGG3'

Asp-Ala#14sens  5' AATTCCCACC ATG GCT ATG AGT TCT TTT    (SEQ ID NO: 41)
                TTG ATC AAC TCA AAC TAT GTC GCT CCC
                AAG TTC CCT CCA TGC GAG GAA TAT TCA
                CAG AGC GAT TAC CTA CCC AGC GAC CAC
                TCG CCC3'

Asp-Ala#14a/s   5'GGG CGA GTG GTC GCT GGG TAG GTA        (SEQ ID NO: 42)
                ATC GCT CTG TGA ATA TTC CTC GCA TGG
                AGG GAA CTT GGG AGC GAC ATA GTT TGA
                GTT GAT CAA AAA AGA ACT CAT AGC CAT
                GGT GGG3'

Lys-Ala#16sens  5' AATTCCCACC ATG GCT ATG AGT TCT TTT    (SEQ ID NO: 43)
                TTG ATC AAC TCA AAC TAT GTC GAC CCC
                GCT TTC CCT CCA TGC GAG GAA TAT TCA
                CAG AGC GAT TAC CTA CCC AGC GAC CAC
                TCG CCC3'

Lys-Ala#16a/s   5'GGG CGA GTG GTC GCT GGG TAG GTA        (SEQ ID NO: 44)
                ATC GCT CTG TGA ATA TTC CTC GCA TGG
                AGG GAA AGC GGG GTC GAC ATA GTT TGA
                GTT GAT CAA AAA AGA ACT CAT AGC CAT
                GGT GGG3'

Phe-Ala#17sens  5' AATTCCCACC ATG GCT ATG AGT TCT TTT    (SEQ ID NO: 45)
                TTG ATC AAC TCA AAC TAT GTC GAC CCC
                AAG GCT CCT CCA TGC GAG GAA TAT TCA
                CAG AGC GAT TAC CTA CCC AGC GAC CAC
                TCG CCC3'

Phe-Ala#17a/s   5'GGG CGA GTG GTC GCT GGG TAG GTA        (SEQ ID NO: 46)
                ATC GCT CTG TGA ATA TTC CTC GCA TGG
                AGG AGC CTT GGG GTC GAC ATA GTT TGA
                GTT GAT CAA AAA AGA ACT CAT AGC CAT
                GGT GGG3'

Tyr-Ala#23sens  5' AATTCCCACC ATG GCT ATG AGT TCT TTT    (SEQ ID NO: 47)
                TTG ATC AAC TCA AAC TAT GTC GAC CCC
                AAG TTC CCT CCA TGC GAG GAA GCT TCA
                CAG AGC GAT TAC CTA CCC AGC GAC CAC
                TCG CCC3'

Tyr-Ala#23a/s   5'GGG CGA GTG GTC GCT GGG TAG GTA        (SEQ ID NO: 48)
                ATC GCT CTG TGA AGC TTC CTC GCA TGG
                AGG GAA CTT GGG GTC GAC ATA GTT TGA
                GTT GAT CAA AAA AGA ACT CAT AGC CAT
                GGT GGG3'

Tyr-Ala#28sens  5' AATTCCCACC ATG GCT ATG AGT TCT TTT    (SEQ ID NO: 49)
                TTG ATC AAC TCA AAC TAT GTC GAC CCC
                AAG TTC CCT CCA TGC GAG GAA TAT TCA
                CAG AGC GAT GCT CTA CCC AGC GAC CAC
                TCG CCC3'
```

TABLE 1-continued

| | | |
|---|---|---|
| Tyr-Ala#28a/s | 5'GGG CGA GTG GTC GCT GGG TAG AGC ATC GCT CTG TGA ATA TTC CTC GCA TGG AGG GAA CTT GGG GTC GAC ATA GTT TGA GTT GAT CAA AAA AGA ACT CAT AGC CAT GGT GGG3' | (SEQ ID NO: 50) |
| Leu-Ala#29sens | 5' AATTCCCACC ATG GCT ATG AGT TCT TTT TTG ATC AAC TCA AAC TAT GTC GAC CCC AAG TTC CCT CCA TGC GAG GAA TAT TCA CAG AGC GAT TAC GCT CCC AGC GAC CAC TCG CCC3' | (SEQ ID NO: 51) |
| Leu-Ala#29a/s | 5'GGG CGA GTG GTC GCT GGG AGC GTA ATC GCT CTG TGA ATA TTC CTC GCA TGG AGG GAA CTT GGG GTC GAC ATA GTT TGA GTT GAT CAA AAA AGA ACT CAT AGC CAT GGT GGG3' | (SEQ ID NO: 52) |
| Tyr-Phe#12sens | 5' AATTCCCACC ATG GCT ATG AGT TCT TTT TTG ATC AAC TCA AAC TTC GTC GAC CCC AAG TTC CCT CCA TGC GAG GAA TAT TCA CAG AGC GAT TAC CTA CCC AGC GAC CAC TCG CCC 3' | (SEQ ID NO: 53) |
| Tyr-Phe#12a/s | 5'GGG CGA GTG GTC GCT GGG TAG GTA ATC GCT CTG TGA ATA TTC CTC GCA TGG AGG GAA CTT GGG GTC GAC GAA GTT TGA GTT GAT CAA AAA AGA ACT CAT AGC CAT GGT GGG3' | (SEQ ID NO: 54) |
| Tyr-Phe#23sens | 5' AATTCCCACC ATG GCT ATG AGT TCT TTT TTG ATC AAC TCA AAC TAT GTC GAC CCC AAG TTC CCT CCA TGC GAG GAA TTC TCA CAG AGC GAT TAC CTA CCC AGC GAC CAC TCG CCC 3' | (SEQ ID NO: 55) |
| Tyr-Phe#23a/s | 5'GGG CGA GTG GTC GCT GGG TAG GTA ATC GCT CTG TGA GAA TTC CTC GCA TGG AGG GAA CTT GGG GTC GAC ATA GTT TGA GTT GAT CAA AAA AGA ACT CAT AGC CAT GGT GGG3' | (SEQ ID NO: 56) |
| Tyr-Phe#28sens | 5' AATTCCCACC ATG GCT ATG AGT TCT TTT TTG ATC AAC TCA AAC TAT GTC GAC CCC AAG TTC CCT CCA TGC GAG GAA TAT TCA CAG AGC GAT TTC CTA CCC AGC GAC CAC TCG CCC 3' | (SEQ ID NO: 57) |
| Tyr-Phe#28a/s | 5'GGG CGA GTG GTC GCT GGG TAG GAA ATC GCT CTG TGA ATA TTC CTC GCA TGG AGG GAA CTT GGG GTC GAC ATA GTT TGA GTT GAT CAA AAA AGA ACT CAT AGC CAT GGT GGG3' | (SEQ ID NO: 58) |
| Tyr-Phe#12/23sens | 5' AATTCCCACC ATG GCT ATG AGT TCT TTT TTG ATC AAC TCA AAC TTC GTC GAC CCC AAG TTC CCT CCA TGC GAG GAA TTC TCA CAG AGC GAT TAC CTA CCC AGC GAC CAC TCG CCC 3' | (SEQ ID NO: 59) |
| Tyr-Phe#12/23a/s | 5'GGG CGA GTG GTC GCT GGG TAG GTA ATC GCT CTG TGA GAA TTC CTC GCA TGG AGG GAA CTT GGG GTC GAC GAA GTT TGA GTT GAT CAA AAA AGA ACT CAT AGC CAT GGT GGG3' | (SEQ ID NO: 60) |
| Tyr-Phe#12/28sens | 5' AATTCCCACC ATG GCT ATG AGT TCT TTT TTG ATC AAC TCA AAC TTC GTC GAC CCC AAG TTC CCT CCA TGC GAG GAA TAT TCA CAG AGC GAT TTC CTA CCC AGC GAC CAC TCG CCC 3' | (SEQ ID NO: 61) |
| Tyr-Phe#12/28a/s | 5'GGG CGA GTG GTC GCT GGG TAG GAA ATC GCT CTG TGA ATA TTC CTC GCA TGG AGG GAA CTT GGG GTC GAC GAA GTT TGA GTT GAT CAA AAA AGA ACT CAT AGC CAT GGT GGG3' | (SEQ ID NO: 62) |

TABLE 1-continued

| | | |
|---|---|---|
| Tyr-Phe#23/28sens | 5' AATTCCCACC ATG GCT ATG AGT TCT TTT TTG ATC AAC TCA AAC TAT GTC GAC CCC AAG TTC CCT CCA TGC GAG GAA TTC TCA CAG AGC GAT TTC CTA CCC AGC GAC CAC TCG CCC 3' | (SEQ ID NO: 63) |
| Tyr-Phe#23/28a/s | 5'GGG CGA GTG GTC GCT GGG TAG GAA ATC GCT CTG TGA GAA TTC CTC GCA TGG AGG GAA CTT GGG GTC GAC ATA GTT TGA GTT GAT CAA AAA AGA ACT CAT AGC CAT GGT GGG3' | (SEQ ID NO: 64) |
| Tyr-Phe#12/23/28sens | 5' AATTCCCACC ATG GCT ATG AGT TCT TTT TTG ATC AAC TCA AAC TTC GTC GAC CCC AAG TTC CCT CCA TGC GAG GAA TTC TCA CAG AGC GAT TTC CTA CCC AGC GAC CAC TCG CCC 3' | (SEQ ID NO: 65) |
| Tyr-Phe#12/23/28a/s | 5'GGG CGA GTG GTC GCT GGG TAG GAA ATC GCT CTG TGA GAA TTC CTC GCA TGG AGG GAA CTT GGG GTC GAC GAA GTT TGA GTT GAT CAA AAA AGA ACT CAT AGC CAT GGT GGG3' | (SEQ ID NO: 66) |

Bone Marrow Transduction

Primary high-titer retrovirus was produced by transient transfection of 293 GPG-VSV packaging cells line with the appropriate retroviral vector (MSCV-mutated HOXB4-IRES-GFP or MSCV-wt HOXB4-IRES-YFP). High-titer, helper-free GP+E-86 ectopic producer cells for MSCV-IRES-GFP, MSCV-IRES-HOXB4-YFP and all three mutant HOXB4-GFP genes were generated by infection with viral supernatant obtained from 293 GPG-VSV cells.

Bone marrow cells were obtained from B6/SJL mice 4 days after 5-Fluorouracil(150 mg/kg) injection by flushing both femurs and tibias with cold DMEM (Gibco/Invitrogen, Burlington, ON, Canada) supplemented with 2% fetal bovine serum (FBS) (Hyclone, Logan, Utah, USA). The cells were then cultured for 2 days in bone marrow medium (DMEM with 15% FBS, 5 ng/ml of interleukin-3, 10 ng/ml of interleukin-6, 100 ng/ml of stem cell factor, 50 µg/ml of gentamycin and 10 µg/ml of ciprofloxacin). All cytokines used in these experiments were produced at IRIC (Institut de recherche en immunologic et cancerologie, Montreal, QC, Canada) as COS cell supernatants. Part of the bone marrow cells was co-cultured on non-transduced GP+E-86 cells and served as non-infected cell part of competition studies. After 1 day recovery from co-culture with retroviral producers the proportion of infected cells (GFP or YFP cells) was determined by flow cytometry using FACS/Sort (BD Biosciences, Mississauga, ON Canada).

Competitive Repopulation Assay

10% of wt HOXB4-YFP expressing cells were mixed with 10% of each mutant HOXB4-GFP transduced cells or 10% IRES-GFP (empty vector) cells and 80% of the non-infected cells. The cells were then immediately placed in liquid culture or transplanted into 12 weeks old mice.

Competitive liquid culture was initiated at a density of $3 \times 10^5$ cells per mL in bone marrow medium. Cultures were maintained for 18 days, every 2 days the cells were counted and analysed for the proportion of GFP and YFP positive populations by flow cytometry using FACS Vantage (BD Biosciences, Mississauga, ON Canada).

For in vivo competitive repopulation, a total of $3 \times 10^5$ cells were transplanted intravenously into the sublethaly (850 cGy, $^{137}$Cs γ source) irradiated recipients. Bone marrow, spleens, and peripheral blood were analyzed 4 months later for the contribution to hematopoietic reconstitution by wt HOXB4 and mutated HOXB4 cells using flow cytometry.

Non Competitive Repopulation Assay

25% of transduced cells (GFP only, wt HOXB4 or each mutated HOXB4) were mixed with 75% of non infected cells for a total of $2 \times 10^5$ cells injected in each mouse. Each group (3 mutants, WT, and empty vector) consisted of 5 mice and the same analysis as in the competition assay of the hematopoietic organs was performed.

FACS Analysis of Transplantation

In the competition assay, the mice were sacrificed 4 months post transplantation and the contribution of transplanted infected cells to myeloid and lymphoid population of bone marrow, spleens and peripheral blood was analyzed by staining the cells from each organ with anti-mouse CD11b PE-Cy7 (BD), CD45R APC (Invitrogen), CD4 PE-Cy7 (Cedarlane Lab. Ltd., Hornby, ON, Canada), CD8a APC and CD3e (both BD). The data were acquired using FACS Vantage™ and analysed by Diva™ software (all BD).

In non-competitive assay, blood samples, bone marrow and spleen were taken from transplanted mice and were analyzed for the presence of GFP or YFP positive cells every week post transplantation. On weeks 8 and 20 post-transplantation, the contribution of transplanted transduced cells to myeloid and lymphoid lineages was analyzed with the same antibody.

Western Blot

For the in vitro part, proteins were extracted from $2 \times 10^6$ (or $3 \times 10^6$ for mutant 1427), 18 days cultured BM cells which were sorted (FACS) for GFP or YFP protein.

The proteins from the in vivo part come from $2 \times 10^6$ sorted GFP or YFP cells from bone marrow and spleen. Proteins were separated on 10% polyacrylamide sodium dodecyl phosphate (SDS) gels and then transferred on Immobilon™ polyvinylidene fluoride (PVDF) membranes (Biorad). A rat anti-mouse HOXB4 antibody was used as probe and the bound antibody was detected with horseradish peroxidase (HRP) conjugated goat anti-rat secondary antibody and visualized using the ECL+ kit (Amersham Biosciences, Piscataway, N.J., USA) via a fudji. The PVDF membrane was exposed to the UV light for 3-4 minutes.

Southern Blot

Genomic DNA was isolated from 4 months post-transplantation bone marrow, spleen and thymus cells (competitive assay) using DNAsol. 15 µg of DNA was digested with either EcoRI/BamHI or XhoI/BamHI (all from Invitrogen), separated on a 1% agarose gel and then transferred on a nylon membrane (Amersham). Blots were probed with a $^{32}$P labelled eGFP probe.

Statistical Analysis

The data obtained from in vitro cultures were fitted using non-linear regression with GraphPad™ Prism software package (GraphPad™ Software, San Diego Calif. USA). The statistical difference was estimated for the TOP parameter of the best fit curve using F-test. The same analysis was performed for the analysis of peripheral reconstitution in non-competitive assay. The differences in bone marrow, spleen and thymus reconstitution were analysed using unpaired t-test. All differences were considered significant at $p<0.05$.

Example 8

Mutated HOXB4 Promotes In Vitro Expansion of Hematopoietic Progenitor Cells

Figure 9:
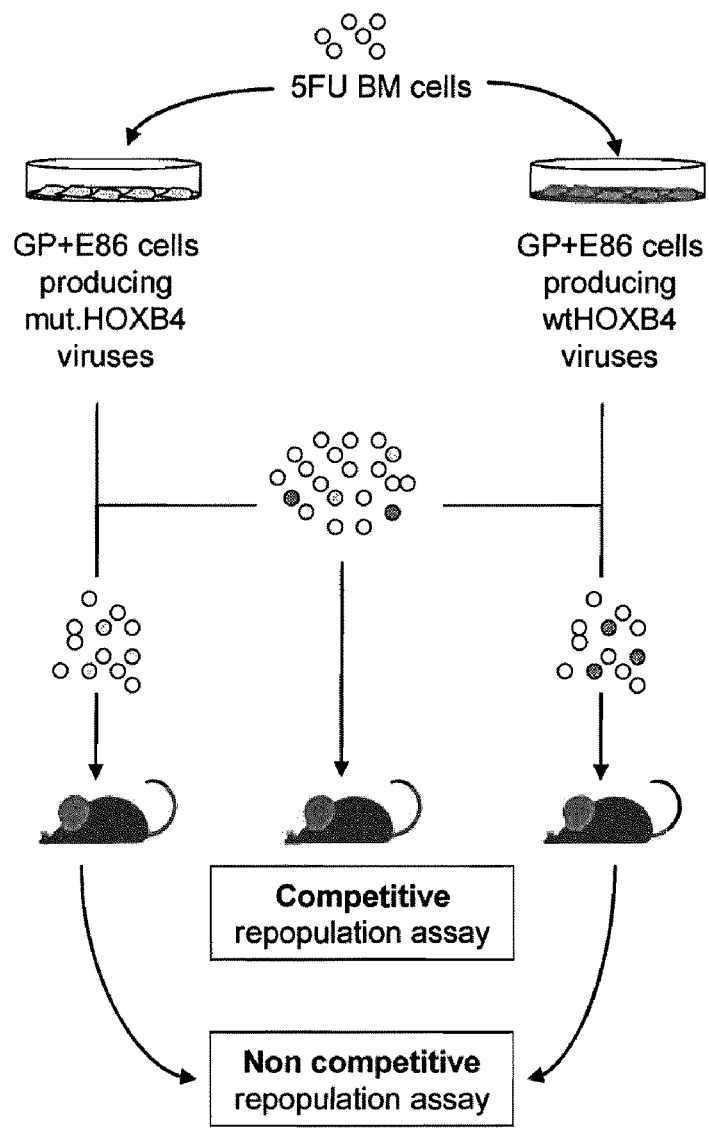
FIG. 9 illustrates the procedure for competitive and non competitive bone marrow cells repopulation assays presented herein with wt HOXB4 and mutated HOXB4.

To establish hematopoietic cells that permanently produce HOXB4 homeoprotein, 5FU bone marrow cells (5Fu is a drug used to enrich BMCs in HSCs. 5Fu is injected in the mice 4 days prior to retrieval of BMC. 5Fu will kill cells in cycle, namely mostly progenitor cells, HSCs being quiescent) were infected with retroviruses carrying mouse wt HOXB4 or mutated HOXB4 cDNA (3 mutants) in a coculture system (GP+E86 producers previously infected with VSV viruses) (FIG. 9). The fluorescent markers YFP and GFP allowed to follow the wt HOXB4 and mutated HOXB4 expressing cells, respectively. As a control, a construct containing the enhanced GFP cDNA only (empty vector) was used.

Figure 10:
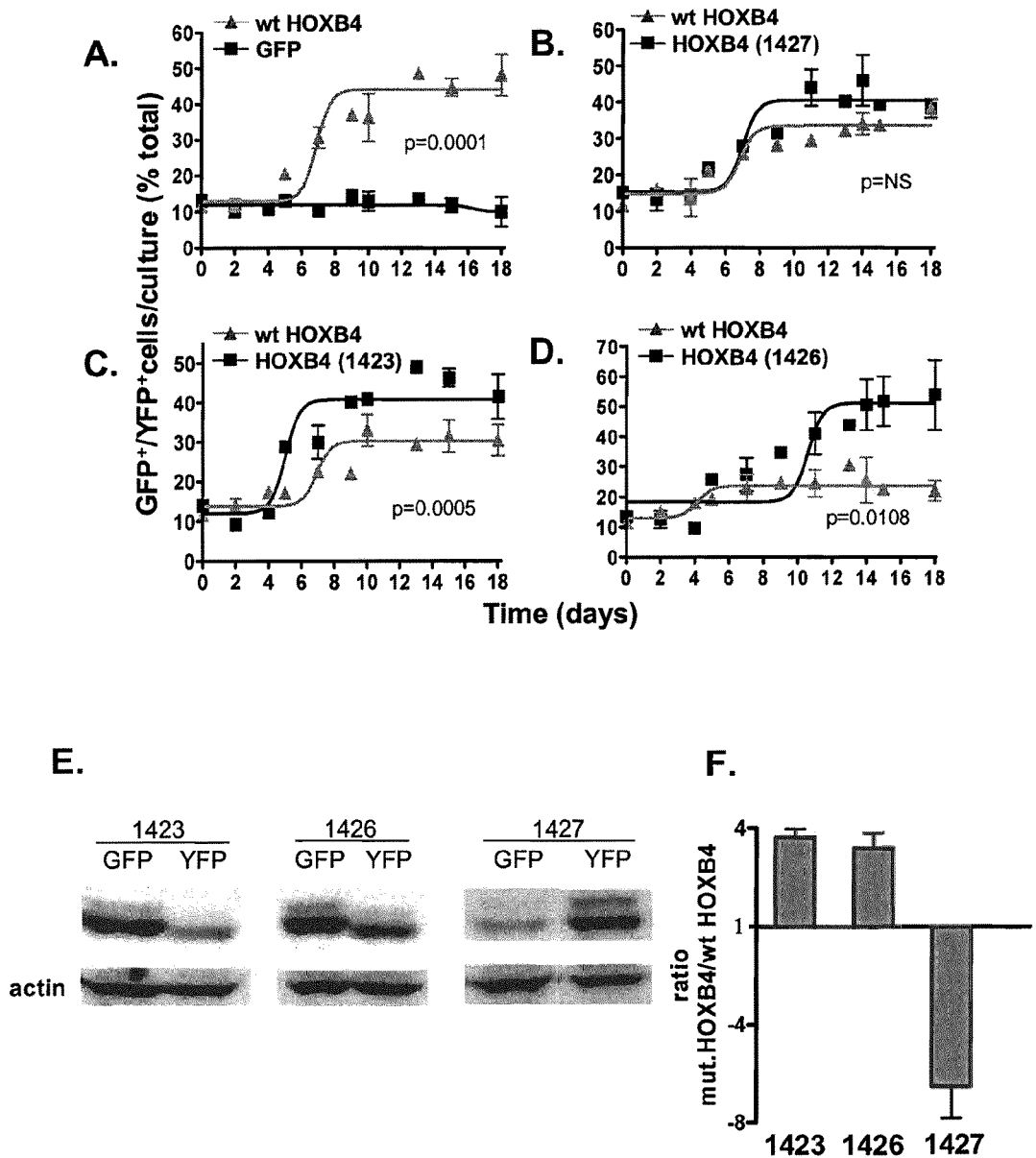
FIG. 10 presents results of in vitro competitive bone marrow cells repopulation assays. The control (empty vector) is compared to wt HOXB4 in Panel A; mutated HOXB4 1427 (HOXB4 Y28A) is compared with wt HOXB4 in Panel B; mutated HOXB4 1423 (HOXB4 L7A) is compared with wt HOXB4 in Panel C; mutated HOXB4 1426 (HOXB4 Y23A) is compared with wt HOXB4 in Panel D. Mutated HOXB4 protein expression in the transduced cells is compared to that of control cells is presented in Panel E and this expression is graphically presented to more clearly show the differences of between mutants and wt (Panel F)

To directly compare the expansion ability of hematopoietic progenitors and HSCs expressing mutated HOXB4 with those expressing wt HOXB4, the 18 days liquid cultures were initiated consisting of 10% wt HOXB4 expressing cells, 10% mutated HOXB4 expressing cells and 80% non infected cells. At indicated times, cell cultures were analysed by flow cytometry for the proportions of YFP and GFP expressing cells (FIG. 10). In the control culture wt HOXB4 (SEQ ID NOS:1 and 2) transduced cells expanded significantly better compared to cells expressing empty vector (P=0.0001) (FIG. 10A). In contrast, the mutated HOXB4 1427 (Y28A) induced expansion of transduced cells (40%) comparable to that of wt HOXB4 (40% vs. 35%) (p=NS) (FIG. 10B). The other two mutants, HOXB4 1423 (L7A) and 1426 (Y23A), induced significantly higher expansion of the cells (40% and 55% respectively, p=0.0005 and p=0.0108, respectively) compared to wt HOXB4 (FIGS. 10C and 10D). The HOXB4 protein expression in transduced cells was evaluated at the end of the culture by Western blotting as described in Example 7. The results (FIG. 10E) demonstrated significantly higher protein expression in the cells transduced with mutants 1423 (L7A) and 1426 (Y23A) compared to that of wt HOXB4, while in the cells transduced with mutated HOXB4 1427 (Y28A), there was 8 times less protein detected (FIG. 10F). Interestingly, the expression of HOXB4 protein correlated with the in vitro expansion; the cells expressing more HOXB4 (1423 and 1426) also demonstrated greater expansion compared to those transduced with wt HOXB4.

Example 9

Figure 11:
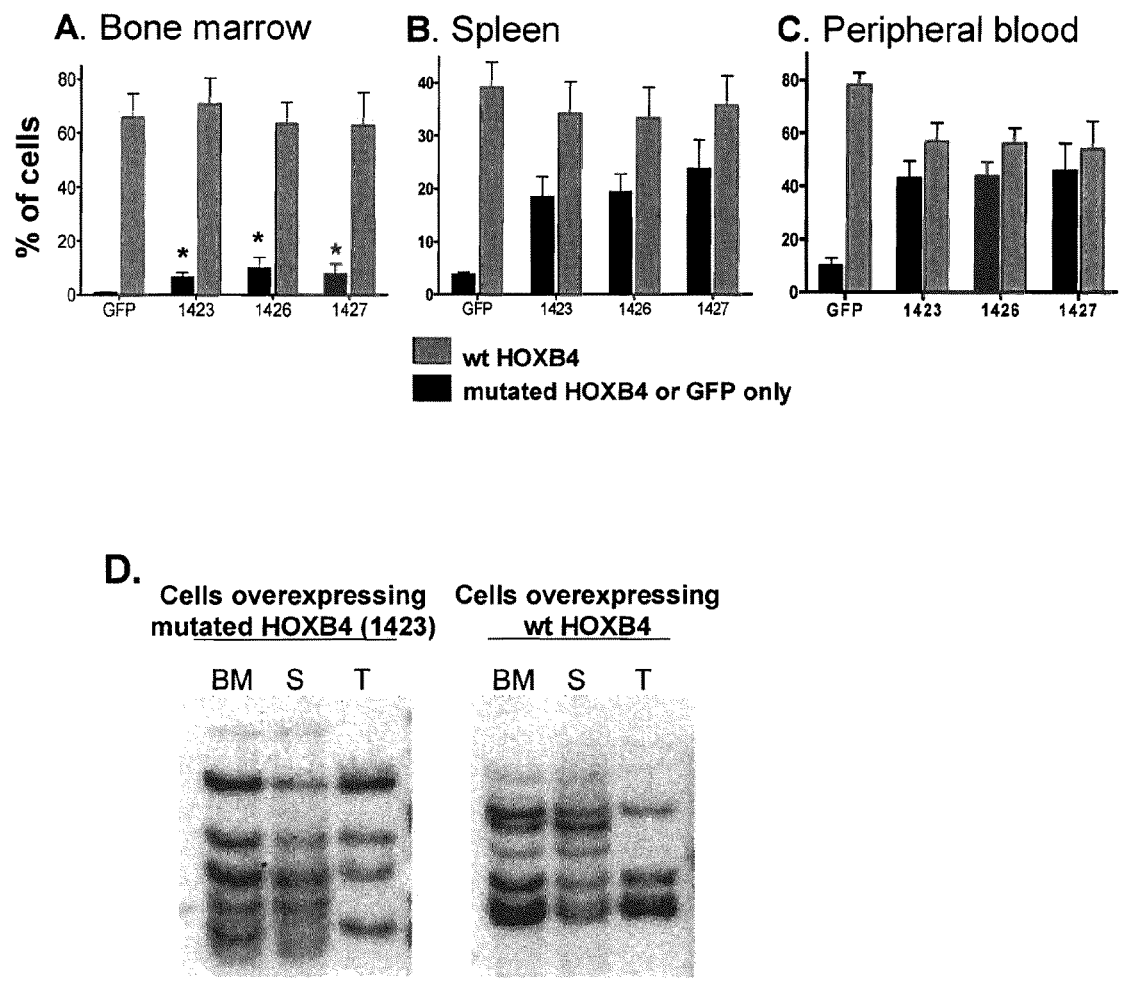
FIG. 11 presents results of in vivo competitive repopulation assays of wt HOXB4 and mutated HOXB4 in transduced cells injected in sublethaly irradiated mice. Repopulation was assessed in bone marrow (panel A), spleen (panel B); and peripheral blood (panel C). Panel D presents a Southern blot of overexpressed wt HOXB4 and mutated HOXB4 (1423) in various tissues (bone marrow, spleen and thymus) and shows that more than one HSC clones are responsible for expansion.

Wild Type HOXB4 Out-Competes Mutated HOXB4 In Vivo Competitive Repopulation Assay To compare the long term repopulation ability of the cells transduced with mutated HOXB4 to those expressing wt HOXB4, the infected cells were mixed in the ratios described in Example 7 and injected in sublethaly irradiated mice. Four months post transplantation, the mice were sacrificed and bone marrow, spleens and peripheral blood were analyzed for contribution of infected cells to hematopoietic reconstitution. The analysis of the bone marrow showed that the wt HOXB4 infected cells contributed to 60-70% of hematopoietic cells of all transplanted mice. In contrast, only 10% of the bone marrow content was represented by mutated HOXB4 transduced cells (FIG. 11A). Interestingly, analysis of the spleen demonstrated that, while the proportion of wt HOXB4 expressing cells was higher than that of mutated HOXB4 infected cells (35% vs. 20-25% respectively), the differences in proportions between the two populations were lower (FIG. 11B). Moreover, the proportion of mutated HOXB4 cells and wt HOXB4 transduced cells in the peripheral blood were not significantly different (45-55%) (FIG. 11C). These data suggested that while mutated HOXB4 expressing cells were detectable in bone marrow of transplanted mice in significantly lower numbers compared to wt HOXB4 transduced cells, their ability to reconstitute peripheral hematopoietic compartment was not compromised.

Example 10

Figure 12:
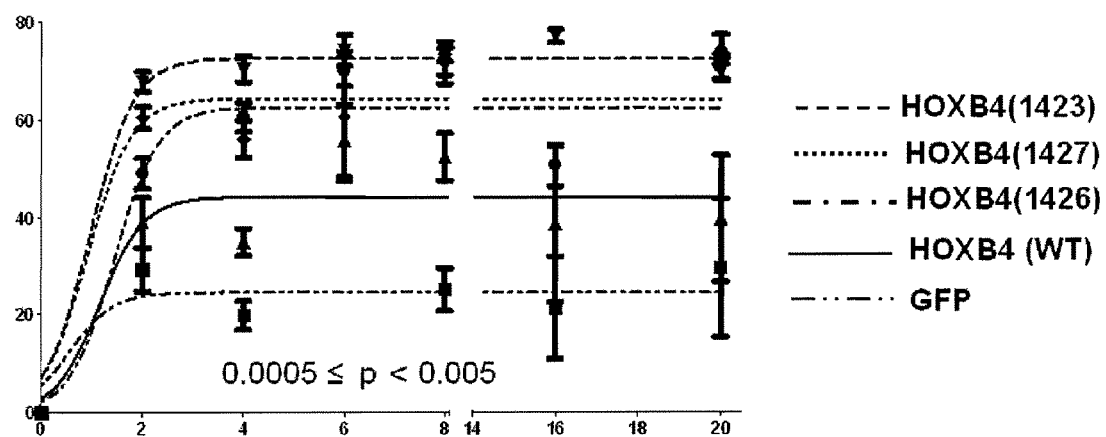
FIG. 12 presents results of in vivo non competitive repopulation assays of wt HOXB4 and mutated HOXB4 in transduced cells injected in sublethaly irradiated mice. Repopulation was assessed in peripheral blood (panel C)

All Mutated HOXB4 Expressing Cells Quickly Reconstitute Peripheral Blood After a Non-Competitive Transplantation To compare the hematopoietic reconstitution competence of mutated HOXB4 transduced cells to that of wild type HOXB4 transduced cells in greater detail, sublethaly irradiated mice were transplanted with a graft consisting of 25% wt HOXB4 or mutated HOXB4 expressing cells and 80% of non-infected cells. The kinetics of hematopoietic reconstitution was followed by flow cytometry analysis of peripheral blood for the presence of the transduced cells. The data presented in FIG. 12 demonstrated that in all mice transplanted with mutated HOXB4 expressing cells peripheral reconstitution commenced significantly faster compared to mice transplanted with wt HOXB4 infected cells. Moreover, the peripheral reconstitution with transduced cells stabilized at the greater level in all groups containing mutated HOXB4 transduced cells (p<0.05) compared to wt HOXB4 group and remained higher until the end of observation period (20 weeks). Together with results from competitive transplantation assay, these results indicate that mutated HOXB4 supports expansion of hematopoietic HSCs and hematopoietic progenitors to a greater extent than wt HOXB4.

Example 11

Figure 13:
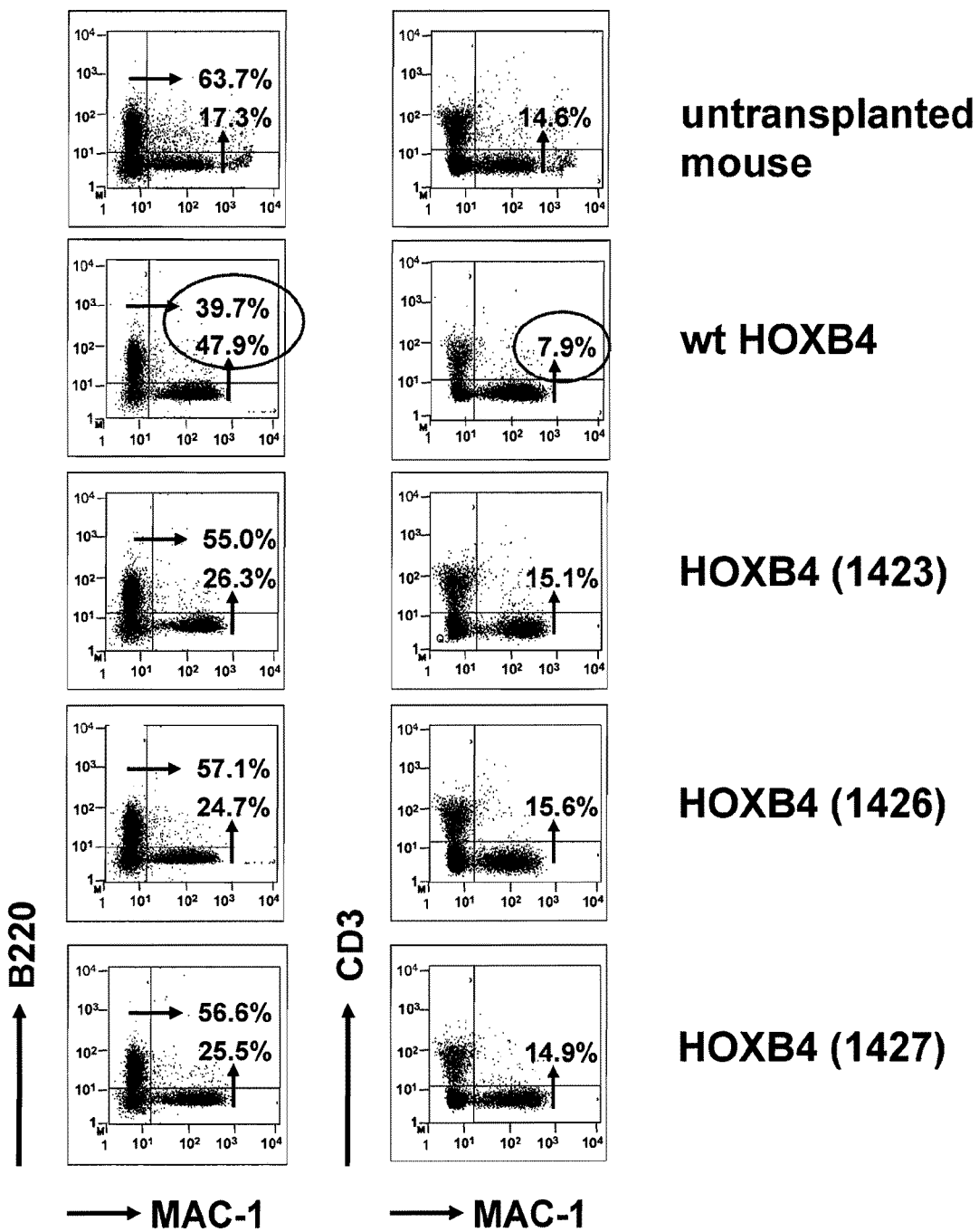
FIG. 13 compares levels of haematopoietic lineages in the peripheral blood of sublethaly irradiated mice injected with cells transduced with wt HOXB4 or mutated HOXB4 14 weeks following transplantation. Repopulation was assessed in peripheral blood.

Mice Transplanted with Mutated HOXB4 Transduced HSC have a Normal Levels of all Hematopoietic Lineages in the Peripheral Blood The peripheral reconstitution of different hematopoietic lineages in mice transplanted with mutated HOXB4 was next evaluated and compared to that generated by wt HOXB4 expressing cells. The proportions of myeloid or lymphoid (B and T) lineages were evaluated for GFP (mutated) or YFP (wt) positive populations (only the cells expressing HOXB4) in order to obtain comparable values. The peripheral blood cells analysis at 14 weeks post-transplantation (FIG. 13) revealed that in mice which received wt HOXB4 transduced cells, the majority of positive for YFP are of myeloid lineage (47.9%) and the proportion of lymphoid B and T cells (39.7% and 7.9%, respectively) are reduced compared to an untransplanted mice (63.7%, 14.6%, respectively).

In contrast, mice transplanted with mutated HOXB4 transduced cells presented a more normal lineage distribution in the transgene expressing population present in the peripheral blood. Similar results were obtained at 16, 18 and 20 weeks post transplantation. Together, these results indicate that mutated HOXB4 not only supports long-term (20 weeks) reconstitution of hematopoiesis in mice but in contrast with its wt HOXB4 counterpart additionally allows for balanced repopulation with myeloid, B cell ant T cell lineages.

Example 12

Figure 14:
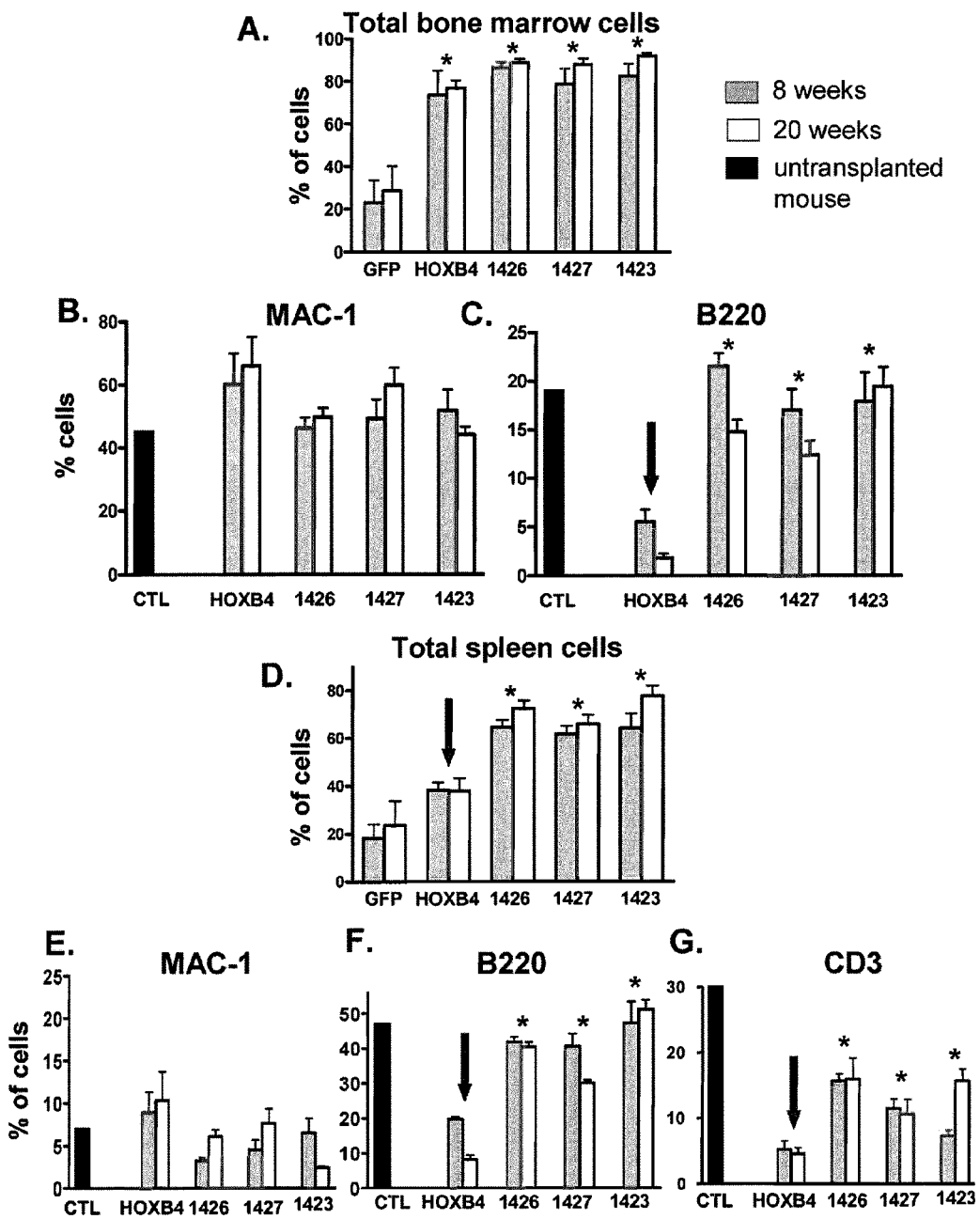
FIG. 14 presents results of in vivo non competitive repopulation assays of wt HOXB4 and mutated HOXB4 in transduced cells injected in sublethaly irradiated mice. Repopulation was assessed bone marrow (Panels A-C) and spleen (Panels D-G) globally and for different lineages.

Mutated HOXB4 Expression Induces Normal Reconstitution of the Bone Marrow and the Spleen To additionally verify the lineage reconstitution of the hematopoietic organs in transplanted mice, the GFP and YFP positive cells recovered from bone marrow and spleens of the transplanted mice were analyzed for the expression of different myeloid and lymphoid markers. The lineage distribution within transgene expressing cells at 8 and 20 weeks post transplantation is presented in FIG. 14. All transgenes (wt HOXB4 and mutated HOXB4) expressing cells reconstituted the bone marrow to significantly higher extent compared to the GFP expressing cells (80-90% vs. 30%, p<0.01) (FIG. 14A). In mice that received wt HOXB4 expressing cells, the proportion of myeloid (MAC-1$^+$) cells in bone marrow was higher (reached 60-70%) at 8 and 20 weeks post transplantation compared to that of non-transplanted and mutated HOXB4 expressing cells transplanted mice (FIG. 14B). In contrast, mice transplanted with wt HOXB4 presented a significantly lower proportion of B cell (B220$^+$) lineage (less then 5%) in bone marrow compared to mutated HOXB4 group (p<0.01) which presented normal B cell lineage proportion in the GFP+ cell population. (FIG. 14C). Similar analysis of the spleen of transplanted mice showed that the wt HOXB4 expressing cells reconstituted the organ to the lesser extent compared to cells expressing mutated HOXB4 (40% vs. 60-70%, p<0.05) (FIG. 14D). Furthermore, the proportion of MAC-1$^+$ cells was increased above normal levels in mice transplanted with wt HOXB4 expressing cells, while it was normal in the two of the tree groups transplanted with mutant HOXB4 (1426 and 1427) and decreased in the third (1423). Similar to that which occurred in the bone marrow, B lineage reconstitution in the spleen was significantly reduced with wt HOXB4 expressing cells compared to the control (10% vs. 45%, p<0.01) while it reached normal levels with mutated HOXB4 transduced cells (FIG. 14F).

While T lineage (CD3$^+$) reconstitution in the spleen was decreased in all transplanted mice (FIG. 6G), the proportion of CD3$^+$ cells was significantly higher in all mutated HOXB4 groups compared to wt HOXB4 group (10-15% vs. 5%, p<0.01).

Example 13

In Vitro Expansion of Hematopoietic Stem Cells by Recombinant TAT-mut-HOXB4 Protein Although HOXB4 was shown to be able to go through the cell membrane (Fichelson, Nature medicine, 2004), it is advantageous to increase its transduction efficiency.

Two viral-derived proteins, the HSV VP16 and the HIV TAT proteins were also shown to induce Intracellular protein delivery. Several studies have shown that TAT is able to translocate through the plasma membrane and to reach the nucleus where it transactivates the viral genome. It was recently shown that this "translocating activity" of TAT resides within residues 47 to 60 of the protein (13-mer) (5'-Gly-Tyr-Gly-Arg-Lys-Lys-Arg-Arg-Gln-Arg-Arg-Arg-Gly-3' (SEQ ID NO:6)). This 13 mer peptide accumulates in cells (nucleus) extremely rapidly (seconds to minutes) at concentrations as low as 100 nM.

Nagahara et al. have reported the ability of several TAT (11 mer) fusion proteins to be efficiently captured by several cell types (including primary hematopoietic cells). According to a recent communication by these authors, this approach has been used with success with at least 50 different proteins (Nagahara, 1998). The incorporated proteins were shown to preserve functional activity.

Dowdy et al. have reported the in vivo (intra-peritoneal) delivery of large (120 kDa) TAT-fusion proteins with a remarkable efficiency of protein transfer to most tissues including "functional protein transfer" to 100% of hematopoietic blood cells in 20 minutes (Schwarze, 1999). Moreover, the authors showed the absence of toxicity for mice receiving up to 1 mg i.p. of TAT-fusion proteins daily for 14 days.

Finally, co-pending US 2004/0082003 demonstrated that recombinant TAT-HOXB4 was efficiently delivered through HSC cell membranes and induced the expansion of these cells.

Mutants of the present invention are thus fused to a PTD fragment so as to form a fusion protein having for instance the following structures (MA-PTD-mutHOXB4 (SEQ ID NOS: 9, 10 (L7A); SEQ ID NOS: 11, 12 (Y23A); SEQ ID NOS: 13, 14 (Y28A); (SEQ ID NOS: 15, 16 (F6A)); ATG-His6-PTD-HA-mut HOXB4 or ATG-His6-PTD-mut HOXB4). PTDs such as those described in U.S. Pat. Nos. 6,645,501 and 6,221,355 can also be used in fusion proteins of the present invention.

Although the present invention has been described hereinabove by way of specific embodiments thereof, it can be modified, without departing from the spirit and nature of the subject invention as defined in the appended claims.

REFERENCES

1. Amsellem S, Pflumio F, Bardinet D et al. Ex vivo expansion of human hematopoietic stem cells by direct delivery of the HOXB4 homeoprotein. Nat Med. 2003; 9:1423-1427.
2. Antonchuk J, Sauvageau G, Humphries R K. HOXB4 overexpression mediates very rapid stem cell regeneration and competitive hematopoietic repopulation. Exp Hematol. 2001; 29:1125-1134.
3. Antonchuk J, Sauvageau G, Humphries R K. HOXB4-induced expansion of adult hematopoietic stem cells ex vivo. Cell. 2002; 109:39-45.
4. Beslu N, Krosl J, Laurin M, Mayotte N, Humphries K R, Sauvageau G. Molecular interactions involved in HOXB4-induced activation of HSC self-renewal. Blood. 2004 Oct. 15; 104(8):2307-14
5. Bhardwaj G, Murdoch B, Wu D et al. Sonic hedgehog induces the proliferation of primitive human hematopoietic cells via BMP regulation. Nat. Immunol. 2001; 2:172-180.
6. Buske C, Feuring-Buske M, Abramovich C et al. Deregulated expression of HOXB4 enhances the primitive growth activity of human hematopoietic cells. Blood. 2002; 100: 862-868.
7. Cellot, S., Krosl, J., Humphries, K., and Sauvageau, G. Sustained in Vitro Trigger of Symmetrical Self-Renewal Divisions in Hoxb4hiPbx1lo Hematopoietic Stem Cells. accepted, Exp Hematol. Février 2007
8. Chowdary D R, Dermody J J, Jha K K, Ozer H L. Accumulation of p53 in a mutant cell line defective in the ubiquitin pathway. Mol Cell Biol. 1994 March; 14(3): 1997-2003.
9. Corish P, Tyler-Smith C. Attenuation of green fluorescent protein half-life in mammalian cells. Protein Eng. 1999 December; 12(12):1035-40.
10. Coulombe P, Rodier G, Pelletier S, Pellerin J, Meloche S. Rapid turnover of extracellular signal-regulated kinase 3 by the ubiquitin-proteasome pathway defines a novel paradigm of mitogen-activated protein kinase regulation during cellular differentiation. Mol Cell Biol. 2003 July; 23(13): 4542-58.
11. de Haan G, Weersing E, Dontje B et al. In Vitro Generation of Long-Term Repopulating Hematopoietic Stem Cells by Fibroblast Growth Factor-1. Developmental Cell. 2003; 4:241-251.
12. Gabellini D, Colaluca I N, Vodermaier H C, Biamonti G, Giacca M, Falaschi A, Riva S, Peverali F A. Early mitotic degradation of the homeoprotein HOXC10 is potentially linked to cell cycle progression. EMBO J. 2003 Jul. 15; 22(14):3715-24.
13. Giglione Biol. chem 2006)=Meinnel T, Serero A, Giglione C. Impact of the N-terminal amino acid on targeted protein degradation. Biol. Chem. 2006 July; 387(7):839-51. Review.
14. Hershko A, Ciechanover A. The ubiquitin system. Annu Rev Biochem. 1998; 67:425-79. Review
15. Karanu F N, Murdoch B, Gallacher L et al. The notch ligand jagged-1 represents a novel growth factor of human hematopoietic stem cells. J Exp Med. 2000; 192:1365-1372.
16. Kroon E, Krosl J, Thorsteinsdottir U, Baban S, Buchberg A M, Sauvageau G. Hoxa9 transforms primary bone marrow cells through specific collaboration with Meisla but not Pbx1b. EMBO J. 1998 Jul. 1; 17(13):3714-25.
17. Kroon E, Thorsteinsdottir U, Mayotte N, Nakamura T, Sauvageau G. NUP98-HOXA9 expression in hemopoietic stem cells induces chronic and acute myeloid leukemias in mice. EMBO J. 2001 Feb. 1; 20(3):350-61.
18. Krosl G GMKJHRSGRD. Human hematopoietic stem cells can be expanded ex vivo using recombinant TAT-HOXB4 protein [abstract]. Biology of Blood and Marrow Transplantation. 2005a; 11:19.
19. Krosl J, Austin P, Beslu N, Kroon E, Humphries R K, Sauvageau G. In vitro expansion of hematopoietic stem cells by recombinant TAT-HOXB4 protein. Nat. Med. 2003 November; 9(11):1428-32.
20. Krosl J, Beslu N, Mayotte N, Humphries R. K, and Sauvageau G: The competitive nature of HOXB4-transduced HSC is limited by PBX1: the generation of ultra-competitive stem cells retaining full differentiation potential. Immunity, 2003, 18: 561-571.
21. Lawrence H J, Helgason C D, Sauvageau G, Fong S, Izon D J, Humphries R K, Largman C. Mice bearing a targeted interruption of the homeobox gene HOXA9 have defects in myeloid, erythroid, and lymphoid hematopoiesis. Blood. 1997 Mar. 15; 89(6):1922-30.
22. Nagahara, H. et al., Nat. Med. 4, 1449-1452, 1998
23. Ohh M, Kim W Y, Moslehi J J, Chen Y, Chau V, Read M A, Kaelin W G Jr. An intact NEDD8 pathway is required for Cullin-dependent ubiquitylation in mammalian cells. EMBO Rep. 2002 February; 3(2):177-82.
24. Ory D S, Neugeboren B A, Mulligan R C. A stable human-derived packaging cell line for production of high titer retrovirus/vesicular stomatitis virus G pseudotypes. Proc Natl Acad Sci USA. 1996 Oct. 15; 93(21):11400-6.
25. Pickart C M. Back to the future with ubiquitin. Cell. 2004 Jan. 23; 116(2):181-90. Review.
26. Pilat S, Carotta S, Schiedlmeier B, Kamino K, Mairhofer A, Will E, Modlich U, Steinlein P, Ostertag W, Baum C, Beug H, Klump H. HOXB4 enforces equivalent fates of ES-cell-derived and adult hematopoietic cells. Proc Natl Acad Sci USA. 2005 Aug. 23; 102(34):12101-6.
27. Schiedlmeier B, Klump H, Will E, Arman-Kalcek G, Li Z, Wang Z, Rimek A, Friel J, Baum C, Ostertag W. High-level ectopic HOXB4 expression confers a profound in vivo competitive growth advantage on human cord blood CD34+ cells, but impairs lymphomyeloid differentiation. Blood. 2003 Mar. 1; 101(5):1759-68.
28. Schwarze, S. R. et al., Science 285, 1569-1572. 1999
29. Thorsteinsdottir U, Krosl J, Kroon E, Haman A, Hoang T, Sauvageau G. The oncoprotein E2A-Pbx1a collaborates with Hoxa9 to acutely transform primary bone marrow cells. Mol Cell Biol. 1999 September; 19(9):6355-66.
30. Thorsteinsdottir U, Mamo A, Kroon E, Jerome L, Bijl J, Lawrence H J, Humphries K, Sauvageau G. Overexpression of the myeloid leukemia-associated Hoxa9 gene in bone marrow cells induces stem cell expansion. Blood. 2002 Jan. 1; 99(1):121-9.
31. Willert K, Brown J D, Danenberg E et al. Wnt proteins are lipid-modified and can act as stem cell growth factors. Nature. 2003; 423:448-452.
32. Zhang Y, Morrone G, Zhang J, Chen X, Lu X, Ma L, Moore M, Zhou P. CUL-4A stimulates ubiquitylation and degradation of the HOXA9 homeodomain protein. EMBO J. 2003 Nov. 17; 22(22):6057-67.

The invention claimed is:

1. A mutated human HoxB4 polypeptide, said mutated human HoxB4 polypeptide differs from the wild type human HoxB4 polypeptide as set forth in SEQ ID NO: 2 only by a mutation selected from the group consisting of a) a mutation replacing the amino acid residue at position 6, 7, 23 and/or 28 of SEQ ID NO: 2 with an aliphatic nonpolar neutral amino acid residue, b) a deletion of the first 31 to 35 amino acid residues of the sequence set forth in SEQ ID NO: 2, and c) a combination of a) and b), wherein said mutation reduces the susceptibility of the polypeptide to ubiquitin-proteasome degradation, and said mutated HoxB4 polypeptide has the activity of enhancing expansion of a hematopoietic stem cell containing population.

2. The polypeptide of claim 1, wherein said at least one mutation replaces the amino acid residue at position 6 with an aliphatic nonpolar neutral amino acid residue.

3. The polypeptide of claim 1, wherein said at least one mutation replaces the amino acid residue at position 7 with an aliphatic nonpolar neutral amino acid residue.

4. The polypeptide of claim 1, wherein said at least one mutation replaces the amino acid residue at position 23 with an aliphatic nonpolar neutral amino acid residue.

5. The polypeptide of claim 1, wherein said at least one mutation replaces the amino acid residue at position 28 with an aliphatic nonpolar neutral amino acid residue.

6. The polypeptide of claim 1, wherein the aliphatic nonpolar neutral amino acid residue is selected from the group consisting of glycine, alanine and valine.

7. The polypeptide of claim 6, wherein the aliphatic nonpolar neutral amino acid residue is alanine.

8. The polypeptide of claim 1, wherein said at least one mutation is a deletion of the first N-terminal 31 to 35 amino acid residues.

9. The polypeptide of claim 8, the amino acid sequence of which comprises the sequence as set forth in SEQ ID NO:4.

10. An isolated polypeptide comprising the polypeptide of claim 1 and a protein transduction domain (PTD).

11. The polypeptide of claim 10, wherein the PTD is a HIV-derived peptide.

12. The polypeptide of claim 11, wherein the HIV-derived peptide is a $NH_2$-terminal PTD from a transactivating protein (TAT).

13. The polypeptide of claim 12, wherein the $NH_2$-terminal PTD from a TAT comprises the sequence set forth in SEQ ID NO:6.

14. A kit comprising the polypeptide of claim 1 and instructions to use the polypeptide to expand a hematopoietic stem cell-containing population.

15. A method for enhancing expansion of a hematopoietic stem cell (HSC)-containing population comprising contacting the HSC population with a therapeutically effective amount of the polypeptide of claim 1, whereby the HSC-containing population is expanded.

16. The method of claim 15, wherein the contacting is performed ex vivo.

17. The method of claim 15, wherein the contacting is performed in vivo.

18. The method of claim 15, wherein the HSC-containing population is obtained from umbilical cord blood.

19. The method of claim 15, wherein the HSC-containing population is obtained from peripheral blood.

20. The method of claim 15, wherein the HSC-containing population is obtained from bone marrow.

21. The method of claim 15, wherein the HSC-containing population is that of a human.

* * * * *